United States Patent
Johnson et al.

(10) Patent No.: US 9,211,250 B2
(45) Date of Patent: Dec. 15, 2015

(54) HETEROGENEOUS POLYMERIC MICELLES FOR INTRACELLULAR DELIVERY

(75) Inventors: Paul Johnson, Snohomish, WA (US);
Patrick S. Stayton, Seattle, WA (US);
Allan S. Hoffman, Seattle, WA (US);
Robert Overell, Shoreline, WA (US);
Anna Gall, Woodinville, WA (US);
Mary Prieve, Lake Forest Park, WA (US);
Amber Paschal, Redmond, WA (US);
Charbel Diab, Seattle, WA (US);
Priyadarsi De, Mohanpur (IN)

(73) Assignees: University of Washington, Seattle, WA (US); PhaseRx, Inc., Seattle, WA (US)

( * ) Notice: Subject to any disclaimer, the term of this patent is extended or adjusted under 35 U.S.C. 154(b) by 208 days.

(21) Appl. No.: 13/059,946

(22) PCT Filed: May 13, 2009

(86) PCT No.: PCT/US2009/043859
§ 371 (c)(1),
(2), (4) Date: May 2, 2011

(87) PCT Pub. No.: WO2010/021770
PCT Pub. Date: Feb. 25, 2010

(65) Prior Publication Data
US 2012/0021514 A1 Jan. 26, 2012

Related U.S. Application Data

(60) Provisional application No. 61/091,294, filed on Aug. 22, 2008, provisional application No. 61/112,054, filed on Nov. 6, 2008, provisional application No. 61/112,048, filed on Nov. 6, 2008, provisional application No. 61/140,774, filed on Dec. 24, 2008, provisional application No. 61/140,779, filed on Dec. 24, 2008, provisional application No. 61/171,358, filed on Apr. 21, 2009, provisional application No. 61/171,369, filed on Apr. 21, 2009.

(51) Int. Cl.
| | |
|---|---|
| *C12N 5/071* | (2010.01) |
| *C08G 81/00* | (2006.01) |
| *A61K 9/00* | (2006.01) |
| *A61K 9/107* | (2006.01) |
| *A61K 47/48* | (2006.01) |
| *C08L 53/00* | (2006.01) |
| *C12N 15/88* | (2006.01) |

(52) U.S. Cl.
CPC ............. *A61K 9/0019* (2013.01); *A61K 9/1075* (2013.01); *A61K 47/48176* (2013.01); *C08L 53/00* (2013.01); *C12N 15/88* (2013.01)

(58) Field of Classification Search
None
See application file for complete search history.

(56) References Cited

U.S. PATENT DOCUMENTS

| | | | |
|---|---|---|---|
| 4,699,784 A | 10/1987 | Shih | |
| 5,057,313 A | 10/1991 | Shih | |
| 6,306,994 B1 | 10/2001 | Donald | |
| 6,359,054 B1 * | 3/2002 | Lemieux et al. | 524/505 |
| 6,383,811 B2 | 5/2002 | Wolff | |
| 6,410,057 B1 | 6/2002 | Kweon-Choi | |
| 6,780,428 B2 | 8/2004 | Ranger | |
| 6,835,393 B2 * | 12/2004 | Hoffman et al. | 424/450 |
| 6,919,091 B2 | 7/2005 | Trubetskoy | |
| 6,939,564 B2 * | 9/2005 | Ranger et al. | 424/497 |
| 7,033,607 B2 | 4/2006 | Trubetskoy | |
| 7,094,810 B2 | 8/2006 | Sant | |
| 7,098,032 B2 | 8/2006 | Trubetskoy | |
| 7,217,776 B1 | 5/2007 | Mallapragada | |
| 7,374,778 B2 | 5/2008 | Hoffman | |
| 7,510,731 B2 | 3/2009 | Ranger | |
| 7,524,680 B2 | 4/2009 | Wolff | |
| 7,718,193 B2 | 5/2010 | Stayton | |
| 7,737,108 B1 | 6/2010 | Hoffman | |
| 8,367,113 B2 | 2/2013 | Gu et al. | |
| 2001/0007666 A1 | 7/2001 | Hoffman | |
| 2003/0134420 A1 | 7/2003 | Lollo | |
| 2003/0191081 A1 | 10/2003 | Lemieux | |
| 2003/0211167 A1 | 11/2003 | Gustavsson | |
| 2004/0054127 A1 | 3/2004 | Jin | |
| 2004/0072784 A1 | 4/2004 | Sant | |
| 2004/0151775 A1 | 8/2004 | Rozema | |
| 2004/0162235 A1 | 8/2004 | Trubetskoy | |
| 2005/0070721 A1 | 3/2005 | Bae | |
| 2005/0118252 A1 * | 6/2005 | Bae et al. | 424/450 |
| 2005/0220880 A1 | 10/2005 | Lewis | |
| 2005/0260276 A1 | 11/2005 | Yang | |
| 2006/0134221 A1 | 6/2006 | Geall | |

(Continued)

FOREIGN PATENT DOCUMENTS

| | | |
|---|---|---|
| EP | 0 321 233 A1 | 6/1989 |
| EP | 2 180 004 A1 | 4/2010 |

(Continued)

OTHER PUBLICATIONS

Convertine AJ, Development of a novel endosomolytic diblock copolymer for siRNA delivery, JCR, 2009, 133, 221-229.*
Benoit, D.S.W., et al., "Resensitizing Multidrug Resistant Cells to Doxorubicin Through plk1 Knockdown Using a Novel pH-Responsive Micelle siRNA Delivery System," Abstracts of Society for Biomaterials Meeting, Apr. 22, 2009, 1 page.
Bulmus, V., et al., "A New pH-Responsive and Glutathione-Reactive, Endosomal Membrane-Disruptive Polymeric Carrier for Intracellular Delivery of Biomolecular Drugs," Journal of Controlled Release 93(2):105-120, Dec. 2003.
Convertine, A.J., et al., "Development of a Novel Endosomolytic Diblock Copolymer for siRNA Delivery," Journal of Controlled Release 133(3):221-229, Feb. 2009.

(Continued)

*Primary Examiner* — Frederick Krass
*Assistant Examiner* — Celeste A Roney
(74) *Attorney, Agent, or Firm* — Christensen O'Connor Johnson Kindness PLLC

(57) ABSTRACT

Compositions comprising a heterogeneous polymeric micelle and an agent (e.g., a polynucleotide) associated with the micelle are disclosed, together with methods for intracellular delivery of such agent.

9 Claims, 14 Drawing Sheets

(56) References Cited

U.S. PATENT DOCUMENTS

| | | |
|---|---|---|
| 2006/0165810 A1 | 7/2006 | Discher |
| 2006/0171980 A1 | 8/2006 | Helmus |
| 2006/0217285 A1 | 9/2006 | Destarac |
| 2006/0235161 A1 | 10/2006 | Heller |
| 2007/0003609 A1 | 1/2007 | Collin-Djangone |
| 2007/0010632 A1 | 1/2007 | Kaplan et al. |
| 2007/0037891 A1 | 2/2007 | Esfand |
| 2007/0059271 A1 | 3/2007 | Kataoka |
| 2007/0110709 A1 | 5/2007 | Ranger |
| 2007/0134188 A1* | 6/2007 | Collin-Djangone et al. ............ 424/70.13 |
| 2007/0224241 A1 | 9/2007 | Stayton |
| 2008/0069902 A1 | 3/2008 | Zhao |
| 2008/0081075 A1 | 4/2008 | Hsiue |
| 2008/0171067 A1 | 7/2008 | Govindan |
| 2008/0243049 A1 | 10/2008 | Hardy |
| 2009/0036625 A1 | 2/2009 | Chang |
| 2010/0150952 A1 | 6/2010 | Stayton |
| 2011/0123636 A1 | 5/2011 | Stayton |
| 2011/0143434 A1 | 6/2011 | Stayton |
| 2011/0143435 A1 | 6/2011 | Stayton |
| 2011/0281354 A1 | 11/2011 | Stayton |
| 2011/0281934 A1 | 11/2011 | Johnson et al. |
| 2011/0286957 A1 | 11/2011 | Prieve et al. |
| 2014/0228516 A1 | 8/2014 | Stayton |

FOREIGN PATENT DOCUMENTS

| | | |
|---|---|---|
| FR | 2 767 829 A1 | 3/1999 |
| WO | 99/29303 A1 | 6/1999 |
| WO | 01/87227 A2 | 11/2001 |
| WO | WO-01-87227 * | 11/2001 |
| WO | 03/087188 A1 | 10/2003 |
| WO | 2005/108614 A2 | 11/2005 |
| WO | 2006/016166 A1 | 2/2006 |
| WO | 2007/008300 A2 | 1/2007 |
| WO | 2007/109584 A1 | 9/2007 |
| WO | 2008/004978 A1 | 1/2008 |
| WO | 2008/022309 A2 | 2/2008 |
| WO | WO-2008-022309 * | 2/2008 |
| WO | 2008/071009 A1 | 6/2008 |
| WO | 2008/085556 A2 | 7/2008 |
| WO | 2008/148174 A1 | 12/2008 |
| WO | 2008/153940 A1 | 12/2008 |
| WO | 2009/009025 A1 | 1/2009 |
| WO | 2009/021728 A2 | 2/2009 |
| WO | 2009/140421 A2 | 11/2009 |
| WO | 2009/140423 A2 | 11/2009 |
| WO | 2009/140427 A2 | 11/2009 |
| WO | 2009/140429 A2 | 11/2009 |
| WO | 2009/140432 A2 | 11/2009 |
| WO | WO-2009-014021 * | 11/2009 |
| WO | 2010/021770 A1 | 2/2010 |
| WO | 2010/053596 A1 | 5/2010 |
| WO | 2010/053597 A2 | 5/2010 |
| WO | 2010/054266 A2 | 5/2010 |
| WO | 2010/077678 A2 | 7/2010 |

OTHER PUBLICATIONS

Dufresne, M.-H., et al., "Characterization of Polyion Complex Micelles Designed to Address the Challenges of Oligonucleotide Delivery," Pharmaceutical Research 25(9):2083-2093, Sep. 2008.

Duvall, C.L., et al., "Polymer Enhanced Intracellular Delivery of a Pro-Apoptotic Peptide for Cancer Therapy," Abstracts of Society for Biomaterials Meeting, Apr. 22, 2009, 1 page.

El-Sayed, M.E.H., et al., "Rational Design of Composition and Activity Correlations for pH-Sensitive and Glutathione-Reactive Polymer Therapeutics," Journal of Controlled Release 101(1-3):47-58, Jan. 2005.

El-Sayed, M.E.H., et al., "Smart Polymeric Carriers for Enhanced Intracellular Delivery of Therapeutic Macromolecules," Expert Opinion on Biological Therapy 5(1):23-32, Jan. 2005.

Funhoff, A.M., et al., "Endosomal Escape of Polymeric Gene Delivery Complexes Is Not Always Enhanced by Polymers Buffering at Low pH," Biomacromolecules 5(1):32-39, Jan.-Feb. 2004.

Gaucher, G., et al., "Block Copolymer Micelles: Preparation, Characterization and Application in Drug Delivery," Journal of Controlled Release 109(1-3):169-188, Dec. 2005.

Henry, S.M., et al., "pH-Responsive Poly(styrene-alt-maleic anhydride) Alkylamide Copolymers for Intracellular Drug Delivery," Biomacromolecules 7(8):2407-2414, Aug. 2006.

Heredia, K.L., et al., "Reversible siRNA—Polymer Conjugates by RAFT Polymerization," Chemical Communications 28(28):3245-3247, Jul. 2008.

Inoue, T., et al., "An AB Block Copolymer of Oligo(methyl methacrylate) and Poly(acrylic acid) for Micellar Delivery of Hydrophobic Drugs," Journal of Controlled Release 51(2-3):221-229, Feb. 1998.

Jensen, K.D., et al., "Antisense Oligonucleotides Delivered to the Lysosome Escape and Actively Inhibit the Hepatitis B Virus," Bioconjucate Chemistry 13(5):975-984, Sep.-Oct. 2002.

Jeong, J.H., et al., "siRNA Conjugate Delivery Systems," Bioconjugate Chemistry 20(1):5-14, Jan. 2009.

Kataoka, K., et al., "Smart Polymeric Micelles as Nanocarriers for Oligonucleotides and siRNA Delivery," Nucleic Acids Symposium Series 49(1):17-18, Sep. 2005.

Kulkarni, S., et al, "Controlling the Aggregation of Conjugates of Streptavidin With Smart Block Copolymers Prepared Via the RAFT Copolymerization Technique," Biomacromolecules 7(10):2736-2741, Oct. 2006.

Meyer, M., et al., "Synthesis and Biological Evaluation of a Bioresponsive and Endosomolytic siRNA-Polymer Conjugate," Molecular Pharmaceutics 6(3):752-762, May-Jun. 2009.

Murthy, N., et al., "Bioinspired pH-Responsive Polymers for the Intracellular Delivery of Biomolecular Drugs," Bioconjugate Chemistry 14(2):412-419, Mar.-Apr. 2003.

Murthy, N., et al., "The Design and Synthesis of Polymers for Eukaryotic Membrane Disruption," Journal of Controlled Release 61(1-2):137-143, Aug. 1999.

Oishi, M., et al., "Lactosylated Poly(ethylene glycol)-siRNA Conjugate Through Acid-Labile Beta-Thiopropionate Linkage to Construct pH-Sensitive Polyion Complex Micelles Achieving Enhanced Gene Silencing in Hepatoma Cells," Journal of the American Chemical Society 127(6):1624-1625, Feb. 2005.

Peppas, N.A., "Is There a Future in Glucose-Sensitive, Responsive Insulin Delivery Systems?" Drug Delivery Science and Technology 14(4):247-256, Sep. 2004.

Read, M.L, et al., "Physicochemical and Biological Characterisation of an Antisense Oligonucleotide Targeted Against the bcl-2 mRNA Complexed With Cationic-Hydrophilic Copolymers," European Journal of Pharmaceutical Sciences 10(3):169-177, May 2000.

Segura, T., and J.A. Hubbell, "Synthesis and in Vitro Characterization of an ABC Triblock Copolymer for siRNA Delivery," Bioconjugate Chemistry 18(3):736-745, May 2007.

Stayton, P.S., and A.S. Hoffman, "'Smart' pH-Responsive Carriers for Intracellular Delivery of Biomolecular Drugs," in V. Torchilin (ed.), "Fundamental Biomedical Technologies: Multifunctional Pharmaceutical Nanocarriers," Springer Science+Business Media, LLC, New York, May 2008, vol. 4, pp. 143-159.

Stayton, P.S., et al., "Intelligent Biohybrid Materials for Therapeutic and Imaging Agent Delivery," Proceedings of the IEEE 93(4):726-736, Apr. 2005.

Torchilin, V.P., "Micellar Nanocarriers: Pharmaceutical Perspectives," Pharmaceutical Research 24(1):1-16, Jan. 2007.

Wang, L., et al., "Delivery of Antisense Oligonucleotides Using HPMA Polymer: Synthesis of a Thiol Polymer and Its Conjugation to Water-Soluble Molecules," Bioconjugate Chemistry 9(6):749-757, Nov.-Dec. 1998.

Yamamoto, S.-I., et al., "Temperature- and pH-Responsive Dense Copolymer Brushes Prepared by ATRP," Macromolecules 41(19):7013-7020, Oct. 2008.

Yessine, M.-A., et al., "Proton-Actuated Membrane-Destabilizing Polyion Complex Micelles," Bioconjugate Chemistry 18(3):1010-1014, May-Jun. 2007.

(56) References Cited

OTHER PUBLICATIONS

Fishbein, I., et al., "Local Delivery of Gene Vectors From Bare-Metal Stents by Use of a Biodegradable Synthetic Complex Inihibits In-Stent Restenosis in Rat Carotid Arteries," Circulation 117(16):2096-2103, Apr. 2008.

Invitiation to Pay Additional Fees and Partial International Search Report mailed Apr. 26, 2011, issued in corresponding International Application No. PCT/US2010/056993, filed Nov. 17, 2010, 6 pages.

Varghese, O.P., et al., "In Situ Cross-Linkable High Molecular Weight Hyaluronan—Bisphosphonate Conjugate for Localized Delivery and Cell-Specific Targeting: A Hydrogel Linked Prodrug Approach," Journal of the American Chemical Society 131(25):8781-8783, Jul. 2009.

Cho, Y.W., et al., "Polycation Gene Delivery Systems: Escape From Endosomes to Cytosol," Journal of Pharmacy and Pharmacology 55(6):721-734, Jun. 2003.

International Search Report and Written Opinion mailed Mar. 7, 2011, issued in corresponding International Application No. PCT/US2010/056565, filed Nov. 12, 2010, 12 pages.

Extended European Search Report mailed Sep. 27, 2011, issued in corresponding European Application No. 09 80 8542, filed May 13, 2009, 5 pages.

International Search Report and Written Opinion mailed Dec. 30, 2009, in corresponding International Patent Application No. PCT/US2009/043859, filed May 13, 2009, 11 pages.

Non-Final Office Action mailed Jun. 18, 2013, from U.S. Appl. No. 12/992,525, filed Feb. 8, 2011, which is a co-pending application of the present application.

Final Office Action mailed Jul. 16, 2013, from U.S. Appl. No. 12/992,536, filed Feb. 25, 2011, which is a co-pending application of the present application.

Extended European Search Report mailed Feb. 5, 2014, issued in corresponding European Application No. 09 825 146.5, filed May 13, 2009, 9 pages.

Cheung, C.Y., et al., "A pH-Sensitive Polymer That Enhances Cationic Lipid-Mediated Gene Transfer," Bioconjugate Chemistry 12(6):906-910, Oct. 2001.

Hood, J.D., et al., "Tumor Regression by Targeted Gene Delivery to the Neovasculature," Science, New Series 296 (5577):2404-2407, Jun. 2002.

Jeong, Y.-I., et al., "Cellular Recognition of Paclitaxel-Loaded Polymeric Nanoparticles Composed of Poly(γ-benzyl L-glutamate) and Poly(ethylene glycol) Diblock Copolymer Endcapped With Galactose Moiety," International Journal of Pharmaceutics 296(2005):151-161, Apr. 2005.

Joralemon, M.J., et al., "Synthesis, Characterization, and Bioavailability of Mannosylated Shell Cross-Linked Nanoparticles," Biomacromolecules 5(3):903-913, May-Jun. 2004.

Kabanov, A.V., et al., "Pluronic Micelles as a Tool for Low-Molecular Compound Vector Delivery Into a Cell: Effect of Staphylococcus-aureus Enterotoxin B on Cell Loading With Micelle Incorporated Fluorescent Dye," Biochemistry International 26(6):1035-1042, May 1992.

Kyriakides, T.R., et al., "pH-Sensitive Polymers That Enhance Intracellular Drug Delivery in Vivo," Journal of Controlled Release 78(1-3):295-303, Jan. 2002.

Le Garrec, D., et al., "Micelles in Anticancer Drug Delivery," American Journal of Drug Delivery 2(1):15-42, Mar. 2004.

Lee, E.S., et al., "Super pH-Sensitive Multifunctional Polymeric Micelle," Nano Letters 5(2):325-329, Feb. 2005.

Nagasaki, Y. et al., "Sugar-Installed Block Copolymer Micelles: Their Preparation and Specific Interaction With Lectin Molecules," Biomacromolecules 2(4):1067-1070, Winter 2001.

Raso, V., "Intracellular Targeting Using Bispecific Antibodies," Methods in Molecular Medicine 25:37-49, Jan. 2000.

Sawant, R.M., et al., "'Smart' Drug Delivery Systems: Double-Targeted pH-Responsive Pharmaceutical Nanocarriers," Bioconjugate Chemistry 17:943-949, Jun. 2006.

Turk, M.J., et al., "Characterization of a Novel pH-Sensitive Peptide That Enhances Drug Release From Folate-Targeted Liposomes at Endosomal pHs," Biochimica et Biophysica Acta 1559(1):56-68, Feb. 2002.

Wakebayashi, D., et al., "Lactose-Conjugated Polyion Complex Micelles Incorporating Plasmid DNA as a Targetable Gene Vector System: Their Preparation and Gene Transfecting Efficiency Against Cultured HepG2 Cells," Journal of Controlled Release 95(3):653-664, Mar. 2004.

Yasugi, K., et al., "Sugar-Installed Polymer Micelles: Synthesis and Micellization of Poly(ethylene glycol)-Poly(D,L-lactide) Block Copolymers Having Sugar Groups at the PEG Chain End," Macromolecules 32:8024-8032, Nov. 1999.

Yoo, H.S., and T.G. Park, "Folate Receptor Targeted Biodegradable Polymeric Doxorubicin Micelles," Journal of Controlled Release 96(2):273-283, Apr. 2004.

Cheng, Z., et al., "Brush-Type Amphiphilic Diblock Copolymers from 'Living'/Controlled Radical Polymerizations and Their Aggregation Behavior," Langmuir 21(16):7180-7185, Jul. 2005.

Finne-Wistrand, A. and A.-C. Albertson, "The Use of Polymer Design in Resorbable Colloids," Annual Review of Materials Research 36:369-395, Aug. 2006.

Final Office Action mailed Apr. 4, 2014, from U.S. Appl. No. 12/992,517, filed Feb. 9, 2011, 21 pages.

Final Office Action mailed Mar. 21, 2014, from U.S. Appl. No. 13/127,962, filed Jul. 26, 2011, 11 pages.

Office Action mailed Apr. 25, 2014, from U.S. Appl. No. 12/992,536, filed Feb. 25, 2011, 13 pages.

Office Action mailed Apr. 7, 2014, from U.S. Appl. No. 13/127,959, filed Jul. 27, 2011, 15 pages.

Oishi M., et al., "pH-Responsive Oligodeoxynucleotide (ODN)-Poly(Ethylene Glycol) Conjugate Through Acid-Labile β-Thiopropionate Linkage: Preparation and Polyion Complex Micelle Formation," Biomacromolecules 4(5):1426-1432, Aug. 2003.

Wei, J.-S., et al., "Temperature- and pH-Sensitive Core-Shell Nanoparticles Self-Assembled from Poly(N-Isopropylacrylamide-CO-Acrylic Acid-CO-Cholesteryl Acrylate) for Intracellular Delivery of Anticancer Drugs," Frontiers in Bioscience 10:3058-3067, Sep. 2005.

York, A.W. et al., "Advances in the Synthesis of Amphiphilic Block Copolymers via RAFT Polymerization: Stimuli-Responsive Drug and Gene Delivery," Advanced Drug Delivery Reviews 60(9):1018-1036, Jun. 2008.

Stayton, P.S., "Polymeric Carrier," U.S. Appl. No. 14/630,477, filed Feb. 24, 2015.

Office Action mailed May 20, 2015, from U.S. Appl. No. 13/127,962, filed Jul. 26, 2011, 10 pages.

Agarwal, a., et al., "Dual-Role Self-Assembling Nanoplexes for Efficient Gene Transfection and Sustained Gene Delivery," Biomaterials 29(5):607-617, Feb. 2008.

Alvarez-Lorenzo, C., et al., "Biophysical Characterization of Complexation of DNA with Block Copolymers of Poly(2-dimethylaminoethyl) Methacrylate, Poly(ethylene oxide), and Poly(propylene oxide)," Langmuir 21(11):5142-5148, May 24, 2005.

Boeckle, S., et al., "Purification of Polyethylenimine Polyplexes Highlights the Role of Free Polycations in Gene Transfer," The Journal of Gene Medicine 6(10):1102-1111, Oct. 2004.

Eliyahu, H., et al., "Novel Dextran-Spermine Conjugates as Transfecting Agents: Comparing Water-Soluble and Micellar Polymers," Gene Therapy 12(6):494-503, Mar. 2005.

Gary, D.J., et al., "Polymer-Based siRNA Delivery: Perspectives on the Fundamental and Phenomenological Distinctions from Polymer-Based Dna Delivery," Journal of Controlled Release 121(1-2):64-73, Aug. 16, 2007.

Germershaus, O., et al., "Gene Delivery Using Chitosan, Trimethyl Chitosan or Polyethylenglycol-graft-trimethyl Chitosan Block Copolymers: Establishment of Structure-Activity Relationships in Vitro," Journal of Controlled Release 125(2):145-154, Jan. 22, 2008.

Guo, Y., et al., "Capillary Electrophoresis Analysis of Poly(ethylene glycol) and Ligand-Modified Polylysine Gene Delivery Vectors," Analytical Biochemistry 363(2):204-209, Apr. 15, 2007.

(56) References Cited

OTHER PUBLICATIONS

Jiang, T., et al., "Adsorption of Plasmid DNA onto N,N'-(Dimethylamino)ethyl-methacrylate Graft-Polymerized Poly-L-Lactic Acid Film Surface for Promotion of In-Situ Gene Delivery," Biomacromolecules 8(6):1951-1957, Jun. 2007.

Kim, E.-M., et al., "Monitoring the Effect of PEGylation on Polyethylenimine in Vivo Using Nuclear Imaging Technique," Nuclear Medicine and Biology, 31(6):781-784, Aug. 2004.

Kong, K., et al., "Transfection Activity of Polyamidoamine Dendrimers Having Hydrophobic Amino Acid Residues in the Periphery," Bioconjugate Chemistry 16(1):208-214, Jan. 2005.

Kurisawa, M., et al., "Transfection Efficiency Increases by Incorporating Hydrophobic Monomer Units into Polymeric Gene Carriers," Journal of Controlled Release, 68(1):1-8, Jul. 31, 2000.

Lam, J.K.W., et al., "Phosphocoline-Polycation Diblock Copolymers as Synthetic Vectors for Gene Delivery," Journal of Controlled Release 100(2):293-312, Nov. 24, 2004.

Lomas, H., et al., "Biomimetic pH Sensitive Polymersomes for Efficient DNA Encapsulation and Delivery," Advanced Materials 19(23):4238-4243, Dec. 2007.

Neu, M., et al., "Recent Advances in Rational Gene Transfer Vector Design Based on Poly(ethylene imine) and its Derivatives," Journal of Gene Medicine 7(8):992-1009, Aug. 2005.

Ogris, M., et al., "PEGylated DNA/transferrin-PEI Complexes: Reduced Interaction with Blood Components, Extended Circulation in Blood and Potential for Systemic Gene Delivery," Gene Therapy 6(4):595-605, Apr. 1999.

Oupicky, D., et al., "Dna Delivery Systems Based on Complexes of DNA with Synthetic Polycations and Their Copolymers," Journal of Controlled Release 65(1-2):149-171, Mar. 1, 2000.

Scales, C.W., et al., "Corona-Stabilized Interpolyelectrolyte Complexes of SiRNA with Nonimmunogenic, Hydrophilic/Cationic Block Copolymers Prepared by Aqueous Raft Polymerization," Macromolecules 39(20):6871-6881, Oct. 3, 2006.

Takeda, N., et al., "Temperature-Responsive Polymeric Carriers Incorporating Hydrophobic Monomers for Effective Transfection in Small Doses," Journal of Controlled Release 95(2):343-355, Mar. 5, 2004.

Veron, L., et al., "Hydrolyzable p(DMAPEMA) Polymers for Gene Delivery," Macromolecular Bioscience 6(7):540-554, Jul. 14, 2006.

Yu, H., et al., "A Novel Amphiphilic Double-[60]Fullerene-Capped Triblock Copolymer," Macromolecules 38(23):9889-9893, Nov. 15, 2005.

Zhao, X, et al.,"Nanostructure of Polyplexes Formed Between Cationic Diblock Copolymer and Antisense Oligodeoxynucleotide and its Influence on Cell Transfection Efficiency," Biomacromolecules 8(11):3493-3502, Nov. 12, 2007.

\* cited by examiner

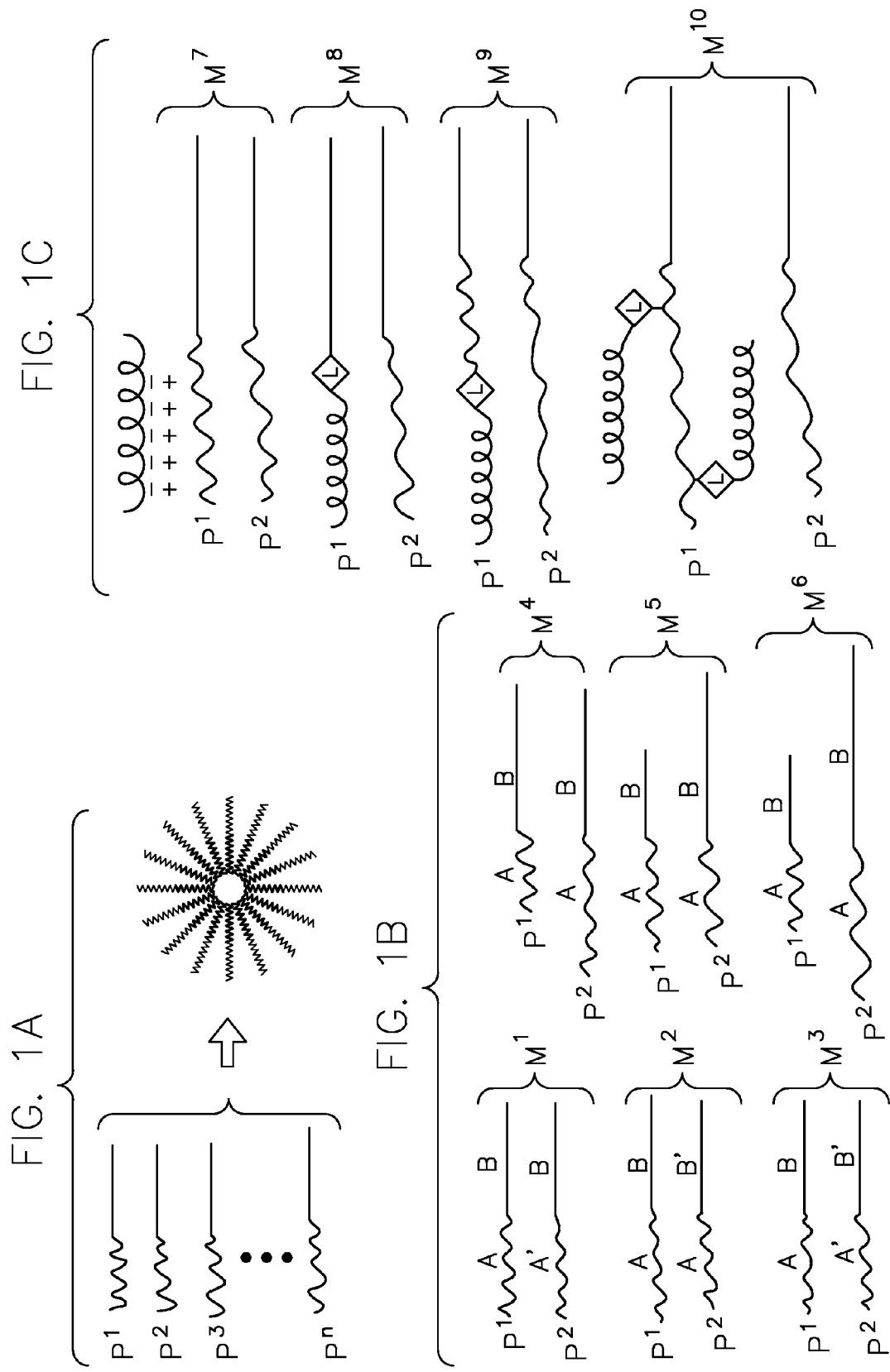

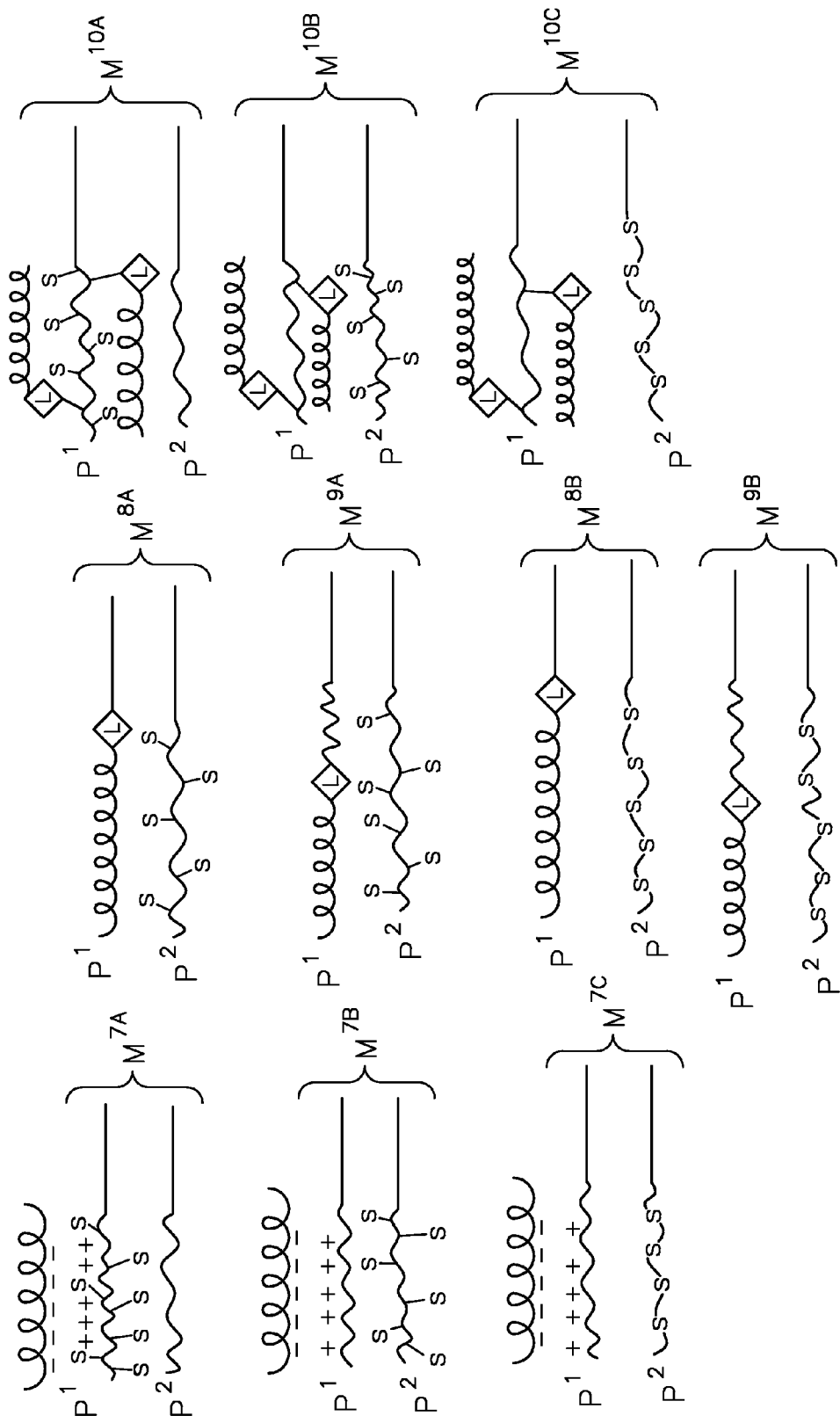

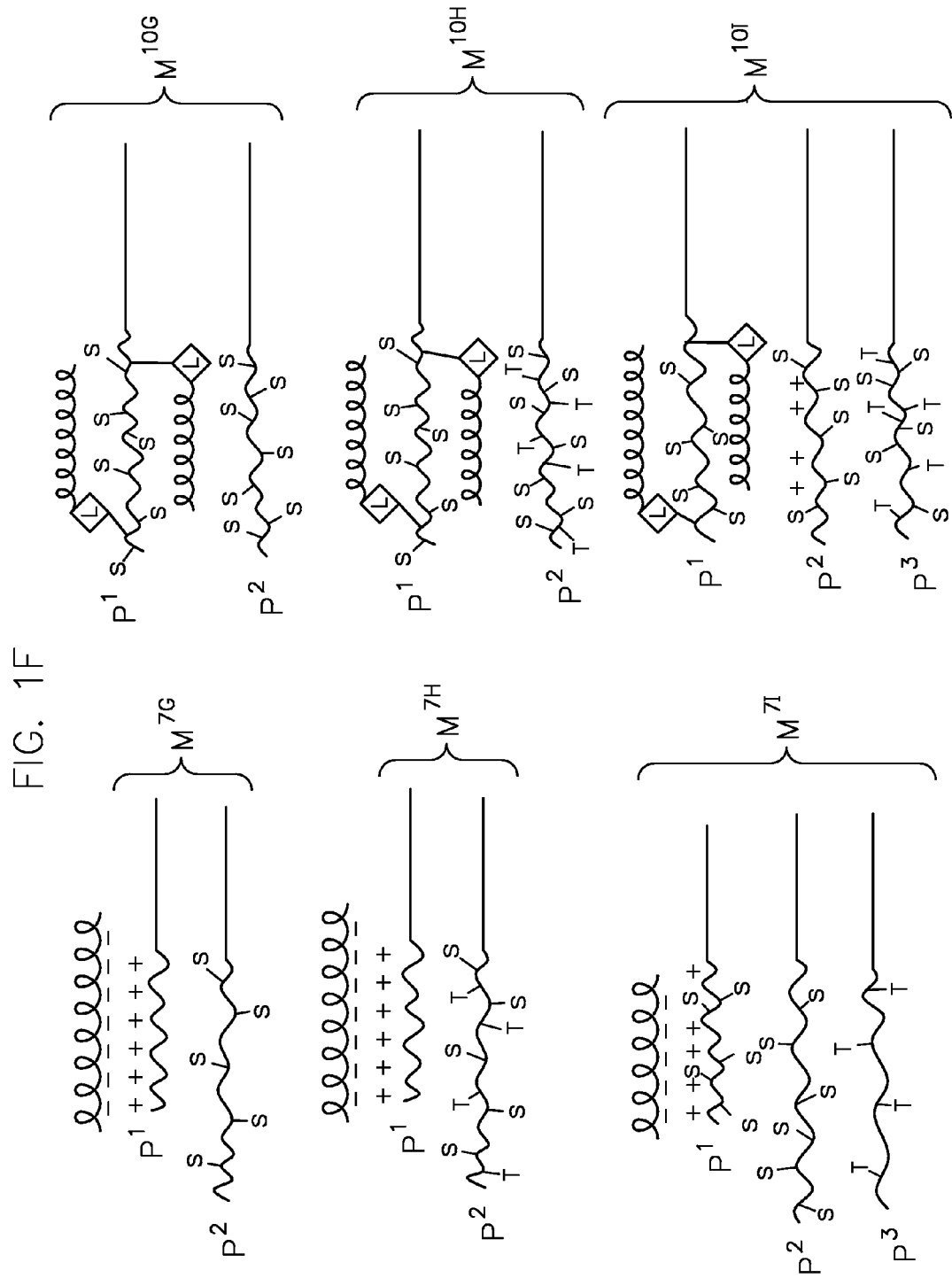

FIG. 3A
| POLYMER | FIRST BLOCK | | SECOND BLOCK | | | |
|---|---|---|---|---|---|---|
| | Mn (kDa) | PDI | Mn (kDa) | PDI | %BMA (mol) | %DMAEMA (mol) | %PAA (mol) |
| P7-PEGMA100 40kDa | 40.12 | 1.34 | 59.3 | 1.40 | 53 | 26 | 21 |
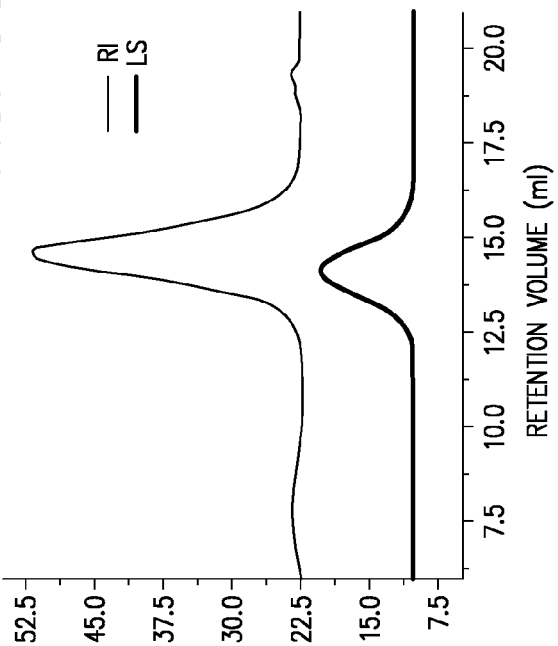
FIG. 3C
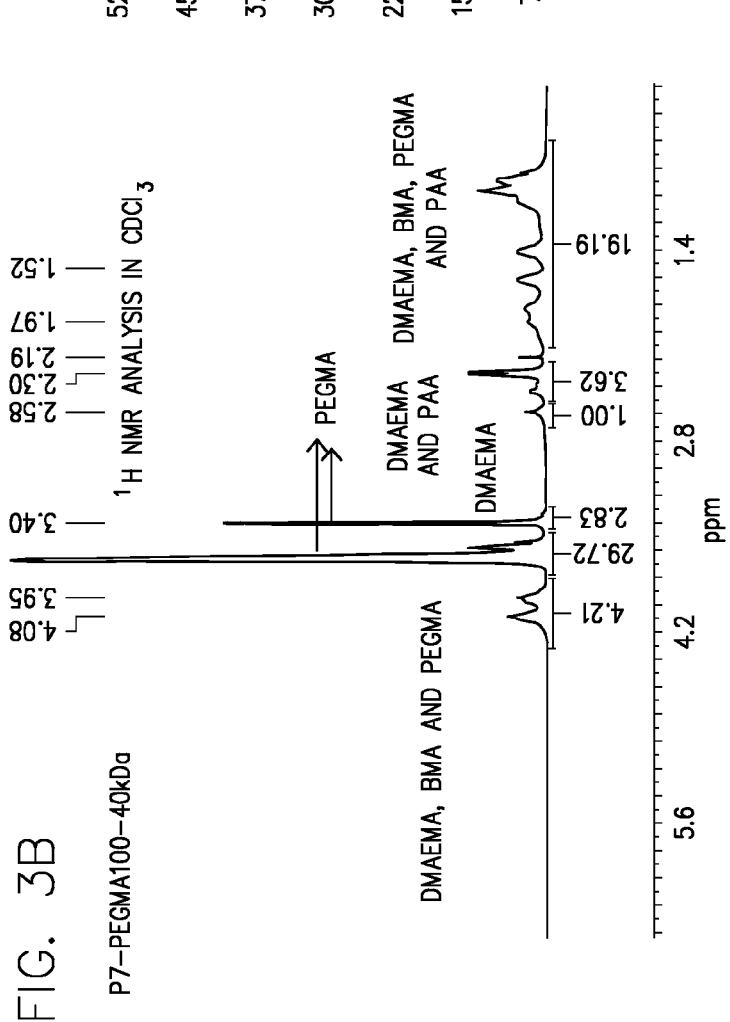
FIG. 3B
P7-PEGMA100-40kDa

FIG. 9

| Polymer | Polymer Dose (mg/kg) | | RNA Binding IC50 [P] ug/ml |
|---|---|---|---|
| | Non-toxic | Toxic | |
| [D]$_{10K}$-[B$_{50}$-P$_{25}$-D$_{25}$]$_{30K}$ (4.6) | <11.5 | 15 | 3.75 |
| [PEGMA]$_{18K}$-[B$_{50}$-P$_{25}$-D$_{25}$]$_{30K}$ (4.7) | >50 | >50 | No binding |
| Mixed micelles: (4.6)/(4.7) (%'s): | | | |
| 95%/5% | 11.5 | 15 | 5.0 |
| 90%/10% | 11.5 | 15 | 5.2 |
| 80%/20% | 11.5 | 15 | 6.0 |
| 50%/50% | 20 | 25 | 8.6 |
| 25%/75% | <50 | >50 | 16.0 | ically with respect to achieving intracellular delivery, with

HETEROGENEOUS POLYMERIC MICELLES FOR INTRACELLULAR DELIVERY

RELATED APPLICATIONS

This application claims priority to and the benefit of each of the following applications: U.S. Provisional Application No. 61/091,294 filed Aug. 22, 2008 entitled "Diblock Copolymer Micelles and Polynucleotide Complexes Thereof for Delivery into Cells"; U.S. Provisional Application No. 61/112,054 filed Nov. 6, 2008 entitled "Polymeric Carrier"; U.S. Provisional Application No. 61/112,048 filed Nov. 6, 2008 entitled "Micellic Assemblies"; U.S. Provisional Application No. 61/140,779, filed Dec. 24, 2008 entitled "Polymeric Carrier"; U.S. Provisional Application No. 61/140,774 filed Dec. 24, 2008 entitled "Micellic Assemblies"; U.S. Provisional Application No. 61/171,358 filed Apr. 21, 2009 entitled "Polymeric Carrier"; and U.S. Provisional Application No. 61/171,369 filed Apr. 21, 2009 entitled "Micellic Assemblies"; each of which applications are incorporated herein by reference.

STATEMENT OF JOINT RESEARCH AGREEMENT

The subject matter of the claimed invention was made as a result of activities undertaken within the scope of a joint research agreement, within the meaning of 35 U.S.C. §103(c)(3) and 37 C.F.R. §1.104(c)(4)(ii), by or on behalf of the University of Washington and PhaseRx, Inc. that was in effect on or before the claimed invention was made.

STATEMENT OF GOVERNMENT LICENSE RIGHTS

This invention was made with Government support under Grant Numbers NIH 1RO1EB002991 and 5 R01 EB02991-03 awarded by the National Institutes of Health. The Government has certain rights in the invention.

BACKGROUND

The instant inventions are generally related to compositions and methods for intracellular delivery of biomolecular agents such as polynucleotides, and more specifically, for intracellular delivery of such agents using polymeric micelles.

Polymeric micelles are known in the art for delivering therapeutics into cells. PCT Patent Application WO 2008/153940 (Hirt et al.) discloses vesicles prepared from amphiphilic segmented copolymers. Kataoka et al. (2005) ("Smart polymeric micelles as nanocarriers for oligosaccharides and siRNA delivery", Oxford University Press—Nucleic Acids Symposium Series, No. 49, pp. 17-18) disclose various approaches involving polyionic complexes. PCT Application WO 2008/004978 (Yang et al.) discloses homogeneous micelles adapted for delivery of small molecule therapeutics. U.S. Patent Application Publication No. 2005/0070721 (Bae et al.) discloses heterogeneous carriers adapted for delivery of hydrophobic small molecule therapeutics. U.S. Pat. No. 6,210,717 (Choi et al.) discloses heterogeneous carriers comprising polycation-b-polyesters and polysaccharide-conjugated polyesters for transport of nucleic acids into eukaryotic cells. PCT Patent Application WO 2009/004978 (Torchilin et al.) discloses heterogeneous carriers comprising cholesterol-conjugated small interfering ribonucleic acid (siRNA) and polyethyleneglycol-conjugated phosphatidylethanolamine for polynucleotide delivery.

Known approaches for delivering biomolecular agents using micelles have a variety of shortcomings.

Generally, for example, many such approaches are lacking or are inadequate with respect to desirable functionality, especially with respect to achieving intracellular delivery, with respect to delivery of specific classes of biomolecular agents such as polynucleotides, and/or with respect to achieving targeted delivery to specific cells of interest. For example, various known systems have not contemplated, are ineffective, or have other deficiencies for release of an agent from endosomes into the cytoplasm, after the agent enters the cell through endocytosis. Known systems are also lacking or inadequate for certain features important for delivering polynucleotides, such as providing for adequate association of the polynucleotide with the micelle, while avoiding potential toxicities and enzymatic degradation, and while maintaining robust micellic stability. As a non-limiting example, some known approaches include polycationic functionality for ionic association of negatively-charged polynucleic acids; however, if inadequately shielded, polycations can cause toxicity concerns in vivo (e.g., toxicities mediated by non-specific interactions with plasma proteins or circulating cells). Known approaches have incorporated polynucleotides by ionic association into the core of the micelle; however, such approaches can impact micelle stability. Although various known systems have contemplated targeting approaches for specifically-directed cellular uptake (e.g., via receptor-mediated endocytosis), these systems have been ineffective in integrating such functionality into micelles without compromising other required functionality.

Additionally, various known approaches are generally not sufficiently robust to incorporate multiple, complex functional features required for effective intracellular delivery of biomolecular agents such as polynucleotides. For example, many known carrier systems are formed from naturally-occurring moieties such as lipids or phospholipids (e.g., phosphatidylethanolamine), peptidic polymers (e.g., polyhistidine), or polysaccharides, which are typically more susceptible to biological degradation if inadequately protected, or formed from simple homopolymers (e.g., polyesters such as polylactic acid) which offer few design variations for incorporating multiple functional features, for optimization to enhance such features, or for tuning to tailor such features to specific applications of interest.

As a further shortcoming, known systems for intracellular delivery of biomolecular agents such as polynucleotides are not readily manufacturable. Efforts to achieve delivery vehicles which incorporate multiple functional features are hindered by complex and chemically difficult syntheses—e.g., involving multi-way chemical conjugations, which can be particularly difficult to realize in larger scale production.

Hence, there remains a substantial need in the art for improved compositions and methods for intracellular delivery of biomolecular agents such as polynucleotides, and especially, for improved intracellular delivery of such agents using polymeric micelles.

SUMMARY OF INVENTION

The present inventions provide, in various aspects more fully enumerated below, heterogeneous polymeric micelles, compositions comprising heterogeneous polymeric micelles, methods for preparing such micelles and such compositions, and various methods for using such micelles and such compositions. More particularly, preferred aspects of the inventions are directed to compositions comprising a heterogeneous polymeric micelle and an agent associated with the micelle. The agent can be a biomolecular agent such as a polynucleotide. The agent can preferably be a therapeutic agent, a diagnostic agent, or a research agent. Such composition can be a pharmaceutical composition, comprising a heterogeneous polymeric micelle, an agent associated with the micelle, and one or more pharmaceutically acceptable excipients.

Such compositions are preferably effective for (and can be used in a method for) intracellular delivery of an agent to a eukaryotic cell, such as a mammalian (e.g., human) cell. Such compositions are preferably effective for (and can be used in a method for) modulating the activity of an intracellular target (e.g., a target involved in gene expression of a cell, which can interact with a polynucleotide agent such as a small interfering ribonucleic acid (siRNA) in a cell). Compositions effective for intracellular delivery, and/or for modulating the activity of an intracellular target can preferably require multiple functional features or attributes, including for example a membrane-destabilizing activity (e.g., to release an agent from an endosome for intracellular delivery to the cytoplasm), a capability for associating an agent such as a polynucleotide (e.g., through ionic association or covalent coupling), and other functionalities such as shielding, targeting, stability-enhancing, crosslinking, formulation-enhancing, each of which is further described herein.

Heterogeneous polymeric micelles can advantageously affect such various desirable functional attributes and features through a combination of separate, singularly-prepared constituent polymers, which are formed into the heterogeneous (mixed) micellar assembly.

Generally, a heterogeneous polymeric micelle comprises two or more compositionally distinct polymers, including a first polymer and a second polymer compositionally distinct from the first polymer. At least one of the first or second polymers, and preferably each of the first and second polymers is a block copolymer comprising a hydrophilic block and a hydrophobic block. If only one polymer of the heterogeneous micelle (e.g., a first polymer) is a block copolymer, then the other polymer (e.g., a second polymer) is preferably a hydrophobic polymer, such as a hydrophobic homopolymer or a hydrophobic random copolymer. In each case, the heterogeneous micelle can comprise a hydrophobic block of a (e.g., first) block copolymer associated with a hydrophobic (e.g., block of a) second polymer—through hydrophobic interactions. Preferably the micelle is stable in aqueous medium, at a physiologically-relevant pH (e.g., pH 7.4). In some embodiments, the heterogeneous polymeric micelle comprises one or more additional compositionally distinct polymers, such as a third polymer which is compositionally distinct from each of the first polymer and the second polymer. Generally, each block of a block copolymer (e.g., of the first polymer and/or the second polymer) can be a homopolymer or a random copolymer, in each case linear or non-linear (e.g., branched), and in each case crosslinked or uncrosslinked, and can generally comprise one or more monomeric residues derived from polymerization of a polymerizable monomer (e.g., using controlled living radical polymerization approaches).

Accordingly, the heterogeneous polymeric micelles of the invention are exceedingly rich in potential diversity—including compositional diversity, architectural diversity and supramolecular diversity. In view of the extremely wide range of commercially available polymerizable monomers, each of the first and second polymer (include one or more blocks thereof) can have an enormous variety of chemical compositions—and correspondingly a great variety of chemical properties or characteristics, such as relative hydrophobicity or hydrophilicity, relative ionic character (e.g., anionic, cationic, neutral (non-charged), zwitterionic), a presence or absence of reactive functional groups (e.g., conjugatable moieties), a presence or absence of environmentally-sensitive properties (e.g., thermal sensitivity, pH sensitivity, chemical sensitivity, electromagnetic sensitivity) and associated or derivative physical properties, such as solubility, density, viscosity, thermal stability, among others.

Heterogeneous polymeric micelles also offer substantial architectural diversity which compliments and is synergistic with such compositional diversity. The first and second compositionally distinct polymers can each be multiblock copolymers including various numbers of blocks (e.g., two or more, three or more, four or more, five or more blocks), and various total polymer lengths or molecular weights, and each copolymer can have independently selected variations in relative block lengths or molecular weights, relative arrangement of blocks (e.g., of blocks with particular chemical properties or characteristics), are relative block structures (e.g., straight-chain, branched-chain, or involving brushes, stars, or other architectures.).

Significantly, the value of such architectural and underlying compositional diversities is further enhanced by supramolecular diversity realized and singularly advantaged by heterogeneous polymeric micelles. A broad range of supramolecular structures and properties can be achieved using compositionally distinct polymers—especially for complex systems requiring multiple simultaneous functionalities. For example, a particular first (set of) desired attribute(s) of a composition can be imparted through a first polymer, whereas a different second (set of) desired attribute(s) of the composition can be provided through another compositionally distinct second polymer, and if desired a further different additional (set(s) of) desired attribute(s) of the composition can be provided through further compositionally distinct third polymer(s), etc. Hence, the supramolecular design of the heterogeneous polymeric micelle includes a further independent freedom of design choice which can be applied for selection and optimization of supramolecular structure—e.g., with respect to total aggregation number, relative aggregation numbers (e.g., ratio of each type of the first, second, third, etc. compositionally distinct polymers included with heterogeneous micelle), particle size, solubility (e.g., aqueous solubility), stability, formulatability, biocompatibility, the nature and extent of association with an agent to be delivered, and relative balance of desirable functional features or physical location or orientation of certain functional features within the supramolecular structure.

Advantageously, the present inventions apply the compositional, architectural and supramolecular design flexibility and control afforded through heterogeneous polymeric micelles to systems for intracellular delivery of agents, especially biomolecular agents such as polynucleotides. For example, the heterogeneous polymeric micelles—or certain blocks of such polymers, can include a membrane-destabilizing polymer, such as an environmentally-sensitive (e.g., pH sensitive) membrane-destabilizing polymer, which following endocytosis can effect release of an agent from an endosomal membrane into the intracellular cytoplasm.

One or more of the constituent polymers of the heterogeneous polymeric micelles—or certain blocks of such polymers, can associate agent(s) such as polynucleotides. For example, polynucleotides or other agent(s) can be associated through ionic interactions with one or more of the constituent polymers, and/or through covalent conjugation to one or more of the constituent polymers. Covalent conjugation can be achieved, for example, through a monomeric residue having a conjugatable species (i.e., reactive functional group moiety). Some agents such as polynucleotides which are hydrophilic can be alternatively associated by covalent conjugation to an end of one of the polymers, allowing such agent (e.g., polynucleotide) to essentially constitute and function as a hydrophilic block of the end-conjugated polymer.

Further, one or more of the constituent polymers of the heterogeneous polymeric micelles—or certain blocks of such polymers, can provide various shielding (e.g., modulating, moderating or protecting) attributes. For example, shielding can be effected by incorporating species or moieties effective for steric shielding, for enhancing stability against metabolism (e.g., enzymatic digestion), for mediating potential toxicities, for enhancing pharmacokinetics, for enhancing a desired biodistribution, etc.); such shielding functionality can be of substantial importance for delivery of biomolecular agents such as polynucleotides.

One or more of the constituent polymers of the heterogeneous polymeric micelles—or certain blocks of such polymers, can provide targeting functionality, for example, allowing for an agent such as a polynucleotide to be specifically directed to a particular cell type of interest, for example by covalent conjugation of one or more targeting moieties—including moieties having various specificity—such as polysaccharides or oligosaccharides or specific targeting ligands—and effective for receptor-mediated endocytosis.

Importantly, one or more of the constituent polymers of the heterogeneous polymeric micelles—or certain blocks of such polymers, can contribute to effecting and maintaining micellic stability, or other important micellic parameters or properties. For example, one or more of the constituent polymers of the heterogeneous polymeric micelles—or certain blocks of such polymers can have functionality for properties or attributions of the micelle itself—e.g., stability size, shape, aggregation number, intramicelle spatial considerations, intramicelle steric considerations, among others.

One or more of the constituent polymers of the heterogeneous polymeric micelles—or certain blocks of such polymers, can be a diluent polymer having little or no functionality.

One or more of the constituent polymers of the heterogeneous polymeric micelles—or certain blocks of such polymers, can be a crosslinking polymer or polymer block—effectively allowing for covalent coupling of some or all of the constituent polymers of the heterogeneous micelle. One or more of the constituent polymers of the heterogeneous polymeric micelles—or certain blocks of such polymers, can have functionality for enhancing the biocompatibility of the heterogeneous polymeric micelle (e.g., with other co-administered agents, or for specific applications or environments).

One or more of the constituent polymers of the heterogeneous polymeric micelles—or certain blocks of such polymers, can be a formulation-enhancing polymer having functionality for formulating the composition comprising the heterogeneous polymeric micelle and an associated agent (such as a polynucleotide) into, for example, a pharmaceutical composition or medicament (e.g., for therapeutic use), a diagnostic composition (e.g., for diagnostic use) or a research reagent composition (e.g., for use as a research reagent).

Advantageously, despite the multifunctional nature and potential inherent complexity associated therewith, heterogeneous polymeric micelles are readily manufacturable. This can be realized—even for relatively complex systems, because required functional attributes are separately effected on the two or more different polymers—allowing for more direct, less complicated manufacturability of each singular constituent polymer. Each of the two or more compositionally distinct polymers can be independently prepared (including at large scale) using well-known polymerization processes. Moreover, as described herein, formation of the heterogeneous polymeric micelle from constituent polymers can be readily achieved, based on the protocols described herein.

Therefore, it can be appreciated that the present inventions overcome many shortcomings of the prior known approaches—especially for incorporating multiple desirable functional features, for optimization to enhance such features, or for tuning to tailor such features to specific applications of interest.

The present inventions are summarized with more particularity in the following paragraphs, and described in greater detail throughout the specification.

In a first aspect therefore, the invention is directed to a heterogeneous polymeric micelle. The heterogeneous polymeric micelle can comprise a first polymer, the first polymer being a block copolymer comprising a hydrophilic block and a hydrophobic block, and a second polymer compositionally distinct from the first polymer. The second polymer can be a hydrophobic polymer or can be a block copolymer comprising a hydrophobic block. The hydrophobic second polymer or the hydrophobic block of the second polymer can associate with the hydrophobic block of the first polymer. Preferably, the second polymer is a block copolymer comprising a hydrophilic block and a hydrophobic block. Preferably, the micelle is stable in an aqueous medium at pH 7.4.

In a first general embodiment of the first aspect of the invention, at least one of the first polymer or the second polymer is or comprises (e.g., as a constituent block thereof) a pH-dependent, membrane-destabilizing polymer.

In a second general embodiment of the first aspect of the invention, the second polymer is a block copolymer comprising a hydrophilic block and a hydrophobic block, and the hydrophobic block of at least one of the first polymer or the second polymer comprises a plurality of hydrophobic monomeric residues and a plurality of anionic monomeric residues.

In a third general embodiment of the first aspect of the invention, the heterogeneous polymeric micelle is prepared by the method of the third aspect of the invention.

In a second aspect, the invention is directed to compositions comprising a heterogeneous polymeric micelle and an agent associated with the micelle. The agent can be a biomolecular agent, such as a polynucleotide. The agent can be preferably selected from a therapeutic agent, a diagnostic agent and a research reagent. Generally, the heterogeneous polymeric micelle can comprise a first polymer, the first polymer being a block copolymer comprising a hydrophilic block and a hydrophobic block, and a second polymer compositionally distinct from the first polymer. The second polymer can be a hydrophobic polymer or can be a block copolymer comprising a hydrophobic block. The hydrophobic second polymer or the hydrophobic block of the second polymer can associate with the hydrophobic block of the first polymer. Preferably, the second polymer is a block copolymer comprising a hydrophilic block and a hydrophobic block. Preferably, the micelle is stable in an aqueous medium at pH 7.4

In a first general embodiment of the second aspect of the invention, at least one of the first polymer or the second polymer is or comprises (e.g., as a constituent block thereof) a pH-dependent, membrane-destabilizing polymer. Preferably, the agent is a polynucleotide. Preferably, the second polymer is a block copolymer comprising a hydrophilic block and a hydrophobic block. Preferably, the hydrophobic block of the first polymer and the hydrophobic block of the second polymer each comprise a plurality of hydrophobic monomeric residues.

In a second general embodiment of the second aspect of the invention, the second polymer is a block copolymer comprising a hydrophilic block and a hydrophobic block, and the hydrophobic block of at least one of the first polymer or the second polymer comprises a plurality of hydrophobic monomeric residues and a plurality of anionic monomeric residues. Preferably, the agent is a polynucleotide.

In a third general embodiment of the second aspect of the invention, the composition comprises the heterogeneous polymeric micelle and a polynucleotide associated with the micelle—through (non-covalent) ionic interactions. The hydrophilic block of the first polymer comprises a plurality of cationic monomeric residues in ionic association with the polynucleotide. The second polymer is a block copolymer comprising a hydrophilic block and a hydrophobic block. At least one block of (i) the hydrophilic block or (ii) the hydrophobic block of the first polymer, or (iii) the hydrophilic block or (iv) the hydrophobic block of the second polymer is a random copolymer block comprising two or more compositionally distinct monomeric residues. Preferably, two or more, three or more, or each of such blocks (i), (ii), (iii) or (iv), is a random copolymer. Preferably, the hydrophilic block of the second polymer comprises a plurality of neutral (non-charged) hydrophilic monomeric residues. Preferably, the hydrophobic block of the first polymer and the hydrophobic block of the second polymer each comprise a plurality of hydrophobic monomeric residues.

In a fourth general embodiment of the second aspect of the invention, the composition comprises the heterogeneous polymeric micelle and a polynucleotide associated with the micelle—through covalent coupling to the first polymer. The polynucleotide is coupled to the first polymer such that the polynucleotide (i) is the hydrophilic block or (ii) is a constituent moiety of the hydrophilic block of the first polymer. (e.g., through an orientation involving end-coupling of the polynucleotide to (i) the hydrophobic block of the first polymer or (ii) a hydrophilic block of the first polymer. Preferably, the second polymer is a block copolymer comprising a hydrophilic block and a hydrophobic block. Preferably, the hydrophobic block of the first polymer and the hydrophobic block of the second polymer each comprise a plurality of hydrophobic monomeric residues.

In a fifth general embodiment of the second aspect of the invention, the composition comprises the heterogeneous polymeric micelle and a polynucleotide associated with the micelle—through covalent coupling to the first polymer. The polynucleotide is coupled to the first polymer to form a polymer bioconjugate. The hydrophilic block of the first polymer comprises one or more monomeric residues (e.g., having a conjugating species) coupled to the polynucleotide through a linking moiety. The one or more monomeric residues can have a conjugating species (e.g., as a pendant moiety of the monomeric residue) coupled to the polynucleotide through a linking moiety. Preferably, a plurality of polynucleotides are covalently coupled to the first polymer through a corresponding plurality of monomeric residues. Preferably, the second polymer is a block copolymer comprising a hydrophilic block and a hydrophobic block. Preferably, the hydrophobic block of the first polymer and the hydrophobic block of the second polymer each comprise a plurality of hydrophobic monomeric residues.

In a third aspect, the invention is directed to methods for preparing heterogeneous polymeric micelles. The invention is preferably directed to methods for preparing heterogeneous polymeric micelles of the first aspect of the invention, including all general embodiments thereof, and all subembodiments thereof.

In a fourth aspect, the invention is directed to methods for preparing compositions comprising a heterogeneous polymeric micelle and an agent associated with the micelle. The agent can be a biomolecular agent, such as a polynucleotide. The agent can be preferably selected from a therapeutic agent, a diagnostic agent and a research reagent. Such invention is preferably directed to methods for preparing compositions of the second aspect of the invention, including all general embodiments thereof, and all subembodiments thereof.

In a fifth aspect, the invention is directed to use of a heterogeneous polymeric micelle in the manufacture of a medicament. Such invention is preferably directed to use of a heterogeneous polymeric micelle of the first aspect of the invention, including all general embodiments thereof, and all subembodiments thereof.

In a sixth aspect, the invention is directed to use of a composition in the manufacture of a medicament, the composition comprising a heterogeneous polymeric micelle and an agent associated with the micelle. The agent can be a biomolecular agent, such as a polynucleotide. The agent can be preferably selected from a therapeutic agent, a diagnostic agent and a research reagent. Such invention is preferably directed to manufacture of a medicament comprising the compositions of the second aspect of the invention, including all general embodiments thereof, and all subembodiments thereof.

In a seventh aspect, the invention is directed to a method for intracellular delivery of an agent. The agent can be a biomolecular agent, such as a polynucleotide. The agent can be preferably selected from a therapeutic agent, a diagnostic agent and a research reagent. Such invention is preferably directed to such method where the method involves use of a composition of the second aspect of the invention, including all general embodiments thereof, and all subembodiments thereof.

In an eighth aspect, the invention is directed to a method for modulating the activity of an intracellular target in a cell. Such invention is preferably directed to such method where the method involves use of a composition of the second aspect of the invention, including all general embodiments thereof, and all subembodiments thereof.

As a general preference, for each of the first aspect, second aspect, third aspect, fourth aspect, fifth aspect, sixth aspect, seventh aspect and eighth aspect of the invention, including each general embodiment thereof, the various inventions can further comprise one or more features independently selected from:

(a) the hydrophobic block of the first polymer, and optionally and preferably also the hydrophobic block of the second polymer, can be a pH-dependent membrane destabilizing polymer;

(b) the hydrophobic block of the first polymer, and optionally and preferably also the hydrophobic block of the second polymer, can comprise a plurality of hydrophobic monomeric residues and a plurality of anionic monomeric residues (and optionally can further comprise a plurality of cationic monomeric residues);

(c) the hydrophilic block of at least one (or both) of the first polymer or the second polymer can comprise a plurality of neutral hydrophilic monomeric residues;

(d) each of the first polymer and the second polymer comprise monomeric residues derived from a polymerizable monomer (preferably an ethlenically-unsaturated polymerizable monomer (e.g., an acrylic monomer or a vinylic monomer));

(e) each of the first polymer and the second polymer are non-peptidic polymers.

(f) each of the first polymer and the second polymer are non-lipidic.

(g) each of the first polymer and the second polymer are non-saccharide polymers (h) the first polymer is covalently crosslinked to the second polymer, whereby the polymeric micelle is a crosslinked polymeric micelle;

(i) the hydrophilic block of the second polymer is compositionally distinct from the hydrophilic block of the first polymer;

(j) the hydrophobic block of the second polymer has substantially the same composition as the hydrophobic block of the first polymer;

(k) the agent is a polynucleotide, and the polynucleotide is preferably an interfering RNA (l) the heterogeneous polymeric micelle further comprises a shielding moiety; and/or (m) the heterogeneous polymeric micelle further comprises a targeting moiety.

The present invention is directed as well to other aspects, in various embodiments, as will be appreciated by a person of ordinary skill in the art based on the teaching provided herein.

Various features of the invention, including features defining each of the various aspects of the invention, including general and preferred embodiments thereof, can be used in various combinations and permutations with other features of the invention. Features and advantages are described herein, and will be apparent from the following Detailed Description.

BRIEF DESCRIPTION OF DRAWINGS

FIG. 1A through 1F are schematic representations depicting heterogeneous polymeric micelles formed from two or more compositionally distinct block copolymers, $P^1, P^2 \ldots P^n$ (FIG. 1A), including various embodiments having differences in chemical composition or architectural structure of such block copolymers (FIG. 1B), and schematic representations depicting compositions comprising such heterogeneous micelles and polynucleotides associated therewith (FIG. 1C), including embodiments involving various approaches for incorporating shielding functionality into such compositions (FIG. 1D), embodiments involving various approaches for incorporating targeting functionality into such compositions (FIG. 1E), and embodiments involving preferred approaches for such compositions, including preferred approaches for integration of shielding and/or targeting functionality (FIG. 1F).

FIG. 3A through 3C show data summarizing characteristics and properties of polymer 4.8, a representative [PEGMA]-[DMAEMA/PAA/BMA] block copolymer, including a table reporting number-average molecular weight, Mn, and polydispersity index (PDI) for the first block [PEGMA] and the second block [DMAEMA/PAA/BMA], as well as the relative composition of monomeric residues of the second block (FIG. 3A), the 1H NMR data for such polymer (FIG. 3B), and gel permeation chromatography (GPC) data for such polymer, including traces from refractive index (RI) and light scattering (LS) detectors (FIG. 3C).

FIG. 9 is a table summarizing relative toxicity and polynucleotide-binding properties for a homogeneous micelle consisting essentially of a singular block copolymer 4.6 having a DMAEMA hydrophilic block, another homogeneous micelle consisting essentially of a singular block copolymer 4.7 having a PEGMA hydrophilic block (and substantially the same hydrophobic block as polymer 4.6), as well as for various heterogeneous micelles formed with different relative ratios of polymer 4.6 and polymer 4.7: M3.1 (95%/5%), M3.2 (90%/10%), M3.3 (80%/20%), M3.4 (50%/50%), and M3.5 (25%/75%).

Figure 1E:
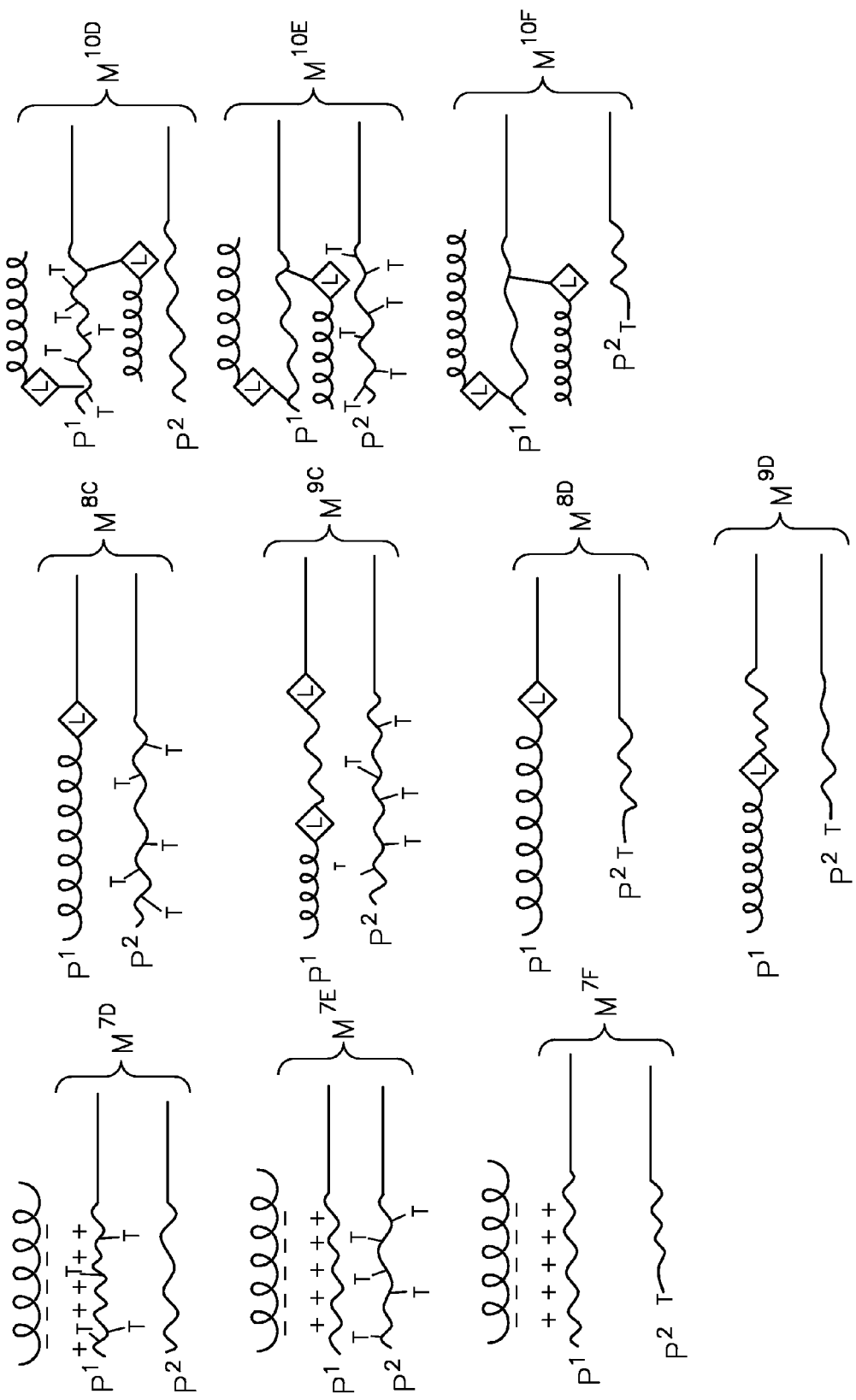

Various aspects of the figures are described in further detail below, in connection with the Detailed Description of the Invention.

DETAILED DESCRIPTION OF INVENTION

Various aspects of the present invention involve a heterogeneous polymeric micelle which comprises two or more compositionally distinct polymers. Preferred aspects of the invention are directed to compositions comprising heterogeneous polymeric micelle and an agent associated with the micelle. The agent can be a biomolecular agent such as a polynucleotide. The agent can preferably be a therapeutic agent, a diagnostic agent, or a research agent.

As described in the Summary of the Invention, and as more fully elaborated in the following detailed description of the inventions, heterogeneous polymeric micelles of the invention have substantial diversity—including compositional diversity, architectural diversity and supramolecular diversity. The present inventions apply the compositional, architectural and supramolecular design flexibility and control afforded through heterogeneous polymeric micelles to systems for intracellular delivery of agents, especially biomolecular agents such as polynucleotides. Significantly, this approach allows for incorporation of multiple desirable attributes and functional features into an intracellular delivery system.

For example, one or more polymers of the heterogeneous polymeric micelles—such as the first polymer or the second polymer, or certain blocks of such polymers, can include a membrane-destabilizing polymer, such as an environmentally-sensitive (e.g., pH sensitive) membrane-destabilizing polymer, which following endocytosis can effect release of an agent from an endosomal membrane into the intracellular cytoplasm. One or more of the constituent polymers of the heterogeneous polymeric micelles—or certain blocks of such polymers, can associate agent(s) such as polynucleotides, through ionic interactions with one or more of the constituent polymers, and/or through covalent conjugation to one or more of the constituent polymers. Further, one or more of the constituent polymers of the heterogeneous polymeric micelles—or certain blocks of such polymers, can provide further various desirable functional attributes or features, in various permutation and combinations, such as without limitation: shielding (e.g., modulating, moderating or protecting functionality, such as for steric purposes, enhancing agent stability, mediating potential toxicities, enhancing pharmacokinetics, enhancing desired biodistribution); targeting functionality (e.g., allowing for an agent such as a polynucleotide to be specifically directed to a particular cell type of interest); enhancing or maintaining micellic stability, or other important micellic parameters or properties; a crosslinking functionality (allowing for covalent coupling of some or substantially each of the constituent polymers of the heterogeneous micelle), enhancing the biocompatibility of the heterogeneous polymeric micelle (e.g., with other co-administered agents, or for specific applications or environments); formulating the composition; or a diluent polymer.

Moreover, heterogeneous polymeric micelles provide for design flexibility which enables optimization to enhance such attributes and features. Such design flexibility also enables a capability to tune or tailor such attributes and features to specific applications of interest. Significantly, such heterogeneous polymeric micelles can achieve multifunctional attributes and features through a combination of separate, singularly-prepared constituent polymers, which are then assembled into the heterogeneous micellic assembly. As a result, manufacturability is generally enhanced since each constituent polymer can be prepared more directly, with less complicated synthesis (e.g., as compared to homogeneous micelles incorporating, if possible, the same range of attributes and features into a singular constituent polymer).

Heterogeneous Polymeric Micelles—General Structure

With reference to FIG. 1A, a heterogeneous polymeric micelle comprises two or more compositionally distinct polymers, including a first polymer, $P^1$, and a second polymer, $P^2$, compositionally distinct from the first polymer $P^1$. The heterogeneous micelle may optionally include one or more additional compositionally distinct polymers, such as a third polymer, a fourth polymer, a fifth polymer or a sixth polymer, a seventh polymer, or further additional polymers, ad infinitum, generally represented by $P^n$, each of which additional polymers is compositionally distinct from each of the first polymer and the second polymer, and from each other. The number of compositionally distinct polymers, $P^1, P^2, \ldots P^n$, can therefore in some embodiments be three or more, four or more, five or more, six or more, seven or more, and can generally range from 2 to about 20, preferably from about 2 to about 10, preferably from 2 to 7, or alternatively, can generally range from 3 to about 20, preferably from about 3 to about 10, preferably from 3 to 7.

At least one of the first polymer or the second polymer, and preferably each of the first and second polymers is a block copolymer comprising a hydrophilic block and a hydrophobic block. (As depicted in FIGS. 1A through 1F, hydrophilic blocks are generally indicated as an irregular-wavy segment, "~~~~", whereas hydrophobic blocks are generally indicated as a straight-line segment, "------"). If only one polymer of the heterogeneous micelle (e.g., a first polymer) is a block copolymer, then the other polymer (e.g., a second polymer) is preferably a hydrophobic polymer, such as a hydrophobic homopolymer or a hydrophobic random copolymer. In each case, the heterogeneous micelle can comprise a hydrophobic block of a (e.g., first) block copolymer associated with a hydrophobic (e.g., block of a) second polymer—through hydrophobic interactions. Generally, each block of a block copolymer (e.g., of the first polymer, the second polymer, etc.) can be a homopolymer or a random copolymer. In each case, a block of a block copolymer can linear or non-linear (e.g., branched). In each case, a block of a block copolymer can be crosslinked or uncrosslinked. If crosslinked, the first and second polymers are preferably crosslinked through a monomeric residue (e.g., having crosslinkable functional groups) included within their respective hydrophobic blocks. In each case, a block of a block copolymer comprises one or more monomeric residues derived from polymerization of a polymerizable monomer (e.g., using controlled living radical polymerization approaches).

A block copolymer constituent of the heterogeneous polymeric micelle can be a diblock copolymer or a higher-ordered block copolymer. For example, each constituent block copolymer can be an independently selected multiblock copolymer comprising two or more blocks, or three or more blocks, or four or more blocks, or five or more blocks. In some embodiments, a first constituent block polymer can have a different number of blocks than a second constituent block copolymer. For example, a first polymer can be a triblock copolymer, and a second block can be a diblock copolymer or a tetrablock copolymer; and vice-versa. In each case, at least two block copolymer constituents of the heterogeneous polymeric micelle and preferably each block copolymer constituents can comprise at least one hydrophilic block and at least one hydrophobic block.

Generally, compositionally distinct polymers (e.g., a second polymer compositionally distinct from a first polymer) have an identifiable compositional difference other than a difference in polydispersity inherent from a polymerization process.

Generally, a compositionally distinct (e.g., second) polymer can comprise one or more monomeric residues which are different from (i.e., have a difference in chemical composition than) the monomeric residues of the other (e.g., first) polymer. Alternatively, compositionally distinct polymers (e.g., a first polymer and a second polymer) can comprise the same type of two or more monomeric residues (residues having the same chemical composition), but with differences in relative ratio of such two or more monomeric residues as compared between polymers. Referring to FIG. 1B, for example, heterogeneous polymeric micelles $M^1$, $M^2$, $M^3$, $M^4$, $M^5$, $M^6$ can each comprise a first polymer $P^1$, and a second polymer $P^2$, each having a hydrophilic block (generally designated as A or A') and a hydrophobic block (generally designated as B or B'). As depicted for example for micelle $M^1$, the hydrophilic block A' of the second polymer can be compositionally distinct from the hydrophilic block A of the first polymer. Alternatively, as shown for example for micelle $M^2$, the hydrophobic block B' of the second polymer can be compositionally distinct from the hydrophobic block B of the first polymer. In some embodiments (e.g., micelle $M^1$), the hydrophilic block A' of the second polymer is compositionally distinct from the hydrophilic block A of the first polymer, and the hydrophobic block B of the second polymer has substantially the same composition as the hydrophobic block B of the first polymer. In some embodiments, (e.g., micelle $M^2$), the hydrophilic block A of the second polymer has substantially the same composition as the hydrophilic block A of the first polymer, and the hydrophobic block B' of the second polymer is compositionally distinct from the hydrophobic block B of the first polymer. In alternative embodiments (e.g., micelle $M^3$), the hydrophilic block A' of the second polymer is compositionally distinct from the hydrophilic block A of the first polymer, and the hydrophobic block B' of the second polymer is compositionally distinct from the hydrophobic block B of the first polymer.

Generally, a compositionally distinct (e.g., second) polymer can have a polymeric architecture which differs from the polymeric architecture of the other (e.g., first) polymer. For example, the first and second block copolymers can each have blocks of varying molecular weights relative to corresponding blocks of the other copolymers. Referring further to FIG. 1B, for example, a heterogeneous polymeric micelle $M^4$ can have a first polymer with a hydrophilic block A of lower molecular weight than the hydrophilic block A of the second polymer, and with the hydrophobic block B of the first polymer being substantially the same molecular weight as the hydrophobic block B of the second polymer. Conversely, as depicted by micelle $M^5$, the hydrophilic block A of the first polymer and the second polymer can have substantially the same molecular weight, and the first polymer can have a hydrophobic block B of lower molecular weight than the hydrophobia block B of the second polymer. In another embodiment, as depicted in micelle $M^6$ for example, the hydrophilic block A of the first polymer and the hydrophobic block B of the first polymer can each have a lower molecular weight than the corresponding hydrophilic block A and hydrophobic block B of the second polymer. In preferred embodiments, the ratio of number-average molecular weight of the hydrophilic block to the hydrophobic block for a first polymer, $(M_n^{hydrophilic}:M_n^{hydrophobic})^1$, can vary by at least 0.1 from the corresponding ratio of number-average molecular weight of the hydrophilic block to the hydrophobic block for the second polymer, $(M_n^{hydrophilic}:M_n^{hydrophobic})^2$. Said ratios can alternatively vary by at least 0.15, at least 0.2, at least 0.25 or at least 0.3. As another example, an alternative architecture can generally include first and second block copolymers that have a difference in total polymer molecular weight—e.g., with different relative ratios of block molecular weights (e.g., micelle $M^4$, micelle $M^5$) or with substantially the same relative ratios of block molecular weights (e.g., micelle $M^6$). In some preferred embodiments, the total number-average molecular weight, Mn, of the first polymer can vary by at least 10% from the total number-average molecular weight, Mn, of the second polymer. Said total molecular weights can alternatively vary by at least 15%, at least 20%, at least 25% or at least 30%, and in some embodiments, can vary by at least about 50%, at least about 70%, at least about 100%, and in some embodiments can vary by at least about 150% or at least about 200%. In each such case, the compositionally distinct polymers having differences in polymeric architecture can have the same or different constituent monomeric residues as described in the preceding paragraphs.

Generally, the ratio of number-average molecular weight, $M_n$, of the hydrophilic block to the hydrophobic block for a constituent polymer of the heterogeneous polymeric micelle can preferably range from about 2:1 to about 1:9, preferably from about 3:2 to about 1:7, preferably from about 3:2 to about 1:5, preferably from about 3:2 to about 1:4, preferably from about 1:1 to about 1:5, preferably from about 1:1 to about 1:4, preferably from about 1:1 to about 1:3 and in some embodiments from about 1:1 to about 1:2.

Generally, a first constituent polymer can have a polymeric architecture which is the same the second constituent polymer, if such first and second polymer are compositionally distinct on another basis (e.g., based on differences in chemical composition of respective one or more monomeric residues).

Generally, a micelle refers to a particle defined by aggregation of constituent amphiphilic polymers (e.g., the first polymer and/or the second polymer). A micelle can generally comprise a hydrophobic core and a hydrophilic shell. The core region of the micelle can comprise the hydrophobic block of constituent block copolymers, which can associate at least partially, predominantly or substantially through hydrophobic interactions. Preferably, a hydrophobic block of a first polymer and a hydrophobic block of a second polymer associate (e.g, through such hydrophobic interactions) to form a micelle which is stable in a medium of interest.

Preferably, a heterogeneous polymeric micelle is stable in an aqueous medium at physiological pH (e.g. pH 7.4), and preferably at a physiologically relevant temperature (e.g., 37° C.). Preferably, a stable micelle does not substantially disassociate in its environment. Micelle stability can be demonstrated, for example, by substantial retention of one or more physical or chemical characteristics, such as hydrodynamic particle size or critical micelle concentration (CMC). For example, as a measure of relative stability in different environments, a polymeric micelle in an alternative environment can preferably have a hydrodynamic particle size within 60%, 50%, 40%, 30%, 20%, or 10% of the corresponding hydrodynamic particle size in a baseline environment—e.g., an aqueous solution at a pH of 7.4, preferably at 37° C. As another example, a polymeric micelle in an alternative environment can preferably have a critical micelle concentration within 60%, 50%, 40%, 30%, 20% or 10% of the corresponding critical micelle concentration in a baseline environment—e.g., aqueous solution at a pH of 7.4, preferably at 37° C.

Generally, unless otherwise stated or understood from context, a normal or physiological pH ranges from about 7.2 to about 7.4.

Membrane Destabilizing Polymer

Generally, one or more of the first polymer or second polymer of the heterogeneous polymeric micelle can be or can consist essentially of or can comprise (including for example as regions or segments, such as a block of a block copolymer) a membrane destabilizing polymer, and preferably a pH-dependent membrane destabilizing polymer. In preferred embodiments, the hydrophobic block of the first polymer and/or the hydrophobic block of the second polymer can be or can consist essentially of or can comprise a membrane destabilizing polymer, and preferably a pH-dependent membrane destabilizing polymer. The first or second polymer or a hydrophobic block thereof, can preferably be or can consist essentially of or can comprise at least one membrane disruptive polymer.

Preferred polymers provided herein can be a cellular membrane destabilizing or disruptive polymer (i.e., is destabilizing or disruptive of a cellular membrane), such as, by way of non-limiting example, an extracellular membrane, or a membrane of an intracellular membrane, a vesicle, an organelle, an endosome, a liposome, or a red blood cell. Preferably, in certain instances, wherein a polymer described herein is in contact with a cellular membrane, it destabilizes or disrupts the membrane and provides a mass-transfer path from interior of the membrane (e.g., inside the endosome) out into the cytoplasm intracellular environment. In specific embodiments, a polymer provided herein is hemolytic. In specific embodiments, a polymer provided herein is endosomal-permeable (effects a change in permeability allowing for release of the agent (by itself or in association with the micelle) or endosomolytic. Without being bound by theory not expressly recited in the claims, a membrane destabilizing polymer can directly or indirectly elicit a change (e.g., a permeability change) in a cellular membrane structure (e.g., an endosomal membrane) so as to permit an agent (e.g., polynucleotide), in association with or independent of a heterogeneous polymeric micelle (or a constituent polymer thereof), to pass through such membrane structure—for example to enter a cell or to exit a cellular vesicle (e.g., an endosome). A membrane destabilizing polymer can be (but is not necessarily) a membrane disruptive polymer. A membrane disruptive polymer can directly or indirectly elicit lysis of a cellular membrane (e.g., as observed for a substantial fraction of a population of cellular membranes). Generally, membrane destabilizing or membrane disruptive properties of polymers or micelles can be assessed by various means. In one non-limiting approach, a change in a cellular membrane structure can be observed by assessment in assays that measure (directly or indirectly) release of an agent (e.g., polynucleotide) from cellular membranes (e.g., endosomal membranes)—for example, by determining the presence or absence of such agent, or an activity of such agent, in an environment external to such membrane. Another non-limiting approach involves measuring red blood cell lysis (hemolysis)—e.g., as a surrogate assay for a cellular membrane of interest. It is presently preferred that the cellular membrane affected by a polymer of this invention is an endosomal membrane.

The membrane destabilizing or membrane disruptive polymer can be a pH sensitive polymer having membrane destabilizing activity or membrane disrupting activity at a desired pH. In some embodiments, membrane destabilizing polymers (e.g., copolymers) or membrane destabilizing block copolymers provided herein are membrane destabilizing (e.g., in an aqueous medium) at an endosomal pH. In some embodiments, the membrane destabilizing block copolymers are membrane destabilizing (e.g., in an aqueous medium) at a pH of about 6.5 or lower, preferably at a pH ranging from about 5.0 to about 6.5, or at a pH of about 6.2 or lower, preferably at a pH ranging from about 5.0 to about 6.2, or at a pH of about 6.0 or lower, preferably at a pH ranging from about 5.0 to about 6.0.

Preferably, in each case, the membrane destabilizing or membrane disruptive polymer can have membrane destabilizing activity or membrane disrupting activity at a desired quantity (e.g., concentration) of polymer. As a non-limiting example, the membrane destabilizing or membrane disruptive polymer can be effective at a concentration ranging from about 0.5 ug/ml to about 50 ug/ml, preferably from about 1 ug/ml to about 30 ug/ml and in some cases from about 5 ug/ml to about 25 ug/ml.

Generally, a membrane destabilizing or membrane disruptive characteristic of a polymer can be determined by suitable assays known in the art. For example, membrane-destabilizing activity or membrane-disruptive activity of a polymer can be determined in an in vitro cell assay. An endosomal-permeable or an endosomolytic polymer can be determined in an in vitro cell assay. A hemolytic polymer can be determined in an in vitro cell assay. Alternatively, for example, membrane-destabilizing activity or membrane-disruptive activity of a polymer can be determined in an in vivo assay protocol, such as a non-human mammalian assay protocol. An endosomal-permeable or an endosomolytic polymer can be determined in an in vivo assay protocol. A hemolytic polymer can be determined in an in vivo assay protocol.

Preferably, the membrane-destabilizing polymer can be characterized by an in-vitro or an in-vivo hemolytic assay. Preferably, for example, the membrane destabilizing polymer can have a hemolytic activity at pH 6.2 which is at least two times its hemolytic activity at pH 7.4. In some instances, the membrane-destabilizing polymer can have a hemolytic activity at pH 5.8 which is at least three times its hemolytic activity at pH 7.4. In preferred approaches, the membrane-destabilizing polymer can be substantially non-hemolytic at pH greater than about 7.4. In a more specific characterization, the membrane-destabilizing polymer can, at concentration of about 20 ug/ml, be hemolytic at a pH of or less than about 5.8, and substantially non-hemolytic at a pH greater than about 7.4 in an in-vitro cell assay.

Alternatively, the membrane destabilizing polymer can be characterized by an in-vitro or an in-vivo assay involving endosomal-permeation or endosomolysis. Specifically, the membrane-destabilizing polymer can be endosomal-permeable or endosomolytic in an in-vitro cell assay. The membrane-destabilizing polymer is endosomal-permeable or endosomolytic in an in-vivo non-human mammalian assay.

A membrane destabilizing functionality can also be characterized in the context of a heterogeneous polymeric micelle. Preferably, the polymeric micelle is endosomal-permeable or endosomolytic in an in-vitro cell assay. Preferably, the polymeric micelle is endosomal-permeable or endosomolytic in an in-vivo non-human mammalian assay.

A membrane destabilizing functionality can also be characterized in the context of a composition comprising a heterogeneous polymeric micelle and a bimolecular agent such as a polynucleotide. For example, an endosomal-permeable or endosomolytic property of a micelle or a composition can be determined by evaluating gene expression in an in-vitro cell assay. Such property can alternatively be determined by evaluating whether the composition modulates gene expression in an in-vivo non-human mammalian assay.

As described further in the following, in preferred embodiments, the membrane destabilizing polymer or membrane-disrupting polymer can be realized in connection with the hydrophobic block of the first polymer and/or the hydrophobic block of the second polymer.

Preferred Polymers—Hydrophobic Blocks

In preferred embodiments, the hydrophobic block of the first polymer and/or the hydrophobic block of the second polymer comprise a polymer chain which is hydrophobic. The hydrophobic block of the first polymer and/or the second polymer can comprise a plurality of hydrophobic monomeric residues. Hydrophobic monomeric residues can have a hydrophobic species. Generally, the hydrophobic species can be a constituent moiety of a monomeric residue which contributes to a hydrophobic character (i.e., serves as a hydrophobicity enhancing moiety) of the polymer or a block thereof. Hydrophobicity is a well known term of art describing a physical property of a compound measured by the free energy of transfer of the compound between a non-polar solvent and water (Hydrophobicity regained. Karplus P. A., *Protein Sci.*, 1997, 6: 1302-1307.) Without being bound by theory not expressly recited in the claims, a compound's hydrophobicity can be measured, for example, by a log P value, the logarithm of a partition coefficient (P), which is defined as the ratio of concentrations of a compound in the two phases of a mixture of two immiscible solvents, e.g. octanol and water. Experimental methods for determination of hydrophobicity as well as methods of computer-assisted calculation of log P values are known. Hydrophobic species of the present invention include but are not limited to aliphatic, heteroaliphatic, aryl, and heteroaryl groups.

Hydrophobic monomeric residues can be charged or non-charged, generally. Some embodiments include neutral (non-charged) hydrophobic monomeric residues. In some embodiments, polymer chains can independently comprise a plurality of monomeric residues having a hydrophobic species selected from ($C_2$-$C_8$) alkyl, ($C_2$-$C_8$) alkenyl, ($C_2$-$C_8$) alkynyl, aryl, and heteroaryl (each of which may be optionally substituted). In certain embodiments, the plurality of monomeric residues can be derived from polymerization of ($C_2$-$C_8$) alkyl-ethacrylate, a ($C_2$-$C_8$) alkyl-methacrylate, or a ($C_2$-$C_8$) alkyl-acrylate (each of which may be optionally substituted).

Preferably, the hydrophobic block of the first polymer and/or the second polymer can preferably further comprise a plurality of anionic monomeric residues. Accordingly, the hydrophobic block of the first polymer and/or the second polymer can comprise a plurality of hydrophobic monomer residues and a plurality of anionic monomeric residues. Anionic monomeric residues can have a species charged or chargeable to an anion, including a protonatable anionic species. The chargeable species can preferably be anionic at serum physiological pH, and substantially neutral or non-charged at the pH of the membrane being destabilized or disrupted—e.g., preferably at an endosomal pH. In some preferred embodiments, the hydrophobic block of the first polymer and/or the second polymer can comprise a plurality of anionic hydrophobic monomeric residues—monomeric residues comprising both hydrophobic species and species charged or chargeable to an anion. In each of such aforementioned embodiments, the hydrophobic block can be considered hydrophobic in the aggregate.

Anionic monomeric residues can preferably comprise a protonatable anionic species. Considered in the aggregate, as incorporated into a polymer chain, such anionic monomeric residues can be substantially anionic at a pH greater than 7.0 and substantially neutral (non-charged) at pH of or less than 6.0. Preferably, the hydrophobic block of the first polymer, and/or the second polymer (which comprises anionic monomeric residues) can have a pKa ranging from about 5.8 to about 7.0. Anionic monomeric residues can independently comprise a plurality of monomeric residues having a protonatable anionic species selected from carboxylic acid, sulfonamide, boronic acid, sulfonic acid, sulfinic acid, sulfuric acid, phosphoric acid, phosphinic acid, and phosphorous acid groups, and combinations thereof. Preferred anionic monomeric residues can be derived from polymerization of a ($C_2$-$C_8$) alkyl acrylic acid.

The hydrophobic block of the first polymer and/or the second polymer can preferably comprise, or further comprise a plurality of cationic monomeric residues. Accordingly, for example, the hydrophobic block of the first polymer and/or the second polymer can comprise a plurality of hydrophobic monomeric residues and a plurality of cationic monomeric residues. Alternatively and preferably in some embodiments, the hydrophobic block of the first polymer and/or the second polymer can comprise a plurality of hydrophobic monomeric residues, a plurality of anionic monomeric residues and a plurality of cationic monomeric residues. Generally, cationic monomeric residues can have a species that is charged or chargeable to a cation, including a deprotonatable cationic species. The chargeable species can preferably be cationic at serum physiological pH. In some preferred embodiments, the hydrophobic block of the first polymer and/or the second polymer can comprise a plurality of monomeric residues comprising various combinations of hydrophobic species, species charged or chargeable to an anion and species charged or chargeable to an cation. In such embodiments, and as discussed further below, the hydrophobic block of the first polymer and/or the second polymer can be charge modulated, and preferably charge balanced—being substantially overall neutral in charge. In each of such aforementioned embodiments, the hydrophobic block can be considered hydrophobic in the aggregate.

Cationic monomeric residues can preferably comprise a deprotonatable cationic species. Considered in the aggregate, as incorporated into a polymer chain, such cationic monomeric residues can be substantially cationic at a pH of or less than 7.0. Preferably, the hydrophobic block of the first polymer and/or the second polymer (comprising cationic monomeric residues) can have a pKa ranging from about 6.3 to about 7.8. Cationic monomeric residues can independently comprise a plurality of monomeric residues having a species selected from the group consisting of acyclic amine, acyclic imine, cyclic amine, cyclic imine, and nitrogen-containing heteroaryl. Preferred cationic monomeric residues can be derived from polymerization of, in each case optionally substituted, (N,N-di($C_1$-$C_6$)alkyl-amino($C_1$-$C_6$)alkyl-ethacrylate, N,N-di($C_1$-$C_6$)alkyl-amino($C_1$-$C_6$)alkyl-methacrylate, or N,N-di($C_1$-$C_6$)alkyl-amino($C_1$-$C_6$)alkyl-acrylate.

Generally, the hydrophobic block of the first polymer and/or the second polymer can be charge modulated, for example including hydrophobic monomeric residues together with both anionic monomeric residues and cationic monomeric residues. The relative ratio of anionic monomeric residues and cationic monomeric residues can be controlled to achieve a desired overall charge characteristic. In preferred embodiments, for example, such polymer or polymer chain can be charge balanced—having a substantially neutral overall charge in an aqueous medium at physiological pH (e.g., pH 7.2 to 7.4). Preferably, the hydrophobic block of the first polymer and/or the second polymer can have a substantially neutral overall charge in an aqueous medium at pH 7.4.

In preferred embodiments, the hydrophobic block of the first polymer and/or the second polymer can be or can consist essentially of or can comprise a membrane destabilizing polymer or a membrane-disrupting polymer. Preferably, for example, the hydrophobic block of the first block copolymer and/or the second block copolymer can be membrane destabilizing or membrane disruptive and comprise a plurality of hydrophobic monomeric residues, and a plurality of anionic monomeric residues, and optionally a plurality of cationic monomeric residues. In each of such aforementioned embodiments, the hydrophobic block can be considered hydrophobic in the aggregate. The membrane-destabilizing or membrane-disruptive polymer can have the attributes described in the preceding section.

In preferred embodiments of the invention, the hydrophobic block of the first polymer and/or the second polymer can be or consist essentially of or comprise at least one polymer chain which includes, a plurality of hydrophobic monomeric residues, a plurality of anionic monomeric residues, and optionally a plurality of cationic monomeric residues in ratios adapted to enhance membrane destabilizing or membrane disruptive activity of the polymer chain. For example and without limitation, in such embodiments, at pH 7.4, the ratio of hydrophobic:(anionic+cationic) species ranges from about 1:3 to about 3:1, and the ratio of anionic:cationic species ranges from about 1:0 to about 1:4. In preferred such embodiments, at pH 7.4, the ratio of hydrophobic:(anionic+cationic) species ranges from about 1:2 to about 2:1 (e.g., about 1:1), and the ratio of anionic:cationic species ranges from about 4:1 to about 1:4 (e.g., from about 3:2 to about 2:3, or e.g., about 1:1).

As a general, non-limiting example, the heterogeneous polymeric micelles of the invention can comprise first and second compositionally distinct polymers, each of which can be a block copolymer. With reference to FIG. 1B, and the foregoing discussion in connection therewith, for example, each of the first and second block copolymers can comprise a first polymer chain defining a first block A of the copolymer, and a second membrane disruptive polymer chain defining a second hydrophobic block B of the copolymer. For example, each such block copolymer can comprise a first polymer chain defining a first block A of the copolymer, and a second polymer chain defining a second hydrophobic block B of the copolymer which includes (i) a plurality of hydrophobic monomeric residues, and (ii) a plurality of anionic monomeric residues having a chargeable species, the chargeable species being anionic at serum physiological pH, and being substantially neutral or non-charged at an endosomal pH. In an alternative orientation, and generally less preferred approach, the block copolymer can preferably comprise a first membrane disruptive polymer chain defining a first block A of the copolymer, and a second polymer chain defining a second block B of the copolymer. For example, the block copolymer can comprise a first polymer chain defining a first block A of the copolymer and which includes (i) a plurality of cationic monomeric residues which contribute to membrane destabilization (e.g., via proton-sponge effect), and optionally (ii) a plurality of neutral (non-charged) monomeric residues, and a second polymer chain defining a second hydrophobic block B of the copolymer.

Generally, the hydrophobic block of the first polymer and/or the second polymer comprises a plurality of monomeric residues derived from a polymerizable monomer. As described more fully below, the polymerizable monomer is preferably an ethylenically unsaturated monomer, such as an acrylic monomer or a vinylic monomer. Preferably, the hydrophobic block of the first polymer and/or the second polymer comprises a plurality of first monomeric residues derived from a first polymerizable monomer having a hydrophobic species and an (protonatable) anionic species, and optionally a plurality of second monomeric residues derived from a second polymerizable monomer having a (deprotonatable) cationic species. Alternatively, the hydrophobic block of the first polymer and/or the second polymer can comprise a plurality of first monomeric residues derived from a first polymerizable monomer having a hydrophobic species, a plurality of second monomeric residues derived from a second polymerizable monomer having an (protonatable) anionic species, and optionally a plurality of third monomeric residues derived from a third polymerizable monomer having a (deprotonatable) cationic species. Preferably, the hydrophobic block of the first polymer and/or the second polymer comprises a plurality of monomeric residues derived from controlled (i.e., living) radical polymerization of a polymerizable monomer.

Further aspects and features of the hydrophobic block of the first polymer and/or the second polymer are described below, in connection with the section directed to polymerization generally.

Preferred Polymers—Hydrophilic Blocks

In preferred embodiments, a block of the first block copolymer and/or a block of the second block copolymer can comprise a polymer chain which is hydrophilic. The hydrophilic block of the first polymer and/or the second polymer can generally comprise a plurality of hydrophilic monomeric residues. Hydrophilic monomeric residues can have a hydrophilic species. The hydrophilic species can be a polar species. Generally, the constituent monomeric residues of the hydrophilic block of the first polymer and/or the second polymer are not narrowly critical, and can be or comprise hydrophilic monomeric residues which are neutral (non-charged), anionic, cationic, or zwitterionic. The hydrophilic block of the first polymer and/or the second polymer comprising such monomeric residues can have an overall charge characteristic which is neutral (non-charged), anionic, cationic, or zwitterionic, and preferably considered hydrophilic in the aggregate.

Generally and as more specifically delineated below, in various embodiments of the invention, the hydrophilic block of the first polymer and/or the second polymer be or consist essentially of or comprise a polymer chain which is cationic—e.g., a cationic hydrophilic polymer chain. The hydrophilic block of the first polymer and/or the second polymer can comprise a plurality of cationic monomeric residues, such as cationic hydrophilic monomeric residues. Cationic monomeric residues can have a species that is charged or chargeable to a cation, including a deprotonatable cationic species. The chargeable species can preferably be cationic at serum physiological pH. As discussed below, in some embodiments where charge-dilution is desirable, the hydrophilic block of the first polymer and/or the second polymer can further comprise a plurality of neutral monomeric residues, such as neutral hydrophilic monomeric residues, in addition to the plurality of cationic monomeric residues. In each of such aforementioned embodiments, the hydrophilic block can be considered hydrophilic in the aggregate.

Cationic monomeric residues can preferably comprise a deprotonatable cationic species. Considered in the aggregate, as incorporated into a polymer chain, such cationic monomeric residues can be substantially cationic at a pH of or greater than 7.0. Preferably, the hydrophobic block of the first polymer and/or the second polymer (comprising cationic monomeric residues) can have a pKa ranging from about 6.3 to about 7.8. Cationic monomeric residues can independently comprise a plurality of monomeric residues having a species selected from the group consisting of acyclic amine, acyclic imine, cyclic amine, cyclic imine, and nitrogen-containing heteroaryl. Preferred cationic monomeric residues can be derived from polymerization of, in each case optionally substituted, (N,N-di($C_1$-$C_6$)alkyl-amino($C_1$-$C_6$)alkyl-ethacrylate, N,N-di($C_1$-$C_6$)alkyl-amino($C_1$-$C_6$)alkyl-methacrylate, or N,N-di($C_1$-$C_6$)alkyl-amino($C_1$-$C_6$)alkyl-acrylate.

Generally and as more specifically delineated below, in various embodiments of the invention, the hydrophilic block of the first polymer and/or the second polymer be or consist essentially of or comprise a polymer chain which is neutral (non-charged)—e.g., a neutral (non-charged) hydrophilic polymer chain. The hydrophilic block of the first polymer and/or the second polymer can comprise a plurality of neutral (non-charged) monomeric residues, such as neutral (non-charged) hydrophilic monomeric residues, such as a neutral polar monomeric residue. Preferred neutral (non-charged) monomeric residues can be derived from polymerization of polyethyleneglycol methacrylate (PEGMA) (e.g., with 1-20 ethylene oxide units, such as illustrated in compound 2, or 4-5 ethylene oxide units, or 7-8 ethylene oxide units), preferably pegylated methacrylic monomers, e.g., $CH_3O(CH_2O)_{2\text{-}20}OC(O)C(CH_3)=CH_2$ (PEGMA); pegylated acrylic monomers, e.g., $CH_3O(CH_2O)_{2\text{-}20}OC(O)CH=CH2$ (PEGA); N-isopropyl acrylamide (NIPAAM); 2-hydroxyethyl methacrylate (HEMA); hydroxypropyl methacrylate (various isomers, including for example N-(2-hydroxypropyl)methacrylate (HPMA)), 2-(2',3',4',6'-Tetra-O-acetyl-b-D-galactosyloxy) ethyl methacrylate (AcGalEMA); 2-(b-D-galactosyloxy) ethyl methacrylate (GalEMA); hydroxybutyl methacrylate (various isomers); hydroxypropyl acrylate (various isomers); hydroxybutyl acrylate (various isomers); and acrylamide, among others. Other such monomeric residues are described below in connection with polymerization, generally. In each of such aforementioned embodiments, the hydrophilic block can be considered hydrophilic in the aggregate.

In some preferred embodiments, the hydrophilic block of the first polymer and/or the second polymer can comprise a plurality of monomeric residues comprising various combinations of hydrophilic species. For example, the hydrophilic block of the first polymer and/or the second polymer can comprise a plurality of cationic monomeric residues and a plurality of neutral (non-charged) monomeric residues. In such embodiments, for example, the hydrophilic block of the first polymer and/or the second polymer can preferably be charge modulated (e.g., charge diluted)—being substantially overall cationic in overall charge, but including at least 10%, preferably at 20% (in each case by mole) non-charged monomeric residues. In such embodiments, for example, the hydrophilic block of the first polymer and/or the second polymer can preferably be more charge diluted—being substantially overall cationic in overall charge, but including at least 30%, at least 40% or at least 50% (in each case by mole) non-charged monomeric residues, and overall, ranging from about 10% to about 70% (by mole) non-charged monomeric residues. In each of such aforementioned embodiments, the hydrophilic block can be considered hydrophilic in the aggregate.

In an alternative approach, such charge modulation can be effected on based on supramolecular architecture—for example, by varying the relative amount or number of first polymer and second polymer aggregated into the heterogeneous micelle. For example, the hydrophilic block of the first polymer can comprise a plurality of cationic hydrophilic monomeric residues, including cationic species charged or chargeable to a cation, and the hydrophilic block of the second polymer can comprise a plurality of neutral hydrophilic monomeric residues. In such embodiments, charge modulation, e.g., various charge dilution can be realized by varying the relative ratio of first polymer (having cationic hydrophilic block) to the second polymer (having a neutral hydrophilic block). For example, the second polymer in such case can constitute at least 10%, preferably at 20% of the total amount of polymer (i.e., of the sum of the amount of first and second polymers). In such embodiments, for example, second polymer in such case can constitute at least 30%, at least 40% or at least 50% of the total amount of polymer, and overall, ranging from about 10% to about 70% of the total amount of polymer. In each of such aforementioned embodiments, the hydrophilic block can be considered hydrophilic in the aggregate.

Generally and as more specifically delineated below, in various embodiments of the invention, the hydrophilic block of the first polymer and/or the second polymer comprise a polymer chain which comprises conjugatable species (reactive functional moieties)—e.g., as pendant moieties of monomeric residues of a hydrophilic polymer chain. The hydrophilic block of the first polymer and/or the second polymer can comprise a plurality of monomeric residues having conjugatable species, preferably hydrophilic monomeric residues having conjugatable species, in each case preferably as a pendant moiety of the monomeric residue. Preferred monomeric residues having conjugatable species can be derived from polymerization of N-hydroxy succinimide ester of methylacrylic acid (MAA(NHS)), N-hydroxysuccinimide ester of acrylic acid (AA(NHS)), p-nitrophenyl methacrylate (MAA(PNP)), pyridyl disulfide acrylate monomer (PDSA), pyridyl disulfide methacrylate (PDSM), 2-aminoethyl methacrylate, pyridyldisulfide methacrylate monomer (PDSMA); glycidyl methacrylate; glycidyl acrylate; 3-azidopropyl methacrylate (AzPMA); trimethylsilylpropargyl methacrylate (TMSPMA); or acrylonitrile. Other such monomeric residues are described below in connection with polymerization, generally. In each of such aforementioned embodiments, the hydrophilic block can be considered hydrophilic in the aggregate.

In various embodiments of the invention, the hydrophilic block of the first polymer and/or the second polymer be or consist essentially of or comprise a polymer chain which is adapted to facilitate one or more additional constituent components and/or functional features important for the polymeric micelle (e.g., for intracellular delivery of an agent such as a polynucleotide.

Preferably, for example, the hydrophilic block of the first polymer and/or the second polymer, can associate an agent(s) such as polynucleotides. For example, polynucleotides or other agent(s) can be associated through ionic interactions with the hydrophilic block of the first polymer and/or the second polymer. For polynucleotides, the hydrophilic block of at least one (e.g., the first block copolymer), and optionally each of the first polymer and the second polymer, can comprise a polymer chain which is cationic—e.g., such as a cationic hydrophilic polymer chain. The hydrophilic block of the first polymer and/or the second polymer can comprise a plurality of cationic monomeric residues. In a composition comprising polynucleotides, such plurality of cationic monomeric residues can be in ionic association with the polynucleotide (through anionic species thereof). In some embodiments, such hydrophilic block of the first polymer and/or the second polymer can further comprise a plurality of neutral (non-charged) monomeric residues, such as neutral hydrophilic monomeric residues. Such non-charged monomeric residues can be used for charge modulation (charge neutralization) as described above. In each of such aforementioned embodiments, the hydrophilic block can be considered hydrophilic in the aggregate. Other aspects of associating polynucleotides with the heterogeneous polymeric micelles are described in connection with polynucleotide-containing compositions below.

Alternatively, polynucleotides or other agent(s) can be associated with the hydrophilic block of the first polymer and/or the second polymer through covalent conjugation to one or more of the constituent polymers. Covalent conjugation can be achieved, for example, through a monomeric residue having a conjugatable species (i.e., reactive functional group moiety). Hence, in such embodiments, the hydrophilic block of the first polymer and/or the second polymer can comprise a plurality of monomeric residues having conjugatable species, preferably hydrophilic monomeric residues having conjugatable species, in each case preferably as a pendant moiety of the monomeric residue. Other aspects of associating polynucleotides with the heterogeneous polymeric micelles are described in connection with polynucleotide-containing compositions below.

Some agents such as polynucleotides which are hydrophilic can be alternatively associated by covalent conjugation to an end of the hydrophobic block of the first polymer and/or the second polymer, allowing such agent (e.g., polynucleotide) to essentially constitute and function as a hydrophilic block of the end-conjugated polymer. Various known end-conjugation approaches are known in the art, and can be incorporated in connection with this embodiment of the invention. Controlled (living) radical polymerization approaches afford functional conjugating moieties at an alpha end or at an omega end of a polymer (e.g., a polymer derived from RAFT polymerization as described below). For example, and without limitation, a conjugatable moiety can be provided at an alpha- or an omega-end of a constituent polymer, by preparing the polymer in the presence of a chain transfer reagent comprising a conjugatable moiety (e.g., an azide or a pyridyl disulfide group), where the conjugatable group is compatible with the conditions of the polymerization process. See, for example, Heredia, K. L et al., Chem. Commun., 2008, 28, 3245-3247; See also Boyer et al., Direct Synthesis of Well-Defined Heterotelechelic Polymers for Bioconjugations Macromolecules, 2008, 41(15), pp 5641-5650 (e.g., providing block copolymers having functional groups at both the α and ω ends using chain transfer agent that incorporates the corresponding functional groups)). A copolymer with a conjugatable thiol omega end group can be prepared by reducing a thiocarbonylthio macroCTA to form a thiol end as a conjugatable end group. A chain transfer agent can optionally comprise a masked conjugatable group which can be deprotected to link an agent. Other aspects of associating polynucleotides with the heterogeneous polymeric micelles are described in connection with polynucleotide-containing compositions below.

The hydrophilic block of the first polymer and/or the second polymer can be, can consist essentially of or comprise a shielding moiety. For example, shielding can be effected by incorporating species or moieties effective for steric shielding, for enhancing stability against metabolism (e.g., enzymatic digestion), for mediating potential toxicities, for enhancing pharmacokinetics, for enhancing a desired biodistribution, among others. Such shielding functionality can be of substantial importance for delivery of biomolecular agents such as polynucleotides. In general, in embodiments involving a polynucleotide agent, shielding can be advantageously realized where the hydrophilic block of the first polymer and/or the second polymer can comprise a plurality of neutral (non-charged) monomeric residues, such as neutral (non-charged) hydrophilic monomeric residues. Specific preferred shielding approaches are discussed in detail in the shielding section below.

The hydrophilic block of the first polymer and/or the second polymer can provide targeting functionality, for example, directing the heterogeneous micelle and its associated agent (e.g., a polynucleotide) to a particular cell type of interest. Targeting can be effected, for example by covalent conjugation of one or more targeting moieties—including moieties having various specificity—such as polysaccharides or oligosaccharides or specific targeting ligands—and effective for receptor-mediated endocytosis. Covalent conjugation can be achieved, for example, through a monomeric residue having a conjugatable species (i.e., reactive functional group moiety). Hence, in such embodiments, the hydrophilic block of the first polymer and/or the second polymer can comprise a plurality of monomeric residues having conjugatable species, preferably hydrophilic monomeric residues having conjugatable species, in each case preferably as a pendant moiety of the monomeric residue. The targeting moiety can be covalently coupled to the hydrophilic block through the conjugatable species, and optionally through a linking moiety. Specific preferred targeting approaches are discussed in detail in the targeting section below. In some approaches, targeting moieties which are hydrophilic can be alternatively associated by covalent conjugation to an end of the hydrophobic block of the first polymer and/or the second polymer, or to an end of the hydrophilic block of the first polymer and/or the second polymer, in each case allowing such targeting moiety to essentially constitute and function all or part of a hydrophilic block of the end-conjugated polymer. Various known end-conjugation approaches are known in the art, and can be incorporated in connection with this embodiment of the invention.

Polymers, Generally

Without detracting from the foregoing preferred embodiments and approaches, the following aspects general apply to the first and second compositionally distinct constituent polymers of the heterogeneous polymeric micelle, or to any block of a first block copolymer or a second block copolymer compositionally distinct from the first block copolymer.

Generally, each of the constituent polymers of the heterogeneous polymeric micelles—or blocks of such polymers, can comprise one or more repeat units—monomer (or monomeric) residues—derived from a process which includes polymerization. Such monomeric residues can optionally also include structural moieties (or species) derived from post-polymerization (e.g., derivitization) reactions. Monomeric residues are constituent moieties of the polymers, and accordingly, can be considered as constitutional units of the polymers. Generally, a polymer of the invention can comprise constitutional units which are derived (directly or indirectly via additional processes) from one or more polymerizable monomers.

Generally, each of the constituent polymers of the heterogeneous polymeric micelles—or blocks of such polymers, can be a homopolymer (derived from polymerization of one single type of monomer—having essentially the same chemical composition) or a copolymer (derived from polymerization of two or more different monomers—having different chemical compositions). Polymers which are copolymers can be a random copolymer chain or a block copolymer chain (e.g., diblock copolymer, triblock copolymer, higher-ordered block copolymer, etc). Any given block copolymer chain can be conventionally configured and effected according to methods known in the art.

Generally, each of the constituent polymers of the heterogeneous polymeric micelles—or blocks of such polymers, can be a linear polymer, or a non-linear polymer. Non-linear polymers can have various architectures, including for example branched polymers, star-polymers, dendrimer polymers, and can be cross-linked polymers, semi-cross-linked polymers, graft polymers, and combinations thereof.

Generally, each of the constituent polymers of the heterogeneous polymeric micelles—or blocks of such polymers, can be a prepared by controlled (living) radical polymerization, such as reversible addition-fragmentation chain transfer (RAFT) polymerization. Such methods and approaches are generally known in the art, and are further described herein. Alternatively, a polymer can be a prepared by conventional polymerization approaches, including conventional radical polymerization approaches.

Generally, each of the constituent polymers of the heterogeneous polymeric micelles—or blocks of such polymers, is prepared by a method other than by stepwise coupling approaches involving a sequence of multiple individual reactions (e.g., such as known in the art for peptide synthesis or for oligonucleotide synthesis). Preferably, a polymer or block thereof is a non-peptidic polymer (consists of a polymer other than an amino acid polymer). Preferably, except as otherwise described herein, a polymer or a block thereof is a non-nucleic acid polymer chain (consists of a polymer other than a nucleic acid polymer. Generally, a polymer or a block thereof is a non-lipidic moiety (consists of a polymer having constituent moieties other than lipidic moieties). Preferably, a polymer or a block thereof is a non-saccharide polymer. In contrast, for clarity, notwithstanding and without prejudice to the foregoing, the targeting moieties and/or other biomolecular agents of the inventions can be an amino acid polymer (e.g., a peptide) or a nucleic acid polymer (e.g., an oligonucleotide) or a polysaccharide.

Generally, each of the constituent polymers of the heterogeneous polymeric micelles—or blocks of such polymers, prepared by controlled (living) radical polymerization, such as reversible addition-fragmentation chain transfer (RAFT) polymerization, may include moieties other than the monomeric residues (repeat units). For example, and without limitation, such polymers may include polymerization-process-dependent moieties at the α-end or at the ω-end of the polymer chain. Typically, for example, a polymer chain derived from controlled radical polymerization such as RAFT polymerization may further comprise a radical source residue covalently coupled with the α-end thereof. For example, the radical source residue can be an initiator residue, or the radical source residue can be a leaving group of a reversible addition-fragmentation chain transfer (RAFT) agent. Typically, as another example, a polymer derived from controlled radical polymerization such as RAFT polymerization may further comprise a chain transfer residue covalently coupled with the ω-end thereof. For example, a chain transfer residue can be a thiocarbonylthio moiety having a formula —SC(=S)Z, where Z is an activating group. Typical RAFT chain transfer residues are derived from radical polymerization in the presence of a chain transfer agent selected from xanthates, dithiocarbamates, dithioesters, and trithiocarbonates. The process-related moieties at α-end or at the ω-end of the polymer or between blocks of different polymers can comprise or can be derivatized to comprise functional groups, e.g., suitable for covalent linking, etc.

Further aspects of each of the constituent polymers of the heterogeneous polymeric micelles—or blocks of such polymers, are disclosed in the following paragraphs, including preferred polymerizable monomers from which the repeat units of the polymers are derived.

Generally, and preferably, one or more, and preferably each of the constituent polymers of the heterogeneous polymeric micelles—or blocks of such polymers, can comprise repeat units derived from ethylenically unsaturated monomers. The term "ethylenically unsaturated monomer" is defined herein as a compound having at least one carbon double or triple bond.

Preferably, constituent polymers of the heterogeneous polymeric micelle or blocks thereof can comprise monomeric residues derived from a polymerizable monomer. Preferably, such constituent polymers or blocks thereof can comprise monomeric residues derived from controlled radical polymerization of a polymerizable monomer.

In preferred embodiments, the polymerizable monomer can be an ethlenically unsaturated monomer, such as an acrylic monomer or a vinylic monomer. Preferably, the polymerizable monomer can be an acrylic monomer selected from an optionally substituted acrylic acid, an optionally substituted acrylamide, and an optionally substituted acrylate. In especially preferred embodiments, the polymerizable monomer can be selected from an optionally $C_1$-$C_8$ alkyl-substituted acrylic acid, an optionally $C_1$-$C_8$ alkyl-substituted acrylamide, and an optionally $C_1$-$C_8$ alkyl-substituted acrylate.

Preferably, constituent polymers of the heterogeneous polymeric micelle or blocks thereof can be derived from a polymerizable monomer and have a polydispersity index of not more than 1.5, preferably not more than about 1.4, and in some embodiments, not more than about 1.2, or not more than about 1.1, or not more than 1.05.

In preferred embodiments, the polymerizable monomer can be a monomer having a formula II

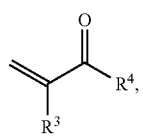

II where $R^3$ is selected from the group consisting of hydrogen, hydroxyl, and optionally substituted $C_1$-$C_3$ alkyl, and $R^4$ is a group comprising one or more species selected from an anionic species, a cationic species, a neutral species, a hydrophobic species.

Preferably, $R^4$ is selected from the group consisting of hydrogen, —$OR^5$, and —$NR^6R^7$, $R^5$ is selected from the group consisting of hydrogen, optionally substituted alkyl, alkoxy, optionally substituted alkenyl, optionally substituted alkynyl, optionally substituted polyoxylated alkyl, optionally substituted aryl, and optionally substituted heteroaryl, and $R^6$ and $R^7$ are each independently selected from the group consisting of hydrogen, optionally substituted alkyl, optionally substituted alkenyl, optionally substituted alkynyl, optionally substituted polyoxylated alkyl, optionally substituted aryl, and optionally substituted heteroaryl.

Preferably in monomers of formula II, $R^3$ is selected from the group consisting of hydrogen and methyl, and $R^4$ is selected from the group consisting of —$OR^5$, and —$NR^6R^7$, $R^5$ is selected from the group consisting of hydrogen, optionally substituted $C_1$-$C_3$ alkyl, alkoxy, alkoxy, and polyoxylated alkyl, and $R^6$ and $R^7$ are each independently selected from the group consisting of hydrogen, and optionally substituted $C_1$-$C_3$ alkyl.

Further preferred non-limiting examples of the ethylenically unsaturated monomers are: an alkyl (alkyl)acrylate, a alkyl methacrylate, an alkyl acrylic acid, an N-alkylacrylamide, a methacrylamide, a styrene, an allylamine, an allylammonium, a diallylamine, a diallylammonium, an n-vinyl formamide, a vinyl ether, a vinyl sulfonate, an acrylic acid, a sulfobetaine, a carboxybetaine, a phosphobetaine, or maleic anhydride.

In various embodiments, any monomer suitable for providing the polymers described herein may be used to effect the invention. In some embodiments, monomers suitable for use in the preparation of polymers provided herein include, by way of non-limiting example, one or more of the following monomers: methyl methacrylate, ethyl acrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, oligoethyleneglycol methacrylate, oligoethyleneglycol acrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers), p-vinylbenzenesulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysillpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-arylmaleimide, N-phenylmaleimide, N-alkylmaleimide, N-butylimaleimide, N-vinylpyrrolidone, N-vinylcarbazole, butadiene, isoprene, chloroprene, ethylene, propylene, 1,5-hexadienes, 1,4-hexadienes, 1,3-butadienes, 1,4-pentadienes, vinylalcohol, vinylamine, N-alkylvinylamine, allylamine, N-alkylallylamine, diallylamine, N-alkyldiallylamine, alkylenimine, acrylic acids, alkylacrylates, acrylamides, methacrylic acids, alkylmethacrylates, methacrylamides, N-alkylacrylamides, N-alkylmethacrylamides, styrene, vinylnaphthalene, vinyl pyridine, ethylvinylbenzene, aminostyrene, vinylimidazole, vinylpyridine, vinylbiphenyl, vinylanisole, vinylimidazolyl, vinylpyridinyl, vinylpolyethyleneglycol, dimethylaminomethylstyrene, trimethylammonium ethyl methacrylate, trimethylammonium ethyl acrylate, dimethylamino propylacrylamide, trimethylammonium ethylacrylate, trimethylanunonium ethyl methacrylate, trimethylammonium propyl acrylamide, dodecyl acrylate, octadecyl acrylate, or octadecyl methacrylate monomers, or combinations thereof.

In some embodiments, each of the constituent polymers of the heterogeneous polymeric micelles—or blocks of such polymers, can be derived from certain specific monomers and combinations of monomers, for example, for use in connection with various embodiments, such as for uses associated with polynucleotide containing compositions. Such preferred polymers are described below.

Generally, one or more of the constituent polymers of the heterogeneous polymeric micelles—or blocks of such polymers, can include repeat units derived from functionalized monomers, including versions of the aforementioned monomers. A functionalized monomer, as used herein, can include a conjugatable species—e.g., can be a monomer comprising a masked (protected) or non-masked (unprotected) functional group, e.g. a group to which other moieties—such as agents (e.g., polynucleotides), targeting moieties, shielding moieties, among others, can be covalently coupled following polymerization. The non-limiting examples of such groups are primary amino groups, carboxyls, thiols, hydroxyls, azides, and cyano groups. Several suitable masking groups are available (see, e.g., T. W. Greene & P. G. M. Wuts, Protective Groups in Organic Synthesis (2nd edition) J. Wiley & Sons, 1991. P. J. Kocienski, Protecting Groups, Georg Thieme Verlag, 1994).

As used herein, a "block" copolymer refers to a structure comprising one or more sub-combination of constitutional or monomeric units. In some embodiments, the block copolymer is a diblock copolymer, a tri-block copolymer or a higher-ordered block copolymer. For example, a diblock copolymer can comprise two blocks; a schematic generalization of such a polymer is represented by the following: [Aa/Bb/Cc/ . . . ]m-[Xx/Yy/Zz/ . . . ]n, wherein each letter stands for a constitutional or monomeric unit, and wherein each subscript to a constitutional unit represents the mole fraction of that unit in the particular block, the three dots indicate that there may be more (there may also be fewer) constitutional units in each block and m and n indicate the molecular weight (or weight fraction) of each block in the diblock copolymer. As suggested by such schematic representation, in some instances, the number and the nature of each constitutional unit is separately controlled for each block. The schematic is not meant and should not be construed to infer any relationship whatsoever between the number of constitutional units or the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the form: x-x-y-z-x-y-y-z-y-z-z-z . . . . An exemplary alternating random configuration may have the form: x-y-x-z-y-x-y-z-y-x-z . . . , and an exemplary regular alternating configuration may have the form: x-y-z-x-y-z-x-y-z . . . . An exemplary regular block configuration may have the following general configuration: . . . x-x-x-y-y-y-z-z-z-x-x-x . . . , while an exemplary random block configuration may have the general configuration: .... x-x-x-z-z-x-x-y-y-y-y-z-z-z-x-x-z-z-z- .... In a gradient polymer, the content of one or more monomeric units increases or decreases in a gradient manner from the α end of the polymer to the ω end. In none of the preceding generic examples is the particular juxtaposition of individual constitutional units or blocks or the number of constitutional units in a block or the number of blocks meant nor should they be construed as in any manner bearing on or limiting the actual structure of constituent block copolymers of the heterogeneous polymeric micelle.

As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers.

A unimer or monoblock polymer is a synthetic product of a single polymerization step. The term monoblock polymer includes a copolymer such as a random copolymer (i.e. a product of polymerization of more than one type of monomers) and a homopolymer (i.e. a product of polymerization of a single type of monomers).

Methods for preparing each of the constituent polymers of the heterogeneous polymeric micelles—or blocks of such polymers, are described below, and are generally applicable for, but not be limiting of, the polymers described herein.

One or more of the constituent polymers of the heterogeneous polymeric micelles—or blocks of such polymers, can be a crosslinking polymer or polymer block—effectively allowing for covalent coupling of some or all of the constituent polymers of the heterogeneous micelle. In some embodiments, the first polymer is covalently crosslinked to the second compositionally distinct polymer, whereby the polymeric micelle is a crosslinked polymeric micelle. In a crosslinked polymeric micelle, preferably the hydrophobic block of the first polymer is covalently crosslinked to the hydrophobic block of the second polymer. In one approach for a crosslinked polymeric micelle, the first polymer and the second polymer can each comprise a plurality of monomeric residues derived from controlled radical polymerization of an ethylenic monomer, where at least one such monomer is a bis-functional crosslinking monomer. In such embodiments, a crosslinking monomer comprises two or more polymerizable moieties. Crosslinking monomers can be an ethlenically unsaturated crosslinking agent. Ethlenically unsaturated crosslinking agents are known in the art, and can include dienes, such as butadiene, or octadiene. In an alternative approach a crosslinked polymeric micelle can be prepared by post-polymerization crosslinking, preferably of the hydrophobic block of the first polymer to the hydrophobic block of the second polymer, e.g., through functional groups of conjugatable monomeric residues included within the hydrophobic blocks. As a non-limiting example, a crosslinked polymeric micelle can be formed by crosslinking a first polymer and a second polymer each comprising a plurality of monomeric residues having an amine (or other) functional group, and linking through such functional groups (e.g., using a crosslinking agent such as epichlorohydrin).

Generally, one or more of the constituent polymers of the heterogeneous polymeric micelles—or blocks of such polymers can be a random copolymer, or a random copolymer block, in each case which comprises two or more compositionally distinct monomeric residues. Preferably, at least one block of at least one of the first polymer or the second polymer is a random copolymer comprising two or more compositionally distinct monomeric residues. More specifically, at least one block selected from the hydrophilic block of the first polymer, the hydrophobic block of the first polymer, the hydrophilic block of the second polymer and the hydrophobic block of the second polymer is preferably a random copolymer block comprising two or more compositionally distinct monomeric residues. Preferably at least two, or at least three, or each block selected from the hydrophilic block of the first polymer, the hydrophobic block of the first polymer, the hydrophilic block of the second polymer and the hydrophobic block of the second polymer is a random copolymer block comprising two or more compositionally distinct monomeric residues. Preferably, the first block of the first polymer is a random copolymer comprising two or more compositionally distinct monomeric residues. Preferably, the second block of the first polymer is a random copolymer comprising two or more compositionally distinct monomeric residues. Preferably, the first block of the second polymer is a random copolymer comprising two or more compositionally distinct monomeric residues. Preferably, the second block of the second polymer is a random copolymer comprising two or more compositionally distinct monomeric residues.

Generally, a single monomeric residue can include multiple moieties having different functionality—e.g., can comprise hydrophobic species as well as anionic species, or e.g., can comprise hydrophobic species as well as cationic species, or e.g., can comprise anionic species as well as cationic species. Hence, in any embodiment, the polymer can be or can comprise a polymer comprising a monomeric residue, for example such as an anionic hydrophobic monomeric residue—which includes hydrophobic species and anionic species (e.g., species which are anionic at about neutral pH).

Preferred Block Copolymers

Preferably, one or more of the constituent polymers of the heterogeneous polymeric micelles can be a block copolymer which can comprise or consist essentially of two or more blocks represented by formula I,

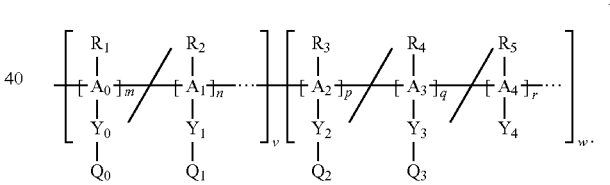

I where

A0, A1, A2, A3 and A4 are each selected from the group consisting of —C—C—, —C—, —C(O)(C)aC(O)O—, —O(C)aC(O)— and —O(C)bO—, a is an integer ranging from 1-4; and b is an integer ranging from 2-4;

Y4 is selected from the group consisting of hydrogen, (1C-10C)alkyl, (3C-6C)cycloalkyl, O-(1C-10C)alkyl, —C(O)O(1C-10C)alkyl, C(O)NR6(1C-10C) and aryl, any of which is optionally substituted with one or more fluorine groups;

Y0, Y1 and Y2 are each independently selected from the group consisting of a covalent bond, (1C-10C)alkyl-, —C(O)O(2C-10C) alkyl-, —OC(O)(1C-10C) alkyl-, —O(2C-10C)alkyl- and —S(2C-10C)alkyl- —C(O)NR6(2C-10C) alkyl-;

Y3 is selected from the group consisting of a covalent bond, (1C-10C)alkyl and (6C-10C)aryl; wherein tetravalent carbon atoms of A1-A4 that are not fully substituted with R1-R5 and Y0-Y4 are completed with an appropriate number of hydrogen atoms;

each R1, R2, R3, R4, R5, and R6 are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

Q0 is a residue selected from the group consisting of residues which are hydrophilic at physiologic pH and are at least partially positively charged at physiologic pH (e.g., amino, alkylamino, ammonium, alkylammonium, guanidine, imidazolyl, pyridyl, or the like); at least partially negatively charged at physiologic pH but undergo protonation at lower pH (e.g., carboxyl, sulfonamide, boronate, phosphonate, phosphate, or the like); substantially neutral (or non-charged) at physiologic pH (e.g., hydroxy, polyoxylated alkyl, polyethylene glycol, polypropylene glycol, thiol, or the like); at least partially zwitterionic at physiologic pH (e.g., a monomeric residue comprising a phosphate group and an ammonium group at physiologic pH); conjugatable or functionalizable residues (e.g. residues that comprise a reactive group, e.g., azide, alkyne, succinimide ester, tetrafluorophenyl ester, pentafluorophenyl ester, p-nitrophenyl ester, pyridyl disulfide, or the like); or hydrogen;

Q1 is a residue which is hydrophilic at physiologic pH, and is at least partially positively charged at physiologic pH (e.g., amino, alkylamino, ammonium, alkylammonium, guanidine, imidazolyl, pyridyl, or the like); at least partially negatively charged at physiologic pH but undergoes protonation at lower pH (e.g., carboxyl, sulfonamide, boronate, phosphonate, phosphate, or the like); substantially neutral at physiologic pH (e.g., hydroxy, polyoxylated alkyl, polyethylene glycol, polypropylene glycol, thiol, or the like); or at least partially zwitterionic at physiologic pH (e.g., a monomeric residue comprising a phosphate group and an ammonium group at physiologic pH);

Q2 is a residue which is positively charged at physiologic pH, including but not limited to amino, alkylamino, ammonium, alkylammonium, guanidine, imidazolyl, and pyridyl;

Q3 is a residue which is negatively charged at physiologic pH, but undergoes protonation at lower pH, including but not limited to carboxyl, sulfonamide, boronate, phosphonate, and phosphate;

m is a number ranging from equal to 0 to less than 1.0 (e.g., 0 to about 0.49);

n is a number ranging from greater than 0 to 1.0 (e.g., about 0.51 to about 1.0);

the sum of $(m+n)=1$ p is a number ranging from about 0.1 to about 0.9 (e.g., about 0.2 to about 0.5);

q is a number ranging from about 0.1 to about 0.9 (e.g., about 0.2 to about 0.5);

r is a number ranging from 0 to about 0.8 (e.g., 0 to about 0.6);

the sum of $(p+q+r)=1$;

v ranges about 5 to about 25 kDa; and, w ranges from about 5 to about 50 kDa.

In some embodiments, the number or ratio of monomeric residues represented by p and q are within about 30% of each other, about 20% of each other, about 10% of each other, or the like. In specific embodiments, p is substantially the same as q. In certain embodiments, at least partially charged generally includes more than a trace amount of charged species, including, e.g., at least 20% of the residues are charged, at least 30% of the residues are charged, at least 40% of the residues are charged, at least 50% of the residues are charged, at least 60% of the residues are charged, at least 70% of the residues are charged, or the like.

In certain embodiments, m is 0 and Q1 is a residue which is hydrophilic and substantially neutral (or non-charged) at physiologic pH. In some embodiments, substantially non-charged includes, e.g., less than 5% are charged, less than 3% are charged, less than 1% are charged, or the like. In certain embodiments, m is 0 and Q1 is a residue which is hydrophilic and at least partially cationic at physiologic pH. In certain embodiments, m is 0 and Q1 is a residue which is hydrophilic and at least partially anionic at physiologic pH. In certain embodiments, m is >0 and n is >0 and one of and Q0 or Q1 is a residue which is hydrophilic and at least partially cationic at physiologic pH and the other of Q0 or Q1 is a residue which is hydrophilic and is substantially neutral at physiologic pH. In certain embodiments, m is >0 and n is >0 and one of and Q0 or Q1 is a residue which is hydrophilic and at least partially anionic at physiologic pH and the other of Q0 or Q1 is a residue which is hydrophilic and is substantially neutral at physiologic pH. In certain embodiments, m is >0 and n is >0 and Q1 is a residue which is hydrophilic and at least partially cationic at physiologic pH and Q0 is a residue which is conjugatable or functionalizable residues. In certain embodiments, m is >0 and n is >0 and Q1 is a residue which is hydrophilic and substantially neutral at physiologic pH and Q0 is a residue which is conjugatable or functionalizable residues.

In preferred embodiments, one or more of the hydrophobic blocks of constituent block copolymers of the heterogeneous polymeric micelles can include, for example and without limitation, a polymer chain which is a random copolymer block represented by block formula 1, optionally with one or more counter-ions.

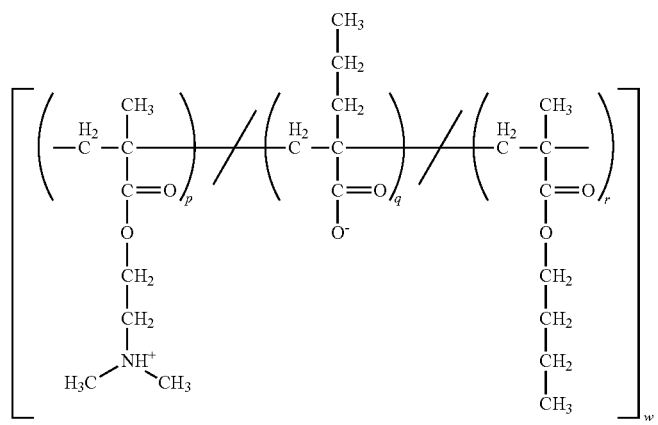

1

The constitutional units of block formula 1 can be derived from the polymerizable monomers N,N-dimethylaminoethylmethacrylate (DMAEMA, or alternatively referred to herein by shorthand notation "D"), propylacrylic acid (PAA, or alternatively referred to herein by shorthand notation "P") and butyl methacrylate (BMA, or alternatively referred to herein by shorthand notation "B"), represented respectively as follows:

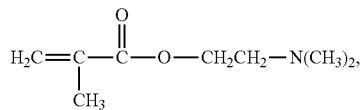
(D)

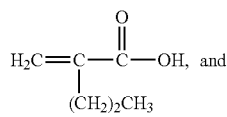
(P)

-continued

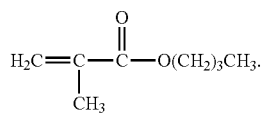
(B)

For the polymer block represented by block formula 1, p, q and r represent the mole fraction of each constitutional unit within the polymer chain, and can have the values described below.

One or more of the hydrophobic blocks of constituent first and second block copolymers of the heterogeneous polymeric micelles can be a chain of block formula 1, or can comprise a chain of block formula 1. For example, in one embodiment, the first and/or polymer can be a block copolymer comprising a hydrophobic block of formula 1 as a membrane disrupting polymer block and one or more additional blocks. Such a block copolymer can, for example, be a diblock copolymer represented by a polymer of formula 1.1

$$[A]v\text{-}[1]w \qquad 1.1$$

where [A] represents a second block (e.g., a hydrophilic block or an amphiphilic block), and the letters v and w represent the independently selected molecular weight (number average) of the respective blocks in the copolymer and can have the values described below. As another example, such a block copolymer can, for example, be a triblock copolymer represented by a polymer formula 1.2

$$[A]v\text{-}[A']x\text{-}[1]w \qquad 1.2$$

where [A] and [A'] each represent additional blocks (e.g., a hydrophilic block or an amphiphilic block), and the letters v, x and w each represent the independently selected molecular weight (number average) of the respective blocks in the copolymer and can have the values described below.

In a preferred, non-limiting example, a constituent first and/or second polymers of the heterogeneous polymeric micelle can be block copolymer having two or more blocks, including blocks having a structure represented as formula 2 follows (with appropriate counter-ions):

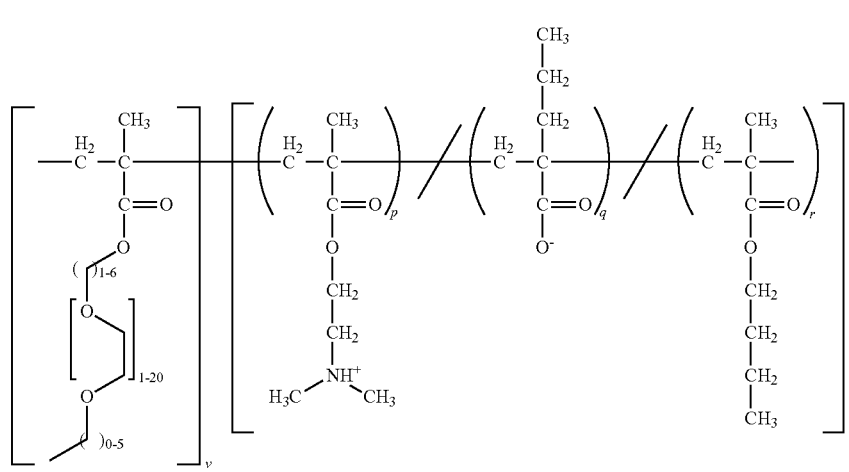
2

The constitutional units of compound 2 can be derived from polymerization of the polymerizable monomer O—(C$_1$-C$_6$ alkyl)polyethyleneglycol-methacyrlate (PEGMA) as a hydrophilic block and from the copolymerization of polymerizable monomers DMAEMA, PAA, and BMA, as described above in connection with polymer block 1 as a hydrophobic block. Letters p, q and r represent the mole fraction of each constitutional unit within the hydrophobic block and can have the values described below. The letters v and w represent the molecular weight (number average) of each block in the block copolymer and can have the values described below.

Preferred heterogeneous polymeric micelles can comprise two or more compositionally distinct block copolymers, each having two or more blocks, including a hydrophilic block and a hydrophobic block, and having a structure selected from block formulas 3, 4, 5, 6, 7, 8, and 9

$$[DMAEMA]_v\text{-}[B_p\text{-/-}P_q\text{-/-}D_r]_w \qquad 3$$

$$[PEGMA]_v\text{-}[B_p\text{-/-}P_q\text{-/-}D_r]_w \qquad 4$$

$[PEGMA_m\text{-}/\text{-}DMAEMA_n]_v\text{-}[B_p\text{-}/\text{-}P_q\text{-}/\text{-}D_r]_w$     5

$[PEGMA_m\text{-}/\text{-}MAA(NHS)_n]_v\text{-}[B_p\text{-}/\text{-}P_q\text{-}/\text{-}D_r]_w$     6

$[DMAEMA_m\text{-}/\text{-}MAA(NHS)_n]_v\text{-}[B_p\text{-}/\text{-}P_q\text{-}/\text{-}D_r]_w$     7

$[HPMA_m\text{-}/\text{-}PDSM_n]_v\text{-}[B_p\text{-}/\text{-}P_q\text{-}/\text{-}D_r]_w$     8

$[PEGMA_m\text{-}/\text{-}PDSM_n]_v\text{-}[B_p\text{-}/\text{-}P_q\text{-}/\text{-}D_r]_w$     9 where B is butyl methacrylate residue; P is propylacrylic acid residue; D, DMAEMA are each dimethylaminoethyl methacrylate residue; PEGMA is polyethyleneglycol methacrylate residue (e.g., with 1-20 ethylene oxide units, such as illustrated in compound 2, or 4-5 ethylene oxide units, or 7-8 ethylene oxide units); MAA(NHS) is methylacrylic acid-N-hydroxy succinimide residue; HPMA is N-(2-hydroxypropyl)methacrylamide residue; and PDSM is pyridyl disulfide methacrylate residue.

Generally, for each of the block copolymers comprising blocks of block formulas 1, 1.1, 1.2 and 2 through 9, each of m, n, p, q, r, w, x and v are numbers, as follows:

p is a number ranging from about 0.1 to about 0.9 (e.g., about 0.2 to about 0.5);

q is a number ranging from about 0.1 to about 0.9 (e.g., about 0.2 to about 0.5);

r is a number ranging from 0 to about 0.8 (e.g., 0 to about 0.6);

the sum of (p+q+r)=1;

v ranges about 5 to about 25 kDa; and, x ranges about 5 to about 25 kDa; and, w ranges from about 5 to about 50 kDa.

In some specific embodiments, the relative number-average molecular weight ratio of the hydrophobic block to hydrophilic block, represented in the aforementioned formulas as w:v ranges from about 1:2 to about 9:1, preferably from about 2:3 to about 7:1, preferably from about 2:3 to about 5:1, preferably from about 2:3 to about 4:1, preferably from about 1:1 to about 5:1, preferably from about 1:1 to about 4:1, preferably from about 1:1 to about 3:1 and in some embodiments from about 1:1 to about 2:1.

Constituent polymers comprising blocks of block formulas 1-9 are representative examples of polymers suitable for use in connection with the present invention. Other polymers can also be used, including structurally related polymers (such as variations in molecular weights and/or monomeric residue ratios). In some embodiments, the constitutional unit(s) of the first block (as shown) are controlled to effect a first block (as shown) which is or comprises a constitutional unit that is neutral (e.g., PEGMA), cationic (e.g., DMAEMA), anionic (e.g., PEGMA-NHS, where the NHS is hydrolyzed to the acid, or acrylic acid), ampholytic (e.g., DMAEMA-NHS, where the NHS is hydrolyzed to the acid), or zwitterrionic (for example, poly[2-methacryloyloxy-2'trimethylammoniumethyl phosphate]). In some embodiments, polymers comprising pyridyl disulfide functionality in the first block (as shown), e.g., [PEGMA-PDSM]-[B-P-D], that can be and is optionally reacted with a thiolated biomolecular agent such as a thiolated siRNA to form a polymer-siRNA conjugate.

Polymerization

Generally, the constituent block copolymers of the heterogeneous polymeric micelles of the invention, can be prepared in any suitable manner. Suitable synthetic methods used to produce the polymers provided herein include, by way of non-limiting example, cationic, anionic and free radical polymerization.

Preferably the polymers as described above are prepared by the means of a free radical polymerization. When a free radical polymerization process is used, (i) the monomer, (ii) optionally desired co-monomer(s), and (iii) an optional source of free radicals are provided to trigger a free radical polymerization process. In some embodiments, the source of free radicals is optional because some monomers may self-initiate upon heating at high temperature, or photo-activated. In certain instances, after forming the polymerization mixture, the mixture is subjected to polymerization conditions. Polymerization conditions are conditions under which at least one monomer forms at least one polymer, as discussed herein. Such conditions are optionally varied to suitable levels and include, by way of non-limiting example, temperature, pressure, atmosphere, ratios of starting components used in the polymerization mixture and reaction time. The polymerization is performed neat or in any suitable solvent, and can be carried out in any suitable manner, including, e.g., in solution, dispersion, suspension, emulsion or bulk.

In some embodiments, initiators are present in the reaction mixture. Any suitable initiator is optionally utilized if useful in the polymerization processes described herein. Such initiators include, by way of non-limiting example, one or more of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, or azo compounds. In specific embodiments, benzoylperoxide (BPO) and/or AIBN are used as initiators.

In some embodiments, polymerization is effected using a controlled (living) radical polymerization process. In preferred embodiments, reversible addition-fragmentation chain transfer (RAFT) approaches are used in synthesizing polymers from ethylenic monomers. RAFT comprises a free radical degenerative chain transfer process. In some embodiments, RAFT procedures for preparing a polymer described herein employs a chain transfer agent (CTA). Generally, polymers or polymer chains (e.g., polymer blocks) can be independently derived in a method comprising polymerizing in the presence of a reversible addition-fragmentation chain-transfer (RAFT) agent. Such RAFT agents can generally have the formula Y-RL, where RL is a leaving group, typically coupled to a chain-transfer moiety, Y, through a relatively weak covalent bond. Typically, Y can form a radical intermediate moiety, —Y.—, generated from or in the presence of a radical moiety (e.g., such as an initiator radical under initiation reaction conditions, or such as a propagating polymer chain radical, Pn. under radical polymerization conditions).

In generally preferred embodiments, the chain transfer agent (CTA) can comprise a thiocarbonylthio moiety. For example, the CIA can comprise a thiocarbonylthio moiety, —SC(=S)—, covalently bonded to an activating group, Z, and to a leaving group, —RL. Such CTA can be represented for example, by a compound having the formula RLSC(=S)Z.

Various such RAFT chain-transfer agents are known for use in controlled (living) radical polymerizations, including various xanthates, dithiocarbamates, diothioesters and trithiocarbonates.). See for example, Moad et al., The Chemistry of Radical Polymerization, 2d Ed., Tables 9.10 to 9.18 at pp. 508 to 514, Elsevier (2006), which is incorporated herein by reference. In many embodiments, the chain transfer agent (CTA) can be a macromolecular chain transfer agent (macro- CTA). For example, a chain-transfer moiety, Y, of a RAFT chain transfer agent can be incorporated onto the ω-end of a polymer chain, Pn, to form a macro-CTA comprising a polymer compound, and represented by a formula Pn-Y. (In such case, the polymer chain, Pn, can effectively function as a leaving group, RL, of the macromolecular chain transfer agent.). As incorporated into a compound of the invention, —Y, is referred to as a chain transfer residue. Hence, in the context of compounds of the invention derived from radical polymerization, —Y can be a chain-transfer residue. The chain transfer residue can be derived from controlled (living) radical polymerization of under chain polymerization conditions. Such controlled radical polymerization reactions can be effected for example in the presence of a chain transfer agent (CTA) such as a RAFT agent (e.g., Y—RL) or such as a macro-CTA (e.g., Pn-Y). The chain-transfer residue, —Y, is typically covalently bonded to a polymer on the ω-end thereof (also referred to as the living end of the chain extension moiety when included in a macro CTA). The chain transfer residue, —Y, can preferably be a thiocarbonylthio moiety having a formula —SC(=S)Z, where Z is an activating group.

Various approaches are known for cleaving and/or derivatizing the chain transfer residue, Y, to form a chain transfer residue derivative. See for example, Moad et al., The Chemistry of Radical Polymerization, 2d Ed., pp. 538 to 539, Elsevier (2006), which is incorporated herein by reference. See also U.S. Pat. No. 6,619,409 to Charmot et al., which discloses cleavage of the thiocarbonylthio control transfer agent. Derivatized chain transfer residues, can be used for effectively coupling one or more biomolecular agents such as a polynucleotide to the polymer, optionally through a linking moiety.

Although RAFT agents are preferably employed, other controlled (living) radical polymerization methods are also suitable in connection with the invention. See for example, Moad et al., The Chemistry of Radical Polymerization, Elsevier (2006), which is incorporated herein by reference. In particular, atom transfer radical polymerization (ATRP) and stable free radical polymerization (SFRP) approaches are suitable. See Moad et al., Id.

Polymerization processes are carried out in a living mode, in any suitable manner, such as but not limited to Atom Transfer Radical Polymerization (ATRP), nitroxide-mediated living free radical polymerization (NMP), ring-opening polymerization (ROP), degenerative transfer (DT), or Reversible Addition Fragmentation Transfer (RAFT). Using conventional and/or living/controlled polymerizations methods, various polymer architectures can be produced, such as but not limited to block, graft, star and gradient copolymers, whereby the monomer units are either distributed statistically or in a gradient fashion across the chain or homopolymerized in block sequence or pendant grafts.

Generally, constituent polymers or blocks thereof can have a low polydispersity index (PDI) or differences in chain length. Polydispersity index (PDI) can be determined in any suitable manner, e.g., by dividing the weight average molecular weight of the polymers by their number average molecular weight. Polydispersity values approaching one are achievable using radical living polymerization. Methods of determining molecular weight and polydispersity, such as, but not limited to, size exclusion chromatography, dynamic light scattering, matrix-assisted laser desorption/ionization chromatography and electrospray mass chromatography are well known in the art. In some embodiments, block copolymers of the polymeric compounds provided herein have a polydispersity index (PDI) of less than 2.0, or less than 1.5, or less than 1.4, or less than 1.3, or less than 1.2

Generally, polymerization processes described herein optionally occur in any suitable solvent or mixture thereof. Suitable solvents include water, alcohol (e.g., methanol, ethanol, n-propanol, isopropanol, butanol), tetrahydrofuran (THF) dimethyl sulfoxide (DMSO), dimethylformamide (DMF), acetone, acetonitrile, hexamethylphosphoramide, acetic acid, formic acid, hexane, cyclohexane, benzene, toluene, dioxane, methylene chloride, ether (e.g., diethyl ether), chloroform, and ethyl acetate. In one aspect, the solvent includes water, and mixtures of water and water-miscible organic solvents such as DMF.

Generally, polymerization processes described herein can be effected at temperature effective for the polymerization reaction. Temperatures can be varied based on and in consideration of other reaction aspects, including for example selections as to solvent, monomer (or comonomers) being polymerized (or copolymerized), chain transfer agent, heat transfer (exotherm control), reaction kinetics, and reaction thermodynamics. Typical temperature ranges can generally include a temperature ranging from about 2° C. to about 200° C., preferably from about 20° C. to about 110° C., and in some embodiments from from about 40° C. to about 90° C., and or from about 50° C. to about 80° C.

Generally, polymerization processes described herein can be effected at a pressure effective for the polymerization reaction. Generally, reaction pressure is not narrowly critical, and can be at ambient pressure of about 1 atm or at higher pressures (e.g., ranging from 1 atm to about 10 atm) or a lower pressure (e.g., below 1 atm).

Generally, polymerization processes described herein can be effected under a reaction atmosphere effective for the polymerization reaction. For example, polymerization can be effected under an inert gas atmosphere (e.g., Ar, N2), or under ambient atmosphere.

Generally, polymerization processes described herein can be effected at various molar ratios of chain transfer agent (living chain transfer moieties or groups) to monomer effective for the polymerization reaction. For example, polymerization can be effected with a molar ratio of chain transfer agent (groups) to monomer ranging from about 1:1 to about 1:10,000, preferably from about 1:5 to about 1:5000, and most preferably from about 1:10 to about 1:2000 In some embodiments, the molar ratio can range from about 1:10 to about 1:1500.

Generally, polymerization processes described herein can be effected at concentrations of monomer(s) in the solvent ranging from about 5% to about 95% by weight, preferably from about 10% to about 90% solids, by weight, and in some embodiments, from about 20% to about 80% solids, by weight, in each case relative to total weight of solution.

Generally, polymerization processes described herein can be effected at various molar ratios of chain transfer agent (living chain transfer moieties or groups) to initiator effective for the polymerization reaction. For example, polymerization can be effected with a molar ratio of chain transfer agent (groups) to initiator ranging from about 1:2 to about 50:1, and preferably from about 1:1 to about 40:1, and in some embodiments from about 2:1 to about 30:1.

Generally, polymerization processes described herein can be effected for various reaction times effective for the polymerization reaction. For example, the polymerization can be effected over a reaction time period ranging from about 0.5 hr to about 96 hr, preferably from about 1 hour to about 72 hours, more preferably from about 1 hour to 36 hours, and in some embodiments from about 2 hours to 24 hours, or from about 3 hours to about 12 hours.

Generally, the aforementioned aspects and other factors known in the art can be used to effect the polymerization reaction of interest. See generally, for example, Moad et al., The Chemistry of Radical Polymerization, 2d Ed., Elsevier (2006), which is incorporated herewith in this regard.

Polynucleotide-Containing Compositions

Generally, a polynucleotide-containing composition can comprise a heterogeneous polymeric micelle and a polynucleotide associated with the micelle.

Generally, one or more of the constituent polymers of the heterogeneous polymeric micelles—or certain blocks of such polymers, can associate polynucleotides. Preferably, the polynucleotide associates non-covalently (e.g., ionically) or through a covalent linking moiety with one or more of the polymers, and preferably through a hydrophilic block of the first and/or second polymer.

An agent such as a polynucleotide can be associated non-covalently to at least one of the first and second constituent polymers of the heterogeneous polymeric micelle. Non-covalent association can include electrostatic interaction (ionic association), hydrophobic interaction, affinity interaction, or a combination thereof. In certain embodiments, the constituent polymers of the heterogeneous polymeric micelle and/or the agent can be provided with chemical moieties that can effect such non-covalent interaction. For example, constituent polymers can comprise monomeric residues which are cationic—for effecting ionic association with negatively-charged agents such as polynucleotides. For example, constituent polymers can comprise monomeric residues having a specie which is a member of an affinity pair or which is covalently coupled (e.g., through a conjugatable pendant moiety) to a member of an affinity pair (e.g., an antibody) having affinity for an agent to be delivered intracellularly, or for example, having affinity for another member of the affinity pair which is covalently coupled to the agent (e.g, an epitope). Affinity pairs are known, and can include those such as arylboronic acid-salicylhydroxamic acid, leucine zipper or other peptide motifs. Moieties (e.g., polymerizable monomers) for effecting ionic interactions between positive/negative charges on the constituent polymer/agent are also known, and are discussed herein in connection with polymer sections. Other types of non-covalent chemical affinity linkages are likewise known in the art. Additionally, in some embodiments, a double-stranded polynucleotide is associated with (e.g., complexed to) a polymer or heterogeneous polymeric micelle. In some embodiments, a polymer or heterogeneous polymeric micelle is associated (e.g., complexed) with a nucleic acid minor groove binding agent or an intercalating agent that is attached (e.g., covalently) to a component (e.g., a polymer) of the heterogeneous polymeric micelle.

In one approach, for example, polynucleotides can be associated through ionic interactions with one or more of the constituent polymers, or a block thereof. Preferably, a polynucleotide is associated with a block other than the hydrophobic block which defines the core of the heterogeneous micelle. With reference to FIG. 1C, for example, a heterogeneous polymeric micelle $M^7$ comprises two or more compositionally distinct polymers, including a first polymer, $P^1$, and a second polymer, $P^2$, compositionally distinct from the first polymer $P^1$. The first polymer is a block copolymer comprising a hydrophilic block and a hydrophobic block. The hydrophilic block comprises a plurality of cationic monomeric residues in ionic association with the polynucleotide. The second polymer is a block copolymer comprising a hydrophilic block and a hydrophobic block, with the hydrophobic block of the second polymer associating with the hydrophobic block of the first polymer to form a stable heterogeneous micelle (e.g., in an aqueous medium at pH 7.4). In this embodiment, preferably at least one of the hydrophilic block or the hydrophobic block of the first polymer, and additionally or alternatively, at least one of the hydrophilic block or the hydrophobic block of the second polymer is a random copolymer block comprising two or more compositionally distinct monomeric residues.

In this ionic association approach, the hydrophilic block of the first polymer and/or the second polymer can preferably further comprise a plurality of cationic monomeric residues, preferably cationic hydrophilic monomeric residues. The cationic monomeric residues can selected especially as described in connection with the hydrophilic block, generally. As a non-limiting example, the first polymer and/or the second polymer can comprise a block copolymer comprising a cationic hydrophilic block and a membrane destabilizing block, represented for example by block formula 3,

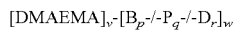
$$[\text{DMAEMA}]_v\text{-}[\text{B}_p\text{-/-}\text{P}_q\text{-/-}\text{D}_r]_w \quad\quad 3$$

which is more fully described earlier in the section directed to preferred polymers.

In some alternative embodiments of this ionic association approach, the hydrophilic block of the first polymer and/or the second polymer can comprise a plurality of cationic monomeric residues and a plurality of neutral (non-charged) monomeric residues. In such embodiments, for example, the hydrophilic block of the first polymer and/or the second polymer can preferably be charge modulated (e.g., charge diluted)—being substantially overall cationic in overall charge. As a non-limiting example, the first polymer and/or the second polymer can comprise a block copolymer comprising a hydrophilic block and a membrane destabilizing hydrophobic block, where the hydrophilic block comprises cationic hydrophilic monomeric residues and neutral hydrophilic monomeric residues, represented for example by block formula 5,

$$[\text{PEGMA}_m\text{-/-}\text{DMAEMA}_n]_v\text{-}[\text{B}_p\text{-/-}\text{P}_q\text{-/-}\text{D}_r]_w \quad\quad 5$$

which is more fully described earlier in the section directed to preferred polymers.

In an alternative approach for effecting both polynucleotide ionic association as well as charge modulation, a cationic charge is achieved on a hydrophilic block of a first polymer, and non-charged neutral "charge diluent" is achieved on a hydrophilic block of the second polymer. As a non-limiting example, the first polymer can comprise a block copolymer comprising a cationic hydrophilic block and a membrane destabilizing hydrophobic block, where the hydrophilic block comprises cationic hydrophilic monomeric residues, represented for example by block formula 3. The second polymer can comprise a block copolymer comprising a neutral hydrophilic block and a membrane destabilizing hydrophobic block, where the hydrophilic block comprises neutral hydrophilic monomeric residues, represented for example by block formula 4

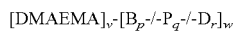
$$[\text{DMAEMA}]_v\text{-}[\text{B}_p\text{-/-}\text{P}_q\text{-/-}\text{D}_r]_w \quad\quad 3$$

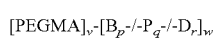
$$[\text{PEGMA}]_v\text{-}[\text{B}_p\text{-/-}\text{P}_q\text{-/-}\text{D}_r]_w \quad\quad 4$$

each of which is more fully described earlier in the section directed to preferred polymers.

Generally, in embodiments in which the agent is a polynucleotide, the composition can comprise a heterogeneous polymeric micelle and a polynucleotide associated with the micelle through ionic interactions. The association (e.g., complex) between the heterogeneous polymeric micelle and the polynucleotide agent (e.g., oligonucleotide or siRNA) can be effected at various desired charge ratios of (e.g. total charge or charge density on the) constituent polymer to (e.g., total charge or charge density on the) polynucleotide, including for example a charge ratio ranging from 1:2 to 32:1, and preferably ranging from 1:1 to 16:1. In specific embodiments, the complex between the heterogeneous polymeric micelle and polynucleotide (e.g., siRNA) can include a charge ratio of ranging from 2:1 to 8:1, or from 3:1 to 6:1, and in some embodiments can be about 4:1. In preferred embodiments therefore, the ratio of the number of cationic charges present in the shell region of the heterogeneous polymeric micelle to the number of anionic charges present in the agent to be delivered to the cell (e.g., polynucleotide agent) can range from about 1:2 to about 32:1, from about 1:1 to about 16:1, from about 2:1 to about 8:1, from about 3:1 to about 6:1, and in some cases can range from about 4:1 to about 12:1, about 2:1, about 4:1, or about 8:1. In some embodiments, an anionic agent (e.g., a polynucleotide) can be charge-neutralized by a polycationic block of a block copolymer forming the heterogeneous polymeric micelle. For example, in some non-limiting examples, a 20-base pair polynucleotide (e.g., oligonucleotide or siRNA) comprising about 40 negative charges at physiologic pH can be associated (e.g., complexed) with a heterogeneous polymeric micelle (e.g., micelle) comprising a cationic hydrophilic block—e.g., polyDMAEMA, about 80 monomeric units in length, MW=11,680, with a pKa of about 7.4. At this pH, polyDMAEMA contains about 40 negative charges, thereby resulting in a polynucleotide-shell block association (e.g., complex) that is substantially net neutral in overall charge. In certain instances, avoiding a large number of excess positive charges helps to reduce in vitro and in vivo toxicity. In some embodiments, a therapeutic agent (e.g., oligonucleotide or siRNA) spontaneously associates with a positively charged shell of a heterogeneous polymeric micelle (e.g., micelle) provided herein.

Alternatively, an agent such as a polynucleotide can be covalently associated with the heterogeneous polymeric micelle.

In some embodiments, an agent such as a polynucleotide is chemically conjugated to a constituent polymer of the heterogeneous polymeric micelle or to a block thereof. Agents can be conjugated pendant to a side chain of the polymer, or to an end (e.g., alpha end or omega end) of the polymer, in each case for example through a conjugatable moiety of a polymeric residue (including residues of control agents or other polymerization reagents), and in each case, optionally through a linking moiety.

Generally, the particular approach for effecting conjugated polynucleotides is not narrowly critical. In some embodiments, agents such as polynucleotides can be conjugated to already-formed heterogeneous polymeric micelle. Alternatively, agents such as polynucleotides can be conjugated with a constituent polymer before forming the heterogeneous polymeric micelle. The covalent bond between a constituent polymer and an agent can be non-cleavable or cleavable. Cleavable bonds can include for example, disulfide bonds (e.g., disulfide bonds that are cleaved in the reducing environment of the cytoplasm). Suitable chemical conjugation methods can include, without limitation, amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In some embodiments, conjugation is also performed with pH-sensitive bonds and linkers, including, but not limited to, hydrazone and acetal linkages. A variety of other conjugation chemistries are available (see, for example, Bioconjugation, Aslam and Dent, Eds, Macmillan, 1998 and chapters therein).

Polynucleotides can be associated through covalent conjugation to one or more of the constituent polymers, optionally through a linking moiety. Covalent conjugation can be preferably effected, for example, through a monomeric residue having a conjugatable species (i.e., reactive functional group moiety). With reference again to FIG. 1C, for example, a heterogeneous polymeric micelle $M^{10}$ comprises two or more compositionally distinct polymers, including a first polymer, $P^1$, and a second polymer, $P^2$, compositionally distinct from the first polymer $P^1$. The first polymer is a block copolymer comprising a hydrophilic block and a hydrophobic block. A polynucleotide is covalently coupled to the hydrophilic block of the first polymer, preferably through a pendant moiety of a monomeric residue of the hydrophilic block, thereby forming a polymer bioconjugate. The second polymer is a block copolymer comprising a hydrophilic block and a hydrophobic block. The hydrophobic block of the second polymer associates with the hydrophobic block of the first polymer to form a stable heterogeneous micelle (e.g., in an aqueous medium at pH 7.4).

Generally for such approach, the first polymer is covalently coupled to the 3' end of the polynucleotide, or alternatively, to the 5' end of the polynucleotide.

Generally for such approach, the polynucleotide can be linked to the polymeric micelle or a constituent polymer thereof through a linking moiety. A linking moiety is more fully described below, and can generally comprise a covalent bond, or a moiety derived from a multifunctional moiety comprising two or more reactive functional groups. The linking moiety can be a pH-sensitive labile moiety. The linking moiety is preferably stable at serum pH and acid labile at endosomal pH. The linking moiety can be a disulfide.

As a non-limiting example, a polynucleotide is covalently coupled to the hydrophilic block of the first polymer, preferably through a pendant moiety of a monomeric residue of the hydrophilic block. The first polymer can comprise a block copolymer comprising a hydrophilic block, and a membrane destabilizing hydrophobic block, where the hydrophilic block comprises a monomeric residue having a conjugatable moiety, represented for example by one (or more) of block formulas 6, 7, 8 or 9. The second polymer can comprise a block copolymer comprising a neutral hydrophilic block and a membrane destabilizing hydrophobic block, where the hydrophilic block comprises neutral hydrophilic monomeric residues, represented for example by block formula 4.

$[PEGMA]_v\text{-}[B_p\text{-}/\text{-}P_q\text{-}/\text{-}D_r]_w$     4

$[PEGMA_m\text{-}/\text{-}MAA(NHS)_n]_v\text{-}[B_p\text{-}/\text{-}P_q\text{-}/\text{-}D_r]_w$     6

$[DMAEMA_m\text{-}/\text{-}MAA(NHS)_n]_v\text{-}[B_p\text{-}/\text{-}P_q\text{-}/\text{-}D_r]_w$     7

$[HPMA_m\text{-}/\text{-}PDSM_n]_v\text{-}[B_p\text{-}/\text{-}P_q\text{-}/\text{-}D_r]_w$     8

$[PEGMA_m\text{-}/\text{-}PDSM_n]_v\text{-}[B_p\text{-}/\text{-}P_q\text{-}/\text{-}D_r]_w$     9 each of which is more fully described earlier in the section directed to preferred polymers.

In a further approach, a polynucleotide can be associated with the heterogeneous polymeric micelle by covalent conjugation to an end of one of the polymers, allowing such polynucleotide to essentially constitute and define the hydrophilic block of an end-conjugated polymer comprising the hydrophobic block thereof. With further reference to FIG. 1C, for example, a heterogeneous polymeric micelle $M^8$ comprises two or more compositionally distinct polymers, including a first polymer, $P^1$, and a second polymer, $P^2$, compositionally distinct from the first polymer $P^1$. The first polymer is a block copolymer comprising the polynucleotide covalently end-linked to the hydrophobic block, through a linking moiety, such that the polynucleotide essentially defines the hydrophilic block. The second polymer is compositionally distinct from the first polymer, and is a block copolymer comprising a hydrophilic block and a hydrophobic block. The hydrophobic block of the second polymer associates with the hydrophobic block of the first polymer to form a stable heterogeneous micelle (e.g., in an aqueous medium at pH 7.4).

Referring again to FIG. 1C, for example, a heterogeneous polymeric micelle $M^9$ comprises two or more compositionally distinct polymers, including a first polymer, $P^1$, and a second polymer, $P^2$, compositionally distinct from the first polymer $P^1$. The first polymer is a block copolymer comprising a hydrophobic block and a hydrophilic block, with the polynucleotide covalently end-linked to the hydrophilic block, through a linking moiety, such that taken together, the polynucleotide and the hydrophilic block can each essentially be or define the hydrophilic block. The second polymer is compositionally distinct from the first polymer, and is a block copolymer comprising a hydrophilic block and a hydrophobic block. The hydrophobic block of the second polymer associates with the hydrophobic block of the first polymer to form a stable heterogeneous micelle (e.g., in an aqueous medium at pH 7.4).

Generally for such approach, the first polymer is covalently coupled to the 3' end of the polynucleotide, or alternatively, to the 5' end of the polynucleotide.

Generally for such approach, the polynucleotide can be linked to the polymeric micelle or a constituent polymer thereof through a linking moiety. A linking moiety is more fully described below, and can generally comprise a covalent bond, or a moiety derived from a multifunctional moiety comprising two or more reactive functional groups. The linking moiety can be a pH-sensitive labile moiety. The linking moiety is preferably stable at serum pH and acid labile at endosomal pH. The linking moiety can be a disulfide.

In embodiments involving conjugation of a polynucleotide to a constituent polymer of the heterogeneous polymeric micelle, one exemplary approach can include a process comprising: (1) activating a modifiable end group (for example, 5'- or 3'-hydroxyl or) of an oligonucleotide using any suitable activation reagents, such as but not limited to 1-ethyl-3,3-dimethylaminopropyl carbodiimide (EDAC), N-hydrosuccinimide (NHS) and dicyclohexylcarbodiimide (DCC), HOBt (1-hydroxybenzotriazole), p-nitrophenylchloroformate, carbonyldiimidazole (CDI), and N,N'-disuccinimidyl carbonate (DSC); and (2) covalently linking a block copolymer to the end of the oligonucleotide. In some embodiments, the 5'- or 3'-end modifiable group of an oligonucleotide is substituted by other functional groups prior to conjugation with the block copolymer. For example, hydroxyl group (—OH) is optionally substituted with a linker carrying sulfhydryl group (—SH), carboxyl group (—COOH), or amine group (—NH$_2$). In another exemplary approach, an oligonucleotide comprising a functional group introduced into one or more of the bases (for example, a 5-aminoalkylpyrimidine), can be conjugated to a constituent polymer (e.g., block copolymer), wherein the polymer is a unimer or present in a heterogeneous polymeric micelle, provided herein using an activating agent or a reactive bifunctional linker according to any suitable procedure. A variety of such activating agents and bifunctional linkers is available commercially from such suppliers as Sigma, Pierce, Invitrogen and others.

Generally, each of the aforedescribed polynucleotide-containing composition can further comprise one or more polymers having a shielding moiety or species. For example, a heterogeneous polymeric micelle and a polynucleotide associated with the micelle can comprise a plurality of monomeric residues having a shielding species, as more fully described in a following section.

Generally, each of the aforedescribed polynucleotide-containing composition can further comprise one or more polymers having a targeting moiety or species. For example, a heterogeneous polymeric micelle and a polynucleotide associated with the micelle can comprise a plurality of monomeric residues having a conjugatable species, for covalently linking a targeting moiety (e.g., a targeting ligand), as more fully described in a following section.

Advantageously, heterogeneous polymeric micelles can be realized having (i) controllably varied (tunable) block copolymer composition (e.g., as compared between first and second polymers or blocks thereof, such as hydrophilic blocks thereof), (ii) controllably varied (tunable) relative molecular weight ratios of hydrophilic block and hydrophobic blocks (e.g., as compared between first and second polymer), and derivatively, controllably varied (tunable) relative block molecular weights (e.g., hydrophilic block lengths) as compared between corresponding blocks of two or more polymers), (iii) controllably varied (tunable) total molecular weights of polymers (e.g., resulting in varied relative total chain lengths as compared between two or more polymers), and (iv) controllably varied (tunable) relative ratios of the amount (i.e., moles) of the first block copolymer to the second block copolymer and/or additional (block co)polymers. Such controlled variability can be used for example to provide for optimization of micelle properties (e.g., aggregation number, particle size, surface charge, solubility, etc.) and desirable functions, such as optimization of shielding, and/or optimization of targeting, and/or optimization of (reduced) toxicity profile, and/or optimization of pharmacokinetic properties and/or optimization of (a desired) biodistribution profile, among others. Such parameters and others can be important for effective use as polymeric micelle delivery vehicles for delivery of agents such as polynucleotides (e.g., siRNA) for therapeutic or other purposes.

Generally, for example, various selected ratios of the first block copolymer to the second block copolymer can be effected in the heterogeneous polymeric micelles. For example, the relative ratio of a first polymer to a second polymer can be controllably varied to achieve, in combination with variation in the composition of such polymers, a desired set of chemical or physical properties of the micelle. As a non-limiting example, a heterogeneous (mixed) polymeric micelle can be formed from two or more block copolymers—having compositionally distinct hydrophilic blocks and each having substantially the same hydrophobic block—e.g., as a membrane destabilizing block. Specifically, for example, a first block copolymer can have a hydrophilic block consisting essentially of a cationic hydrophilic monomeric residue (e.g., DMAEMA), and a second block copolymer can have a hydrophilic block consisting essentially of a neutral hydrophilic monomeric residue (e.g., PEGMA). Such first and second polymers can be combined at various desired molar ratios (e.g., 2:1, 1:1, 1:2) to form a heterogeneous micelle having a hydrophilic shell with corresponding relative cationic charge.

In this example, charge is being modulated by varying the relative amount of cationic shell blocks versus neutral shell blocks of the micelle.

Generally, and without limitation, relative molecular weights, number of monomeric units, and compositions of the blocks within a given first polymer copolymer or a second block copolymer can be varied to achieve micelle stability and biological functionality.

In some embodiments, it is generally preferably to prepare a mixed micelle containing two block copolymers having substantially the same hydrophobic blocks (e.g., membrane destabilizing hydrophobic blocks) and having compositionally distinct hydrophilic blocks—for example, one hydrophilic block comprising monomeric units effecting one (set of) functional features or attributes, and the other hydrophilic block comprising monomeric units effecting another (set of) (same, additive or different, orthogonally complementary) functional features or attributes. For example, one hydrophilic block (e.g., of a first polymer) can effect polynucleotide association (e.g., covalent or ionic), and the other hydrophilic block (e.g., of a second polymer) can effect shielding and/or targeting or other functions.

With reference to FIG. 1F, generally for example, preferred polynucleotide-containing compositions can comprise a heterogeneous polymeric micelle (e.g., $M^{7G}$, $M^{7H}$, $M^{7I}$, $M^{10G}$ $M^{10H}$, and $M^{10I}$)) and a polynucleotide associated therewith. Each such micelle can comprise two or more compositionally distinct polymers, including a first polymer, $P^1$, and a second polymer, $P^2$, compositionally distinct from the first polymer $P^1$. The first polymer is a block copolymer comprising a hydrophilic block and a hydrophobic block (e.g., a membrane destabilizing hydrophobic block). A polynucleotide is associated with the hydrophilic block of the first polymer (e.g., through ionic association ($M^{7G}$, $M^{7H}$, $M^{7I}$) or through covalent pendant coupling ($M^{10G}$, $M^{10H}$, $M^{10I}$)). The second polymer is a block copolymer comprising a hydrophilic block and a hydrophobic block (e.g., a membrane destabilizing hydrophobic block). The hydrophobic block of the second polymer associates with the hydrophobic block of the first polymer to form a stable heterogeneous micelle (e.g., in an aqueous medium at pH 7.4).

Among the various depicted embodiments, the hydrophilic blocks of the first polymer, $P^1$, and a second polymer, $P^2$, can provide polynucleotide-associating, shielding and/or targeting functionality.

For embodiments involving ionic association of the polynucleotide ($M^{7G}$, $M^{7H}$, $M^{7I}$), the hydrophilic block of the first polymer, $P^1$, can comprise a plurality of cationic monomeric residues for ionic association with the polynucleotide. Shielding can be provided for example through the hydrophilic block of the second polymer ($M^{7G}$, $M^{7H}$, $M^{7I}$) and/or the hydrophilic block of the first polymer ($M^{7I}$), for example where such hydrophilic blocks comprise monomeric residues having a shielding agent, S, such as pendant group comprising a shielding oligomer or polymer. Targeting can be provided, for example, through the hydrophilic block of the second polymer ($M^{7H}$) and/or through the hydrophilic block of a third polymer, $P^3$,($M^{7I}$), for example where such hydrophilic blocks comprise monomeric residues having a conjugatable species for covalently linking a targeting agent, T, for example as a ligand for mediating endocytosis.

For embodiments involving covalent coupling of the polynucleotide ($M^{10G}$, $M^{10H}$, $M^{10I}$) the hydrophilic block of the first polymer, $P^1$, can comprise a plurality of monomeric residues having a conjugatable species for covalently coupling the polynucleotide through a linking moiety, L. Shielding can be provided for example through the hydrophilic block of the second polymer ($M^{10G}$, $M^{10H}$, $M^{10I}$) and/or the hydrophilic block of the first polymer ($M^{10G}$, $M^{10H}$, $M^{10I}$), for example where such hydrophilic blocks comprise monomeric residues having a shielding agent, S, such as pendant group comprising a shielding oligomer or polymer. Targeting can be provided, for example, through the hydrophilic block of the second polymer ($M^{10H}$) and/or through the hydrophilic block of a third polymer, $P^3$,($M^{10I}$), M) for example where such hydrophilic blocks comprise monomeric residues having a conjugatable species for covalently linking a targeting agent, T, for example, as a ligand for mediating endocytosis.

Numerous other permutations can be realized for integrating various desired functional features and attributions for a application of interest. The aforedescribed embodiments are illustrative, and not limiting on the scope of the invention except to the extent specifically claimed.

Polynucleotides

Preferred compositions of the invention comprise a heterogeneous polymeric micelle and a polynucleotide associated therewith. Generally, the polynucleotide can be a polynucleic acid. In certain embodiments, the polynucleotide can be a therapeutic (including prophylactic) agent, a diagnostic agent or a research reagent.

In preferred embodiments, the polynucleotide can be an oligonucleotide, a gene expression modulator, a knockdown agent, an siRNA, an RNAi agent, a dicer substrate, an miRNA, an shRNA, an antisense oligonucleotide, or an aptamer. In other specific embodiments, the therapeutic agent is an aiRNA (Asymmetric RNA duplexes mediate RNA interference in mammalian cells. Xiangao Sun, Harry A Rogoff, Chiang J Li *Nature Biotechnology* 26, 1379-1382 (2008)).

A polynucleotide is a nucleic acid polymer. A polynucleotide can be an oligonucleotide. In some embodiments, the polynucleotide can comprise between about 7 to about 200 nucleotide monomeric units. A polynucleotide can include single stranded nucleic acid polymers, as well as double stranded nucleic acid polymers, or higher-ordered (e.g., triple-stranded) nucleic acid polymers. A polynucleotide can be a ribonucleic acid (RNA) polymer. A polynucleotide can be a deoxyribonucleic acid (DNA) polymer.

A polynucleotide as referred to herein (or related terms "nucleotide", "nucleic acid," "DNA," "RNA," and/or similar terms) includes nucleic acid analogs—e.g., analogs of a nucleic acid polymer having a modified backbone, including but not limited to peptide nucleic acids (PNA), locked nucleic acids (LNA), phosphono-PNA, morpholino nucleic acids, or nucleic acids with modified phosphate groups (e.g., phosphorothioates, phosphonates, 5'-N-phosphoramidite linkages).

A polynucleotide can comprise a plurality of residues derived from (e.g., stepwise) coupling of nucleotide monomeric units. Nucleotide monomeric unts are phosphorylated nucleosides. A nucleoside can comprise a monosaccharide (e.g., pentose, hexose) and a base, monosaccharide mimetics and monosaccharides analogs, including for example monosaccharides modified by substituting hydroxyl groups with halogens, methoxy, hydrogen or amino groups, or by esterification of additional hydroxyl groups. In some embodiments, a nucleotide is or comprises a natural nucleoside phosphate (e.g. adenosine, thymidine, guanosine, cytidine, uridine, deoxyadenosine, deoxythymidine, deoxyguanosine, and deoxycytidine phosphate). In some embodiments, the base includes any bases occurring naturally in various nucleic acids as well as other modifications which are analogs of and/or which mimic or otherwise structurally and/or functionally resemble such naturally occurring bases. Nonlimiting examples of modified or derivatized bases include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, 2-aminoadenine, pyrrolopyrimidine, and 2,6-diaminopurine. Nucleoside bases also include universal nucleobases such as difluorotolyl, nitroindolyl, nitropyrrolyl, or nitroimidazolyl. Nucleotides also include nucleotides which harbor a label or contain abasic, i.e. lacking a base, monomers. A nucleic acid sequence is presented in the 5' to 3' direction unless otherwise indicated.

RNA interference (RNAi) refers to sequence-specific inhibition of gene expression and/or reduction in target messenger RNA, mRNA, and protein levels mediated by an at least partially double-stranded RNA, which also comprises a portion that is substantially complementary to a target RNA. An interfering RNA agent, or an RNAi agent refers to an oligonucleotide which mediates inhibition of gene expression through an RNAi mechanism and includes but is not limited to siRNA, microRNA (miRNA), short hairpin RNA (shRNA), asymmetrical interfering RNA (aiRNA), dicer substrate and the precursors thereof Short interfering RNA (siRNA) refers to an RNAi agent comprising a nucleotide duplex that is approximately 15-50 base pairs in length and optionally further comprises zero to two single-stranded overhangs. One strand of the siRNA includes a portion that hybridizes with a target RNA in a complementary manner. In some embodiments, one or more mismatches between the siRNA and the targeted portion of the target RNA may exist. In some embodiments, siRNAs mediate inhibition of gene expression by causing degradation of target transcripts.

Generally, nucleotides can be obtained from natural sources, produced using recombinant expression systems and optionally purified, chemically synthesized, etc.

Specific polynucleotides, and particular applications for polynucleotide-containing compositions are described more fully below, in the sections generally directed to biomolecular agents and therapeutic uses.

Shielding Agents

Generally, one or more of the constituent polymers of the heterogeneous polymeric micelles—or blocks of such polymers can comprise one or more shielding agent and/or solubilizing agent. The shielding agent can be effective for improving solubility of the polymer chain and can be effective for steric shielding of a therapeutic agent (e.g., polynucleotide, peptide, etc.). The shielding agent can also be effective for enhancing the stability of the therapeutic agent (e.g., polynucleotide or peptide, etc.) against enzymatic digestion in plasma. The shielding agent can also be effective for reducing toxicity of the certain compositions (e.g., compositions comprising polynucleotides). In some embodiments, the shielding agent can be a polymer comprising a plurality of neutral hydrophilic monomeric residues. The shielding polymer can be covalently coupled to a membrane destabilizing polymer, directly or indirectly, through an end group of the polymer or through a pendant functional group of one or more monomeric residues of the polymer. In some embodiments, a plurality of monomeric residues of the polymer chain can have a shielding species; preferably, such shielding species is a pendant moiety from a polymerizable monomer (from which the shielding monomeric residues are derived). For example, the polymer can comprise a plurality of monomeric residues having a pendant group comprising a shielding oligomer.

A preferred shielding/solubilizing polymer can be a polyethylene glycol (PEG) oligomer (e.g., having 20 or less repeat units) or polymer (e.g., having more than 20 repeat units). In certain embodiments, one block of a block copolymer can be or comprises a polyethylene glycol (PEG) oligomer or polymer—for example, covalently coupled to the alpha end or the omega end of the membrane destabilizing block of the copolymer. In another embodiment, a polyethylene glycol (PEG) oligomer or polymer can be covalently coupled to the polymer through a conjugating monomeric residue having a species which includes a functional group suitable for linking, directly or indirectly, to the polyethylene glycol oligomer or polymer. In another embodiment, the monomeric residue can be derived from a polymerizable monomer which includes a polyethylene glycol oligomer pendant to the monomer (e.g., PEGMA as described above).

In one general approach, PEG chains or blocks are covalently coupled to a membrane destabilizing polymer chain. For such embodiments, for example, PEG chains or blocks can have molecular weights ranging approximately from 1,000 to approximately 30,000. In some embodiments, the PEG is effective as (i.e., is incorporated into) a second block of a block copolymer. For example, PEG can be a second block coupled covalently to a block comprising a membrane destabilizing polymer. In some embodiments, PEG is conjugated to block copolymer ends groups, or to one or more pendant modifiable group present in polymeric compound, such as conjugated to modifiable groups within a hydrophilic segment or block (e.g., a second block) of a polymer (e.g., block copolymer). As an example, a block of a copolymer can be or can be conjugated to a shielding polymer having a repeat unit of Formula V

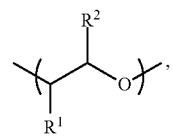

where $R^1$ and $R^2$ are each independently selected from the group consisting of hydrogen, halogen, and optionally substituted $C_1$-$C_3$ alkyl, and having a molecular weight ranging from about 1,000 to about 30,000 kD.

With reference to FIG. 1D, for example, heterogeneous polymeric micelles $M^{7C}$, $M^{8B}$, $M^{9B}$, and $M^{10C}$, can each comprises two or more compositionally distinct polymers, including a first polymer, $P^1$, and a second polymer, $P^2$, compositionally distinct from the first polymer $P^1$. The first polymer is a block copolymer comprising a hydrophilic block and a hydrophobic block. A polynucleotide is associated with the hydrophilic block of the first polymer (e.g., through ionic association ($M^{7C}$), covalent pendant coupling ($M^{10C}$), covalent end-coupling ($M^{8B}$, $M^{9B}$)). The second polymer is a block copolymer comprising a hydrophilic block and a hydrophobic block. The hydrophilic block of the second polymer can be a shielding polymer, such as a neutral, hydrophilic polymer. The hydrophobic block of the second polymer associates with the hydrophobic block of the first polymer to form a stable heterogeneous micelle (e.g., in an aqueous medium at pH 7.4).

In another general approach, a monomeric residue is derived from a polymerizable monomer comprising a PEG oligomer; for example, such monomeric residues can be incorporated into the polymer or into one or more blocks of a block copolymer during polymerization: In preferred embodiments, monomeric residues can be derived from a polymerizable monomer having a pendant group comprising an oligomer of formula I

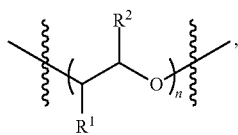

I where $R^1$ and $R^2$ are each independently selected from the group consisting of hydrogen, halogen, and optionally substituted $C_1$-$C_3$ alkyl, and n is an integer ranging from 2 to 20.

In preferred embodiments, a polymer chain can comprise a plurality of monomeric residues derived from a polymerizable monomer having a formula III

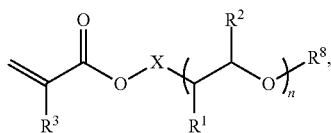

III where
X is independently selected from the group consisting of O, $NR^9$, and S,
$R^1$, $R^2$ and $R^3$ are each independently selected from the group consisting of hydrogen, halogen, and optionally substituted $C_1$-$C_3$ alkyl,
n is an integer ranging from 2 to 20,
$R^8$ is selected from the group consisting of hydrogen, halogen, optionally substituted $C_1$-$C_3$ alkyl, and a targeting moiety, optionally linked through a linking moiety, and
$R^9$ is selected from the group consisting of hydrogen, and optionally substituted $C_1$-$C_5$ alkyl.

In preferred embodiments, a polymer chain can comprise a plurality of monomeric residues derived from a polymerizable monomer having a formula IV

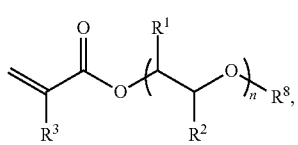

IV where
$R^1$, $R^2$ and $R^3$ are each independently selected from the group consisting of hydrogen, halogen, and optionally substituted $C_1$-$C_3$ alkyl,
n is an integer ranging from 2 to 20, and $R^8$ is selected from the group consisting of hydrogen, halogen, optionally substituted $C_1$-$C_3$ alkyl, and a targeting moiety, optionally linked through a linking moiety.

With further reference to FIG. 1D, for example, heterogeneous polymeric micelles $M^{7A}$, $M^{7B}$, $M^{8A}$, $M^{9A}$, $M^{10A}$, and $M^{10B}$, can each comprises two or more compositionally distinct polymers, including a first polymer, $P^1$, and a second polymer, $P^2$, compositionally distinct from the first polymer $P^1$. The first polymer is a block copolymer comprising a hydrophilic block and a hydrophobic block. A polynucleotide is associated with the hydrophilic block of the first polymer (e.g., through ionic association ($M^{7A}$, $M^{7B}$), covalent pendant coupling ($M^{10A}$, $M^{10B}$), covalent end-coupling ($M^{8A}$, $M^{9A}$)). The second polymer is a block copolymer comprising a hydrophilic block and a hydrophobic block. The hydrophilic block of the first polymer ($M^{7A}$, $M^{10A}$) and/or the hydrophilic block of the second polymer ($M^{7B}$, $M^{8A}$, $M^{9A}$, $M^{10B}$) can comprise monomeric residues derived from a polymerizable monomer having a pendant group comprising a shielding agent, such as shielding oligomer or polymer. The hydrophobic block of the second polymer associates with the hydrophobic block of the first polymer to form a stable heterogeneous micelle (e.g., in an aqueous medium at pH 7.4).

In such preferred embodiments, a polymer chain can comprise a plurality of shielding monomeric residues derived from a polymerizable monomer having a shielding species (e.g., of formula I, III, IV or otherwise), in a block or segment which is a random copolymer comprising at least about 10% by weight of monomeric residues having a pendant group comprising a shielding oligomer. Preferably, a random copolymer can comprise at least about 20% by weight of monomeric residues having a pendant group comprising a shielding oligomer. Preferably, a random copolymer can comprise at least about 30% by weight of monomeric residues having a pendant group comprising a shielding oligomer.

Targeting

Generally, one or more of the constituent polymers of the heterogeneous polymeric micelles—or blocks of such polymers can comprise a targeting moiety. Such targeting moiety can be a ligand having affinity for one or more receptors effective for mediating endocytosis. Generally, the targeting moiety is covalently coupled to a hydrophilic block of the first polymer or to a hydrophilic block of the second polymer.

Generally, in certain embodiments, constituent polymeric polymers of the micelles described herein comprise at least one targeting moiety (e.g., a moiety that targets a specific cell or type of cell). The targeting moiety can bind to and/or have a specific affinity for one or more biological receptors or other compounds or cell surfaces of interest. In some preferred embodiments, a targeting moiety can be a ligand having affinity for one or more receptors effective for mediating cell uptake, e.g., via endocytosis.

In certain instances, the efficiency of the cell uptake of the polymeric compounds is enhanced by incorporation of targeting moieties covalently bonded to the first and/or second constituent polymers of the heterogeneous micelle. In the context of cell uptake, a targeting moiety (targeting agent) is an agent which recognizes the surface of a cell, generally or selectively (e.g., a select cell). In some embodiments, targeting moieties recognize a cell surface antigen or bind to a receptor on the surface of the target cell. Suitable targeting moieties include, by way of non-limiting example, antibodies, antibody-like molecules, or peptides, such as an integrin-binding peptides such as RGD-containing peptides, or small molecules, such as vitamins, e.g., folate, sugars such as lactose and galactose, or other small molecules. Cell surface antigens include a cell surface molecule such as a protein, sugar, lipid or other antigen on the cell surface. In specific embodiments, the cell surface antigen undergoes internalization. Examples of cell surface antigens targeted by the targeting moieties of the polymeric compounds provided herein include, but are not limited, to the transferrin receptor type 1 and 2, the EGF receptor, HER2/Neu, VEGF receptors, integrins, NGF, CD2, CD3, CD4, CD8, CD19, CD20, CD22, CD33, CD43, CD38, CD56, CD69, and the asialoglycoprotein receptor.

As described more fully below, targeting moieties can be covalently attached, in various embodiments, to a polymeric compound (e.g., block copolymer compound), preferably for example through a side chain of a chain extension residue monomeric unit, or otherwise incorporated, preferably in each case where the chain extension moiety is provided at a terminal end of a polymeric compound or between two polymer chains of a polymeric compound. Attachment of the targeting moiety to the polymer chain can be achieved in any suitable manner, e.g., by any one of a number of conjugation chemistry approaches including but not limited to a linking moiety as described below.

In alternative embodiments, targeting ligands are attached to a monomer residue of the polymer chain, and the resulting compound is then used in the polymerization synthesis of a polymer (e.g., block copolymer) as described herein. In some embodiments, targeting moieties are covalently bonded to a block of a first block copolymer, or to a block of a second block copolymer. In some embodiments, the targeting moieties are attached to the sense or antisense strand of siRNA covalently bound to non-covalently associated with a polymeric compound. In certain embodiments, the targeting agent is attached to a 5' or a 3' end of the sense or the antisense strand.

Preferably, the targeting moiety is covalently coupled, through a linking moiety, to hydrophilic blocks of the constituent polymers of the heterogeneous polymeric micelle. In a preferred approach, a hydrophilic block of the first polymer and/or second polymer can comprise monomeric residues having a conjugatable moiety (e.g., functional group). The targeting moiety can be covalently coupled to the hydrophilic block of the first or second polymers of the heterogeneous polymeric micelles through such conjugatable moiety, optionally through a linking moiety.

With further reference to FIG. 1E, for example, heterogeneous polymeric micelles $M^{7D}$, $M^{7E}$, $M^{8C}$, $M^{9C}$, $M^{10D}$, and $M^{10E}$, can each comprises two or more compositionally distinct polymers, including a first polymer, $P^1$, and a second polymer, $P^2$, compositionally distinct from the first polymer $P^1$. The first polymer is a block copolymer comprising a hydrophilic block and a hydrophobic block. A polynucleotide is associated with the hydrophilic block of the first polymer (e.g., through ionic association ($M^{7D}$, $M^{7E}$), covalent pendant coupling ($M^{10D}$, $M^{10E}$) covalent end-coupling ($M^{8C}$, $M^{9C}$)). The second polymer is a block copolymer comprising a hydrophilic block and a hydrophobic block. The hydrophilic block of the first polymer ($M^{7D}$, $M^{10D}$) and/or the hydrophilic block of the second polymer ($M^{7E}$, $M^{8C}$, $M^{9C}$, $M^{10E}$) can comprise monomeric residues having a conjugatable moiety (e.g., functional group) to which the targeting moiety ("T") can be covalently coupled to the hydrophilic block. The hydrophobic block of the second polymer associates with the hydrophobic block of the first polymer to form a stable heterogeneous micelle (e.g., in an aqueous medium at pH 7.4).

With reference to FIG. 1E, for example, heterogeneous polymeric micelles $M^{7F}$, $M^{8D}$, $M^{9D}$, and $M^{10F}$, can each comprises two or more compositionally distinct polymers, including a first polymer, $P^1$, and a second polymer, $P^2$, compositionally distinct from the first polymer $P^1$. The first polymer is a block copolymer comprising a hydrophilic block and a hydrophobic block. A polynucleotide is associated with the hydrophilic block of the first polymer (e.g., through ionic association ($M^{7F}$), covalent pendant coupling ($M^{10F}$), covalent end-coupling ($M^{8D}$, $M^{9D}$)). The second polymer is a block copolymer comprising a hydrophilic block and a hydrophobic block. The hydrophilic block of the second polymer can be a targeting moiety, or can be covalently end-coupled to the targeting moiety. The hydrophobic block of the second polymer associates with the hydrophobic block of the first polymer to form a stable heterogeneous micelle (e.g., in an aqueous medium at pH 7.4).

Linking Moiety

Generally, the biomolecular agent can be linked to the chain extension moiety through one or more linking moieties.

The linking moiety can be a covalent bond.

The linking moiety can be a multifunctional (e.g., di-functional) moiety, such as a hydrocarbyl, substituted hydrocarbyl, hetero-hydrocarbyl or substituted heterohydrocarbyl, in each case comprising two or more reactive functional groups. For example, the linking moiety can be a disulfide linking moiety L. For example, the linking moiety can be an acid-labile linking moiety L. In some preferred embodiments, the linking moiety L can comprise at least one bond which is acid labile at an endosomal pH.

In some embodiments, a biomolecular agent (e.g., an oligonucleotide) is conjugated to an extension moiety of the polymeric compound by a suitable chemical conjugation approach. In some embodiments, the covalent bond between an extension moiety and a biomolecular agent can be optionally, non-cleavable, or cleavable. In certain embodiments, a precursor of one or more RNAi agent (e.g. a dicer substrate) is attached to the polymeric compound by a non-cleavable bond. In some embodiments, one or more RNAi agent is attached through a cleavable bond. In certain embodiments, the cleavable bonds utilized in such approach include, by way of non-limiting example, disulfide bonds (e.g., disulfide bonds that dissociate in the reducing environment of the cytoplasm).

Linking moieties can include, for example, amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In specific embodiments, "click" chemistry is used to attach the bioconjugate such as a targeting ligand to the polymeric compounds (e.g., a block copolymer) as provided herein (for example of "click" reactions, see Wu, P.; Fokin, V. V. Catalytic Azide-Alkyne Cycloaddition: Reactivity and Applications. Aldrichim. Acta 2007, 40, 7-17). A large variety of conjugation chemistries are optionally utilized (see, for example, Bioconjugation, Aslam and Dent, Eds, Macmillan, 1998 and chapters therein). In some embodiments, conjugation is also performed with pH-sensitive bonds and linkers, including, but not limited to, hydrazone and acetal linkages. Any other suitable conjugation method is optionally utilized as well, for example a large variety of conjugation chemistries are available (see, for example, Bioconjugation, Aslam and Dent, Eds, Macmillan, 1998 and chapters therein).

Preparation of Micelles and Polynucleotide-Containing Compositions

Generally, a heterogeneous polymeric micelle can be prepared by providing the first polymer and the second compositionally distinct polymer in a first denaturing medium to form a heterogeneous mixture of the first polymer and the second polymer and then transposing (e.g., diluting, dialyzing) the heterogeneous mixture to a second aqueous medium. The hydrophobic block of the first polymer is allowed to associate with the hydrophobic block of the second polymer in the aqueous medium to form the heterogeneous micelle.

Generally, a composition comprising a heterogeneous polymeric micelle and a polynucleotide associated with the micelle, can be prepared by providing the first polymer and the second compositionally distinct polymer in a first denaturing medium to form a heterogeneous mixture of the first polymer and the second polymer and then transposing (e.g., diluting, dialyzing) the heterogeneous mixture to a second aqueous medium. The hydrophobic block of the first polymer is allowed to associate with the hydrophobic block of the second polymer in the aqueous medium to form the heterogeneous micelle. A polynucleotide can be associated with such heterogeneous polymeric micelle, or alternatively, with at least one of the first or second block copolymers, either before or after heterogeneous micelle formation.

The first denaturing medium preferably comprises an alcohol, such as a $C_1$-$C_4$ alcohol. The first denaturing medium can comprise the alcohol, such as a $C_1$-$C_4$ alcohol, for example as a co-solvent (e.g., with $H_2O$) at a concentration of at least about 30%, preferably at least about 40%, preferably at least about 50%, and in some embodiments at higher percentages, such as at least about 70% or at 100% (i.e., neat alcohol, such as a neat $C_1$-$C_4$ alcohol).

The second aqueous medium can be a pH-buffered aqueous medium. Preferably, the second aqueous medium can be a phosphate buffered aqueous medium, for example, such as phosphate-buffered saline (PBS).

Generally for embodiments where the polynucleotide-containing composition comprise polynucleotide ionically associated with the cationic hydrophilic block at least one of the polymers (e.g., a first polymer), a number of suitable approaches can be effected for preparing a composition comprising the heterogeneous polymeric micelles and an associated polynucleotide. In each of such approach, at least one of the polymers (e.g., a first polymer) comprises a hydrophilic block comprising a plurality of cationic monomeric residues.

In one such approach, the first and second polymers are allowed to associate first (e.g., under more stringent denaturing conditions), followed by addition of polynucleotide (e.g., under less stringent denaturing conditions). More specifically, a heterogeneous mixture of the first polymer and the second polymer are formed in the first denaturing medium. The first denaturing medium is partially diluting with a pH-buffered aqueous medium, and the polynucleotide is provided to the partially diluted first medium, and allowed to associate with the cationic monomeric residues of the hydrophilic block in the partially diluted first medium. The partially diluted first medium can then be further diluted (e.g., via dialysis) with a pH buffered aqueous medium.

In an alternative approach, the polynucleotide and at least one of the polymers are allowed to associated first (e.g., under moderate stringency denaturing conditions), followed by addition of the other polymer(s) (e.g., under the same moderate conditions). Specifically, the first polymer and the polynucleotide are provided to the first medium. Preferably, the first medium comprises at least 30% and not more than about 70% alcohol, such as a $C_1$-$C_4$ alcohol. The polynucleotide is allowed to associate with the cationic monomeric residues of the hydrophilic block of the first polymer in the first medium. The second polymer can then be provided to the first medium to form the heterogeneous mixture comprising the first polymer, the associated polynucleotide, and the second polymer in the first medium. The first medium can then be diluted with an aqueous medium, such as a pH-buffered aqueous medium.

In a further approach, the polynucleotide can be associated with a cationic hydrophilic block of at least one of first and/or second block copolymers after formation of the heterogeneous polymeric micelle. For example, a heterogeneous polymeric micelle can be formed, for example, substantially as described above. A polynucleotide is subsequently associated therewith by mixing the polynucleotide with the polymeric micelle an aqueous medium, such as a pH-buffered aqueous medium, and optionally followed by dilution or dialysis (e.g., against PBS pH 7.4).

Generally, various approaches also exist for preparing polynucleotide-containing compositions for embodiments in which a polynucleotide is covalently associated with the heterogeneous polymeric micelle by covalent conjugation to the first and/or second block copolymers. In each of such approaches, a composition comprising a mixed polymeric micelle and a polynucleotide associated therewith can be formed from two compositionally distinct block copolymers—where at least one of the first polymer or the second polymer have a hydrophilic block which comprises a conjugatable monomeric residue (e.g., comprising MAA(NHS) monomeric residue).

In one approach, for example, the polynucleotide-containing composition can be prepared by forming the heterogeneous polymeric micelle first substantially as described above, and subsequently effecting conjugation of the polynucleotide to the heterogeneous polymeric micelle.

In an alternative approach, the polynucleotide-containing composition can be prepared by first forming a polynucleotide-conjugated block copolymer, and subsequently effecting formation of the heterogeneous polymeric micelle substantially as described above.

Significantly, supramolecular properties of the heterogeneous polymeric micelles or compositions containing such mixed micelles can be controlled during preparation thereof.

Generally, for example, the relative ratio of a first polymer to a second polymer can be controllably varied to achieve, in combination with variation in the composition of such polymers, a desired set of chemical or physical properties of the micelle. As a non-limiting example, a heterogeneous (mixed) polymeric micelle can be formed from two or more block copolymers—having compositionally distinct hydrophilic blocks and each having substantially the same hydrophobic block—e.g., as a membrane destabilizing block. Specifically, for example, a first block copolymer can have a hydrophilic block consisting essentially of a cationic hydrophilic monomeric residue (e.g., DMAEMA), and a second block copolymer can have a hydrophilic block consisting essentially of a neutral hydrophilic monomeric residue (e.g., PEGMA). Such first and second polymers can be combined at various desired molar ratios (e.g., 2:1, 1:1, 1:2) to form a heterogeneous micelle having a hydrophilic shell with corresponding relative cationic charge. In this example, charge is being modulated by varying the relative amount of cationic shell blocks versus neutral shell blocks of the micelle.

Hence, as described in further detail above, heterogeneous polymeric micelles can be achieved having (i) controllably varied (tunable) block copolymer composition (e.g., as compared between hydrophilic blocks) (ii) controllably varied (tunable) relative ratios of hydrophilic block and hydrophilic blocks (e.g., resulting in varied relative hydrophilic chain lengths as compared between hydrophilic blocks), (iii) controllably varied (tunable) total molecular weights of polymers (e.g., resulting in varied relative total chain lengths as compared between polymers), and (iv) controllably varied (tunable) relative ratios of the number of polymer molecules of the first block copolymer to the second block copolymer (or additional block copolymers).

Micelle Properties

Various aspects of the invention—including heterogeneous polymeric micelles, constituent polymers thereof, and compositions comprising such heterogeneous polymeric micelles and an agent such as a polynucleotide associated therewith—can have and/or be characterized by certain properties which can be controllably varied (i.e. tuned) for a specific application of interest.

Micellic properties, constituent polymer properties, and compositional properties are generally interrelated—in that one such property may influence another such property; and in each case, any such property can directly or indirectly influence other properties—including without limitation such as formulation properties, pharmacokinetic properties, biodistribution properties, and/or biological properties, among others.

The following properties and key parameters are exemplary, and are generally preferred for heterogeneous polymeric micelles used in compositions comprising a polynucleotide associated with the heterogeneous polymeric micelle. Such properties are recited as examples, and should not be considered as limiting on the invention, except to the extent specifically recited in a particular one or more claims.

The heterogeneous polymeric micelles of the invention can have and/or be characterized by various micellic properties. Such properties can include for example, critical micelle concentration, aggregation number, particle size, and solubility, among others.

Generally, a heterogeneous polymeric micelle can preferably have a critical micelle concentration, CMC, ranging from about 0.2 ug/ml to about 20 ug/ml, and preferably ranging from about 0.5 ug/ml to about 10 ug/ml. In some embodiments, the critical micelle concentration can range from about 1 ug/ml to about 5 ug/ml.

Generally, a heterogeneous polymeric micelle can preferably have an aggregation number ranging from about 10 to about 100 total chains per micelle, and preferably from about 20 to about 60 chains per micelle. In some embodiments, the aggregation number can range from about 30 to 50 chains per micelle.

Generally, a heterogeneous polymeric micelle can have a particle size ranging from about 5 nm to about 500 nm, and preferably from about 10 nm to about 200 nm. In some embodiments, the particle size can range from about 20 nm to about 100 nm.

Generally, the molecular weight of a heterogeneous polymeric micelle (considered as the assembled micelle) can be a number-average molecular weight, Mn, ranging from about $0.5 \times 10^6$ to about $3.6 \times 10^6$ Daltons, and preferably from about $0.75 \times 10^6$ to about $2.0 \times 10^6$ Daltons. In some embodiments, the total a number-average molecular weight, Mn, can range from about $1.0 \times 10^6$ to about $1.5 \times 10^6$.

Generally, a heterogeneous polymeric micelle can be soluble in an aqueous medium, such as a physiologically relevant medium. Generally, a heterogeneous polymeric micelle can have a solubility ranging from about 1 mg/ml to about 200 mg/ml, preferably from about 5 mg/ml to about 150 mg/ml. In some embodiments, a heterogeneous polymeric micelle can have a solubility ranging from about 10 mg/ml to about 100 mg/ml, or from about 20 mg/ml to about 50 mg/ml.

Constituent polymers, including constituent block copolymers can have and/or be characterized by various properties which can influence one or more micellic properties. For example, such properties can include the total number-average molecular weight for the constituent polymer, the relative number-average molecular weight, Mn, of the hydrophilic block to a hydrophobic block for a constituent polymer, a relative degree of hydrophobicity, a polydispersity index of the constituent polymer (considered as a whole) or each block thereof, among others.

The total number-average molecular weight for the constituent polymer (considered as a whole, and alternatively characterized by the sum of block molecular weights within a constituent block copolymer) can generally be a number-average molecular weight, Mn, ranging from about 5,000 to about 100,000 Daltons, and preferably from about 10,000 to about 90,000 Daltons. In some embodiments, the total a number-average molecular weight, Mn, can range from about 15,000 to about 80,000 Daltons or from about 15,000 Daltons to about 75,000 Daltons. In preferred embodiments (e.g., for polynucleotide-containing compositions), and without limitation, constituent block copolymers of the heterogeneous polymeric micelle can comprises a hydrophilic block having a number-average molecular weight, Mn, ranging from about 5,000 to about 20,000 Daltons, and a hydrophobic block having a number-average molecular weight, Mn, ranging from about 10,000 to about 60,000 Daltons.

The relative ratio of number-average molecular weight, Mn, of the hydrophilic block to a hydrophobic block of a constituent block copolymer can generally range from about 2:1 to about 1:9, preferably from about 3:2 to about 1:7, preferably from about 3:2 to about 1:5, preferably from about 3:2 to about 1:4, preferably from about 1:1 to about 1:5, preferably from about 1:1 to about 1:4, preferably from about 1:1 to about 1:3 and in some embodiments from about 1:1 to about 1:2. Other preferred ranges are as discussed above in connection with heterogeneous polymeric micellic general structure.

A constituent block copolymer or a hydrophobic block thereof can have a characterized relative degree of hydrophobicity. A hydrophobicity can be represented for example by, a $\pi$ value of the hydrophobic block or by other suitable measure, as discussed above.

Each of the constituent first polymer and second polymer, or each block thereof, can have a polydispersity index ranging from 1.0 to about 2.0, preferably from 1.0 to about 1.7, preferably from 1.0 to about 1.4, and in some embodiments from 1.0 to about 1.2, or from 1.0 to about 1.1, or from 1.0 to 1.05.

Considered in combination, for example, a heterogeneous polymeric micelle and/or a constituent polymer thereof (or a block thereof) can preferably comprise one or more properties selected from the group consisting of: (i) an aggregation number ranging from about 20 to about 60 chains per micelle; (ii) a critical micelle concentration, CMC, ranging from about 0.5 ug/ml to about 10 ug/ml, and (iii) a ratio of a number-average molecular weight, Mn, of the hydrophilic block to the hydrophobic block, ranging from about 1:1.5 to about 1:6.

Preferably, considered in combination, for example, a heterogeneous polymeric micelle and/or a constituent polymer thereof (or a block thereof) can comprise one or more properties selected from the group consisting of: (i) an aggregation number ranging from about 30 to about 50 chains per micelle; (ii) a critical micelle concentration, CMC, ranging from about 1 ug/ml to about 5 ug/ml; and (iii) a ratio of a number-average molecular weight, Mn, of the hydrophilic block to the hydrophobic block, ranging from about 1:2 to about 1:4.

Compositions comprising such heterogeneous polymeric micelles and an agent such as a polynucleotide associated therewith, can have and/or be characterized by certain properties which can be controllably varied (i.e. tuned) for a specific application of interest.

For example, the number of polynucleotides associated with each micelle can range from about 1 to about 10,000, and preferably from about 4 to about 5,000, or from about 15 to about 3,000. In some embodiments, about 30 to about 2,500 polynucleotides can be associated with each micelle.

Biomolecular Agents

Compositions of the invention can comprise a heterogeneous polymeric micelle and an agent associated therewith. The agent can be a biomolecular agent. The agent can be a research reagent, a diagnostic agent, or a therapeutic agent, or a combination thereof.

Generally, a biomolecular agent (e.g., suitable for a therapeutic agent, diagnostic agent, research reagent) can be a polynucleic acid (e.g., a polynucleotide), a polyamine acid (e.g., a peptide or protein), a carbohydrate (e.g., a polysaccharide), or a small organic molecule (e.g., molecular weight less than about 1000 g/mol or less than about 500 g/mol), such as a small molecule pharmaceutical.

Generally, in some embodiments, agents such as therapeutic agents are associated with a hydrophilic block of a constituent polymer of the micelle (e.g., such that the therapeutic agent is present substantially in the shell of the heterogeneous polymeric micelle). In other embodiments, the agent can be associated with other blocks of a constituent block copolymer—e.g., such as a hydrophobic block of the heterogeneous polymeric micelle (e.g., such that the agent is present in the core of the heterogeneous polymeric micelle). In other embodiments, the agent can be associated with an end-region of a constituent polymer of the heterogeneous polymeric micelle—e.g., covalent end-conjugated to a hydrophilic block of a constituent polymer (e.g., such that some portion of the agent may be substantially on or near the surface of the heterogeneous polymeric micelle).

Generally, the amount of an agent associated with the heterogeneous polymeric micelle is not narrowly critical and can be determined for a specific application of interest. Generally, a composition comprising a heterogeneous polymeric micelle and an agent associated therewith can comprise various ranges, depending on the agent, the mode of association (e.g., covalent or non-covalent), and the application of interest. Typical general ranges can include for example from 1-5, 5-250, 5-1000, or 250-1000 agents per micelle. Generally, therefore, the number of agents per micelle can be at least 2, at least 5, at least 10, at least 20, or at least 50 agents, such as polynucleotides, per micelle. In a composition comprising heterogeneous polymeric micelles and an agent, the amount of the agent per micelle can be determined on an average basis, measured over a sample population of agent-containing micelles.

In specific embodiments, the agent is a polynucleotide, an oligonucleotide, a gene expression modulator, a knockdown agent, an siRNA, an RNAi agent, a dicer substrate, an miRNA, an shRNA, an antisense oligonucleotide, or an aptamer. In other specific embodiments, the therapeutic agent is an aiRNA (Asymmetric RNA duplexes mediate RNA interference in mammalian cells. Xiangao Sun, Harry A Rogoff, Chiang J Li *Nature Biotechnology* 26, 1379-1382 (2008)).

In some embodiments, the compositions described herein comprise a heterogeneous polymeric micelle and an associated polynucleotide, wherein the polynucleotide has functionality promoting, demoting or otherwise modulating expression in a cell, such as eukaryotic cell (e.g., mammalian cell). The polynucleotide can be a mammalian expression vector. The polynucleotide can have activity to correct an endogenous gene sequence in a cell, such as a mammalian cell, such as a human cell. The polynucleotide can be a gene expression modulator.

In some embodiments, compositions comprising heterogeneous polymeric micelles and a polynucleotide are used for gene therapy. The treatment of diseases and disorders by gene therapy generally involves the transfer of new genetic information into cells. "Gene therapy vectors" comprise the new genetic material to be delivered, which is, optionally, in a mammalian expression vector. The uses of heterogeneous polymeric micelles include delivery of polynucleotide (e.g., DNA) sequences for gene replacement, inhibition of gene expression, gene correction or gene augmentation, or the introduction of genes to have some other desired effect, such as the modulation of immune responses. Inhibition of gene expression is accomplished in any suitable manner, including, by way of non-limiting example, by expression of gene cassettes in cells which express shRNAs or other RNAi agents.

In certain embodiments, the polynucleotide is an oligonucleotide gene expression modulator. In further embodiments, the polynucleotide is an oligonucleotide knockdown agent. In specific embodiments, the polynucleotide is an RNAi agent, dicer substrate, or siRNA.

In some aspects, the heterogeneous polymeric micelles provided herein comprise two or more types of oligonucleotide agents wherein the oligonucleotide agents silence different genes of the same disease or different diseases.

In certain embodiments, the therapeutic agent is a protein, peptide, dominant-negative protein, enzyme, antibody, or antibody fragment.

In some embodiments, the therapeutic agent is a proteinaceous agent. Conjugation of proteinatious therapeutic agents (e.g., a polypeptide) to the heterogeneous polymeric micelles provided herein is achieved according to a variety of conjugation processes by a chemical reaction involving one or more of the functional groups of the proteinaceous therapeutic agent (e.g., a polypeptide) with one or more of the functional groups present in the heterogeneous polymeric micelle (e.g., in the shell of the heterogeneous polymeric micelle or on a monomeric unit of the shell block). Polypeptide functional groups that are usually involved include but are not limited to amino, hydroxy, thiol, or carboxyl groups. Such groups can be present as a terminal group or present on the amino acid side chains. In some embodiments, the proteinaceous therapeutic agents are engineered to contain non-natural amino acids comprising special functional groups for formation of site-specific conjugates, e.g., azido groups for conjugation via "click" chemistry.

In some embodiments, the therapeutic agent is a carbohydrate, or a polysaccharide.

In some embodiments, the agent can be a small organic molecule—an organic molecule having a molecular weight less than about 10,000 g/mol or less than about 5,000 g/mol, and in some instances less than about 2,000 g/mol or less than about 1,000 g/mol. Such small organic molecule can be a pharmaceutical agent (e.g., a substance which is an active pharmaceutical ingredient (API)). In some instances, the present inventions are particularly advantaged for intracellular delivery of small organic molecules which by virtue of their size (e.g., a molecular weight of >500 g/mol), charge, or other physicochemical properties, are unable or poorly able to enter cells on their own.

In some embodiments, the small molecule pharmaceutical can be a hydrophobic pharmaceutical. The inventions include a composition comprising a heterogeneous polymeric micelle and a hydrophobic pharmaceutical agent (e.g., small molecule hydrophobic drug) associated therewith. The hydrophobic pharmaceutical agent can be associated for example, with the hydrophobic block of one or more of the constituent polymers of the heterogeneous polymeric micelle (e.g., and for example be substantially in the core of the heterogeneous polymeric micelle).

In any of the aforementioned embodiments, the agent, including polynucleotide agent, a polyamino acid agent, polysaccharide agent or a small organic molecule agent can be a therapeutic agent, for prophyaxis or treatment of a condition in a mammalian subject such as a human subject, preferably in need thereof.

In some embodiments, the composition comprises a heterogeneous polymeric micelle provided herein and a diagnostic agent associated therewith. In some embodiments, the diagnostic agent is a diagnostic imaging agent, e.g., an agent useful in imaging the mammalian vascular system which includes but is not limited to position emission tomography (PET) agents, computerized tomography (CT) agents, magnetic resonance imaging (MRI) agents, nuclear magnetic imaging agents (NMI), fluoroscopy agents and ultrasound contrast agents. Such diagnostic agents include radioisotopes of such elements as iodine (I), including $^{123}$I, $^{125}$I, $^{131}$I, etc., barium (Ba), gadolinium (Gd), technetium (Tc), including $^{99}$Tc, phosphorus (P), including $^{31}$P, iron (Fe), manganese (Mn), thallium (TI), chromium (Cr), including $^{51}$Cr, carbon (C), including $^{14}$C, or the like, fluorescently labeled compounds, or their complexes, chelates, adducts and conjugates. In other embodiments, the diagnostic agent is a marker gene that encode proteins that are readily detectable when expressed in a cell (including, but not limited to, β-galactosidase, green fluorescent protein, luciferase, and the like) and labeled nucleic acid probes (e.g., radiolabeled or fluorescently labeled probes). In some embodiments, covalent conjugation of diagnostics agents to one or more constituent polymers of a heterogeneous polymeric micelle is achieved according to a variety of conjugation processes. In other embodiments, the diagnostic agent is non-covalently associated with the heterogeneous polymeric micelle provided herein by complexing with a chelating residue (e.g., a carboxylic acid residue) incorporated into the block copolymers forming the heterogeneous polymeric micelle. In some embodiments, a radiolabeled monomer (e.g., a $^{14}$C-labeled monomer) is incorporated into the polymeric backbone of the heterogeneous polymeric micelle (e.g., the shell block or the core block of the micelle). In some embodiments, a heterogeneous polymeric micelle associated with a diagnostic agent comprises a targeting moiety. In some embodiments, a heterogeneous polymeric micelle associated with a diagnostic agent comprises a shielding moiety.

In some embodiments, the composition comprises a heterogeneous polymeric micelle provided herein and a research agent associated therewith.

Pharmaceutical Compositions

The compositions comprising a heterogeneous polymeric micelle and an agent, such as a biomolecular agent (e.g., a polynucleotide) can be a pharmaceutical composition. Such pharmaceutical composition can comprise, for example, a heterogeneous polymeric micelle, a biomolecular agent, such as a polynucleotide, and a pharmaceutically acceptable excipient.

Therapeutic Uses

Compositions comprising heterogeneous polymeric micelles and an agent such as a polynucleotide can be used in various methods.

Generally, such compositions can be used for example in a method for intracellular delivery of an agent such as a polynucleotide. The composition comprising a heterogeneous polymeric micelle and an agent (e.g., a polynucleotide) associated therewith can be exposed to and contacted with a with a cell surface (e.g., via directed targeting) in a medium at a first pH. The composition is introduced into an endosomal membrane within the cell, for example through endocytosis, and in some embodiments through receptor-mediated endocytosis. The endosomal membrane is destabilized (e.g., by a constituent polymer or block thereof which is a membrane destabilizing polymer), thereby delivering the composition or the agent (e.g., polynucleotide) to the cytosol of the cell. The medium can be an in vitro medium. The medium can be an in-vitro medium such as a physiological medium.

Generally, for example, such compositions can be used for modulating the activity of an intracellular target in a cell. The agent such as a polynucleotide can be delivered to the cytosol of a cell according to the method described in the immediately-preceding paragraph. The agent (e.g., polynucleotide) is allowed to interact with the intracellular target, thereby modulating the activity of the intracellular target.

More specifically for example, in some embodiments, the compositions comprising heterogeneous polymeric micelles (e.g., micelles) provided herein are useful in treating a subject at risk for or afflicted with disorders associated with and/or caused by high plasma levels or cholesterol, apolipoprotein b, and/or LDL cholesterol, e.g. hypercholesterolemia. In certain embodiments, the treatment comprises providing a heterogeneous polymeric micelle and a therapeutic agent (e.g., an oligonucleotide agent) associated therewith, wherein the therapeutic agent silences (e.g., by cleavage) a gene or a gene product which promotes such condition. In some embodiments the therapeutic agent (e.g., an oligonucleotide or RNAi agent) silences proprotein convertase subtilisin/kexin type 9 (PCSK9) gene responsible for regulation of low density lipoprotein (LDLR) levels and function, and thus heterogeneous polymeric micelles comprising such therapeutic agent are used to treat a subject having or at risk for a disorder characterized by unwanted PCSK9 expression, e.g., disorders associated with and/or caused by high plasma levels or cholesterol, apolipoprotein b, and/or LDL cholesterol, e.g. hypercholesterolemia. In some embodiments, the heterogeneous polymeric micelles deliver PCSK9-silencing polynucleotide agent (e.g., siRNA) to a cell expressing PCSK9. In some embodiments, the cell is a liver cell.

In some embodiments, the heterogeneous polymeric micelles (e.g., micelles) provided herein are useful in treating a subject at risk for or afflicted with unwanted cell proliferation (e.g., malignant or nonmalignant cell proliferation). The treatment comprises providing a composition comprising a heterogeneous polymeric micelle and a therapeutic agent (e.g., an oligonucleotide agent), wherein the therapeutic agent can silence (e.g., by cleavage) a gene or a gene product which promotes unwanted cell proliferation; and administering a therapeutically effective dose of the heterogeneous polymeric micelle to a subject (e.g., a human subject.) In some embodiments, the therapeutic agent is a polynucleotide (e.g., an oligonucleotide) which is homologous to and can silence (e.g., by cleavage) a gene.

In certain embodiments, the gene is but is not limited to a growth factor or growth factor receptor gene, a phosphatase, a kinase, e.g., a protein tyrosine, serine or threonine kinase gene, an adaptor protein gene, a gene encoding a G protein superfamily molecule, or a gene encoding a transcription factor. In some instances, the composition comprises a heterogeneous polymeric micelle and a polynucleotide which silences a gene which is expressed in a specific tissue or organ, including, but not limited to lung, pancreas, liver, kidney, ovary, muscle, skin, breast, colon, stomach, and the like.

In some embodiments, the oligonucleotide agent silences one or more of the following genes: the PDGF beta gene, and thus can be used to treat a subject having or at risk for a disorder characterized by unwanted PDGF beta expression, e.g., testicular and lung cancers; an Erb-B gene (e.g., Erb-B-2 or Erb-B-3), and thus can be used to treat a subject having or at risk for a disorder characterized by unwanted Erb-B expression, e.g., breast or lung cancer; the Src gene, and thus can be used to treat a subject having or at risk for a disorder characterized by unwanted Src expression, e.g., colon cancers; the CRK gene, and thus can be used to treat a subject having or at risk for a disorder characterized by unwanted CRK expression, e.g., colon and lung cancers; the GRB2 gene, and thus can be used to treat a subject having or at risk for a disorder characterized by unwanted GRB2 expression, e.g., squamous cell carcinoma; the RAS gene, and thus can be used to treat a subject having or at risk for a disorder characterized by unwanted RAS expression, e.g., pancreatic, colon and lung cancers, and chronic leukemia; the MEKK gene, and thus can be used to treat a subject having or at risk for a disorder characterized by unwanted MEKK expression, e.g., squamous cell carcinoma, melanoma or leukemia; the JNK gene, and thus can be used to treat a subject having or at risk for a disorder characterized by unwanted JNK expression, e.g., pancreatic or breast cancers; the RAF gene, and thus can be used to treat a subject having or at risk for a disorder characterized by unwanted RAF expression, e.g., lung cancer or leukemia; the Erk1/2 gene, and thus can be used to treat a subject having or at risk for a disorder characterized by unwanted Erk1/2 expression, e.g., lung cancer; the PCNA (p21) gene, and thus can be used to treat a subject having or at risk for a disorder characterized by unwanted PCNA expression, e.g., lung cancer; the MYB gene, and thus can be used to treat a subject having or at risk for a disorder characterized by unwanted MYB expression, e.g., colon cancer or chronic myelogenous leukemia; the c-MYC gene, and thus can be used to treat a subject having or at risk for a disorder characterized by unwanted c-MYC expression, e.g., Burkitt's lymphoma or neuroblastoma; the JUN gene, and thus can be used to treat a subject having or at risk for a disorder characterized by unwanted JUN expression, e.g., ovarian, prostate or breast cancers; the FOS gene, and thus can be used to treat a subject having or at risk for a disorder characterized by unwanted FOS expression, e.g., skin or prostate cancers; the BCL-2 gene, and thus can be used to treat a subject having or at risk for a disorder characterized by unwanted BCL-2 expression, e.g., lung or prostate cancers or Non-Hodgkin lymphoma; the Cyclin D gene, and thus can be used to treat a subject having or at risk for a disorder characterized by unwanted Cyclin D expression, e.g., esophageal and colon cancers; the VEGF gene, and thus can be used to treat a subject having or at risk for a disorder characterized by unwanted VEGF expression, e.g., esophageal and colon cancers; the EGFR gene, and thus can be used to treat a subject having or at risk for a disorder characterized by unwanted EGFR expression, e.g., breast cancer; the Cyclin A gene, and thus can be used to treat a subject having or at risk for a disorder characterized by unwanted Cyclin A expression, e.g., lung and cervical cancers; the Cyclin E gene, and thus can be used to treat a subject having or at risk for a disorder characterized by unwanted Cyclin E expression, e.g., lung and breast cancers; the WNT-1 gene, and thus can be used to treat a subject having or at risk for a disorder characterized by unwanted WNT-1 expression, e.g., basal cell carcinoma; the beta-catenin gene, and thus can be used to treat a subject having or at risk for a disorder characterized by unwanted beta-catenin expression, e.g., adenocarcinoma or hepatocellular carcinoma; the c-MET gene, and thus can be used to treat a subject having or at risk for a disorder characterized by unwanted c-MET expression, e.g., hepatocellular carcinoma; the PKC gene, and thus can be used to treat a subject having or at risk for a disorder characterized by unwanted PKC expression, e.g., breast cancer; the NFKB gene, and thus can be used to treat a subject having or at risk for a disorder characterized by unwanted NFKB expression, e.g., breast, cancer; the STAT3 gene, and thus can be used to treat a subject having or at risk for a disorder characterized by unwanted STAT3 expression, e.g., prostate cancer; the survivin gene, and thus can be used to treat a subject having or at risk for a disorder characterized by unwanted survivin expression, e.g., cervical or pancreatic cancers; the Her2/Neu gene, and thus can be used to treat a subject having or at risk for a disorder characterized by unwanted Her2/Neu expression, e.g., breast cancer; the topoisomerase I gene, and thus can be used to treat a subject having or at risk for a disorder characterized by unwanted topoisomerase I expression, e.g., ovarian and colon cancers; the topoisomerase II alpha gene, and thus can be used to treat a subject having or at risk for a disorder characterized by unwanted topoisomerase II expression, e.g., breast and colon cancers.

In other embodiments the oligonucleotide agent silences mutations in one of the following genes: the p73 gene, and thus can be used to treat a subject having or at risk for a disorder characterized by unwanted p73 expression, e.g., colorectal adenocarcinoma; the p21(WAF1/CIP1) gene, and thus can be used to treat a subject having or at risk for a disorder characterized by unwanted p21(WAF1/CIP1) expression, e.g., liver cancer; the p27(KIP1) gene, and thus can be used to treat a subject having or at risk for a disorder characterized by unwanted p27(KIP1) expression, e.g., liver cancer; the PPM1D gene, and thus can be used to treat a subject having or at risk for a disorder characterized by unwanted PPM1D expression, e.g., breast cancer; the RAS gene, and thus can be used to treat a subject having or at risk for a disorder characterized by unwanted RAS expression, e.g., breast cancer; the caveolin I gene, and thus can be used to treat a subject having or at risk for a disorder characterized by unwanted caveolin I expression, e.g., esophageal squamous cell carcinoma; the MIB I gene, and thus can be used to treat a subject having or at risk for a disorder characterized by unwanted MIB I expression, e.g., male breast carcinoma (MBC); MTAI gene, and thus can be used to treat a subject having or at risk for a disorder characterized by unwanted MTAI expression, e.g., ovarian carcinoma; the M68 gene, and thus can be used to treat a subject having or at risk for a disorder characterized by unwanted M68 expression, e.g., human adenocarcinomas of the esophagus, stomach, colon, and rectum.

In some embodiments the oligonucleotide agent silences mutations in tumor suppressor genes, and thus can be used as a method to promote apoptotic activity in combination with chemotherapeutics. In some embodiments the in the tumor suppressor gene is selected from one or more of the following tumor suppressor genes: the p53 tumor suppressor gene, the p53 family member DN-p63, the pRb tumor suppressor gene, the APC1 tumor suppressor gene, the BRCA1 tumor suppressor gene, the PTEN tumor suppressor gene.

In some embodiments the oligonucleotide agent silences one of the following fusion genes: mLL fusion genes, e.g., mLL-AF9, and thus can be used to treat a subject having or at risk for a disorder characterized by unwanted mLL fusion gene expression, e.g., acute leukemias; the BCR/ABL fusion gene, and thus can be used to treat a subject having or at risk for a disorder characterized by unwanted BCR/ABL fusion gene expression, e.g., acute and chronic leukemias; the TEUAML1 fusion gene, and thus can be used to treat a subject having or at risk for a disorder characterized by unwanted TEUAML1 fusion gene expression, e.g., childhood acute leukemia; the EWS/FLI1 fusion gene, and thus can be used to treat a subject having or at risk for a disorder characterized by unwanted EWS/FLI1 fusion gene expression, e.g., Ewing Sarcoma; the TLS/FUS1 fusion gene, and thus can be used to treat a subject having or at risk for a disorder characterized by unwanted TLS/FUS1 fusion gene expression, e.g., Myxoid liposarcoma; the PAX3/FKHR fusion gene, and thus can be used to treat a subject having or at risk for a disorder characterized by unwanted PAX3/FKHR fusion gene expression, e.g., Myxoid liposarcoma; the AML1/ETO fusion gene, and thus can be used to treat a subject having or at risk for a disorder characterized by unwanted AML1/ETO fusion gene expression, e.g., acute leukemia.

In some aspects herein the compositions comprising the heterogeneous polymeric micelles and an agent, such as a polynucleotide, provide therapeutic agents for treating a subject, e.g., a human, at risk for or afflicted with a disease or disorder that may benefit by angiogenesis inhibition e.g., cancer or retinal degeneration. The treatment comprises providing a heterogeneous polymeric micelle comprising an oligonucleotide agent, wherein said oligonucleotide agent is homologous to and/or can silence, e.g., by cleavage, a gene which mediates angiogenesis (e.g., VEGF-R1, VEGF-R2 or a gene encoding signaling proteins for these receptors' pathways); and administering a therapeutically effective dosage of said heterogeneous polymeric micelle comprising the oligonucleotide agent to a subject, e.g., a human subject.

In some embodiments the oligonucleotide agent silences one of the following genes: the alpha v-integrin gene, and thus can be used to treat a subject having or at risk for a disorder characterized by unwanted alpha V integrin, e.g., brain tumors or tumors of epithelial origin; the Flt-1 receptor gene, and thus can be used to treat a subject having or at risk for a disorder characterized by unwanted Flt-1 receptors, e.g., cancer and rheumatoid arthritis; the tubulin gene, and thus can be used to treat a subject having or at risk for a disorder characterized by unwanted tubulin, e.g., cancer and retinal neovascularization.

In some aspects the composition comprising a heterogeneous polymeric micelles and an oligonucleotide agent relate to a method of treating a subject infected with a virus or at risk for or afflicted with a disorder or disease associated with a viral infection. The method comprises providing a heterogeneous polymeric micelle comprising an oligonucleotide agent, wherein said oligonucleotide agent is homologous to and/or can silence, e.g., by cleavage, a viral gene or a cellular gene which mediates viral function, e.g., entry or growth; and administering a therapeutically effective dose of said oligonucleotide agent to a subject, e.g., a human subject.

In some embodiments, the composition comprising heterogeneous polymeric micelles and an oligonucleotide agent are useful in treatment of subjects infected with the Human Papilloma Virus (HPV) or at risk for or afflicted with a disorder mediated by HPV, e.g., cervical cancer.

In some embodiments, a composition comprising heterogeneous polymeric micelle and an oligonucleotide agent silencing expression of a HPV gene is reduced. In some embodiments, the HPV gene is selected from the group of E2, E6, or E7.

In another embodiment the expression of a human gene that is required for HPV replication is reduced.

In some embodiments, the composition comprises a heterogeneous polymeric micelle and an oligonucleotide agent useful in treating patients infected by the Human Immunodeficiency Virus (HIV) or at risk for or afflicted with a disorder mediated by HIV, e.g., Acquired Immune Deficiency Syndrome (AIDS). In some embodiments, the expression of an HIV gene is reduced. In other embodiments, the HIV gene is CCR5, Gag, or Rev. In some embodiments the expression of a human gene that is required for HIV replication is reduced. In some embodiments, the gene is CD4 or Tsg101.

In some embodiments, the composition comprises a heterogeneous polymeric micelle and an oligonucleotide agent useful for treating patients infected by the Hepatitis B Virus (HBV) or at risk for or afflicted with a disorder mediated by HBV, e.g., cirrhosis and heptocellular carcinoma. In one embodiment, the expression of a HBV gene is reduced. In other embodiment, the targeted HBV gene encodes one of the groups of the tail region of the HBV core protein, the precregious (pre-c) region, or the cregious (c) region. In other embodiments a targeted HBV-RNA sequence is comprised of the poly(A) tail. In some embodiments the expression of a human gene that is required for HBV replication is reduced.

In some embodiments, the composition comprises a heterogeneous polymeric micelle and an oligonucleotide agent useful for treating patients infected with, or at risk for or afflicted with a disorder mediated by a virus selected from the following viruses: the Hepatitis A Virus (HAV); Hepatitis C Virus (HCV); any of the group of Hepatitis Viral strains comprising hepatitis D, E, F, G, or H; the Respiratory Syncytial Virus (RSV); the herpes Cytomegalovirus (CMV); the herpes Epstein Barr Virus (EBV); Kaposi's Sarcoma-associated Herpes Virus (KSHV); the JC Virus (JCV); myxovirus (e.g., virus causing influenza), rhinovirus (e.g., virus causing the common cold), or coronavirus (e.g., virus causing the common cold); the St. Louis Encephalitis flavivirus; the Tick-borne encephalitis flavivirus; the Murray Valley encephalitis flavivirus; the dengue flavivirus; the Simian Virus 40 (SV40); the encephalomyocarditis virus (EMCV); the measles virus (MV); the Varicella zoster virus (VZV); an adenovirus (e.g. virus causing a respiratory tract infection); the poliovirus; or a poxvirus (a poxvirus causing smallpox). In some embodiments the expression of a human gene that is required for the replication of these viruses is reduced.

In some embodiments, the composition comprises a heterogeneous polymeric micelle and an oligonucleotide agent useful for treating patients infected by the Herpes Simplex Virus (HSV) or at risk for or afflicted with a disorder mediated by HSV, e.g., genital herpes and cold sores as well as life-threatening or sight-impairing disease, e.g., mainly in immunocompromised patients. In some embodiments, the expression of a HSV gene is reduced. In other embodiment, the targeted HSV gene encodes DNA polymerase or the helicase-primase. In some embodiments the expression of a human gene that is required for HSV replication is reduced.

In some embodiments, the composition comprises a heterogeneous polymeric micelle and an oligonucleotide agent useful for treating patients infected by the West Nile Virus or at risk for or afflicted with a disorder mediated by West Nile Virus. In some embodiments, the expression of a West Nile Virus gene is reduced. In other preferred embodiments, the West Nile Virus gene is selected from the group comprising E, NS3, or NS5. In some embodiments the expression of a human gene that is required for West Nile Virus replication is reduced.

In some embodiments, the heterogeneous polymeric micelle comprises an oligonucleotide agent useful for treating patients infected by the Human T Cell Lymphotropic Virus (HTLV), or a disease or disorder associated with this virus, e.g., leukemia or myelopathy. In some embodiments, the expression of a HTLV gene is reduced. In some embodiments, the HTLV1 gene is the Tax transcriptional activator. In some embodiments, the expression of a human gene that is required for HTLV replication is reduced.

In some aspects, the composition comprises a heterogeneous polymeric micelle and an oligonucleotide agent useful for treating a subject infected with a pathogen, e.g., a bacterial, amoebic, parasitic, or fungal pathogen. The method of treatment comprises providing a heterogeneous polymeric micelle comprising an oligonucleotide agent, wherein said oligonucleotide is homologous to and/or can silence, e.g., by cleavage of a pathogen gene or a gene involved in the pathogen's growth; and administering a therapeutically effective dose of said oligonucleotide agent to a subject, e.g., a human subject. The target gene can be selected from a gene involved in the pathogen's growth, cell wall synthesis, protein synthesis, transcription, energy metabolism, e.g., the Krebs cycle, or toxin production.

Thus, in some embodiments, the composition comprises a heterogeneous polymeric micelle and an oligonucleotide agent useful for of treating patients infected by a *plasmodium* that causes malaria. In some embodiments, the expression of a *plasmodium* gene is reduced. In other embodiments, the gene is apical membrane antigen 1 (AMA1). In some embodiments, the expression of a human gene that is required for *plasmodium* replication is reduced.

In some embodiments, the heterogeneous polymeric micelle comprises an oligonucleotide agent useful for treating patients infected by *Mycobacterium ulcerans, Mycobacterium tuberculosis, Mycobacterium leprae, Staphylococcus aureus, Streptococcus pneumoniae, Streptococcus pyogenes, Chlamydia pneumoniae, Mycoplasma pneumoniae*, or a disease or disorder associated with any of these pathogens. In some embodiments, the expression of a bacterial gene and/or a human gene that is required for the replication of these bacteria is reduced.

In some embodiments, the diseases treated by the compositions comprising a heterogeneous polymeric micelle and an agent as provided herein may be systemic or present in a specific tissue, e.g., the lung, skin, liver, breast, kidney, pancreas, CNS, or the like. In certain aspects, the oligonucleotide silences a gene which mediates or is involved in a metabolic disease or disorder, e.g., diabetes, obesity, and the like. In certain embodiments, the oligonucleotide silences a gene which mediates or is involved in a pulmonary disease or disorder, e.g., chronic obstructive pulmonary disease (COPD), cystic fibrosis, or lung cancer. In some aspects herein, the heterogeneous polymeric micelles comprise an oligonucleotide agent useful for and/or related to a method of treating a subject, e.g., a human, at risk for or afflicted with a disease or disorder characterized by an unwanted immune response, e.g., an inflammatory disease or disorder or an autoimmune disease or disorder. The method comprises providing a heterogeneous polymeric micelle comprising an oligonucleotide agent, wherein said oligonucleotide agent is homologous to and/or can silence, e.g., by cleavage, a gene which mediates an unwanted immune response; and administering said oligonucleotide agent to a subject, e.g., a human subject. In some embodiments, the disease or disorder is an ischemia or reperfusion injury, e.g., ischemia or reperfusion injury associated with acute myocardial infarction, unstable angina, cardiopulmonary bypass, surgical intervention e.g., angioplasty, e.g., percutaneous transluminal coronary angioplasty, the response to a transplanted organ or tissue, e.g., transplanted cardiac or vascular tissue; or thrombolysis. In other embodiments, the disease or disorder is restenosis, e.g., restenosis associated with surgical intervention e.g., angioplasty, e.g., percutaneous transluminal coronary angioplasty. In other embodiments, the disease or disorder is Inflammatory Bowel Disease, e.g., Crohn Disease or Ulcerative Colitis. In some embodiments, the disease or disorder is inflammation associated with an infection or injury. In other embodiments, the disease or disorder is asthma, allergy, lupus, multiple sclerosis, diabetes, e.g., type II diabetes, arthritis, e.g., rheumatoid or psoriatic. In certain embodiments the oligonucleotide agent silences an integrin or co-ligand thereof, e.g., VLA4, VCAM, ICAM. In other embodiments the oligonucleotide agent silences a selectin or co-ligand thereof, e.g., P-selectin, E-selectin (ELAM), 1-selectin, P-selectin glycoprotein-1 (PSGL-1). In certain embodiments the oligonucleotide agent silences a component of the complement system, e.g., C3, C5, C3aR, C5aR, C3 convertase, and C5 convertase. In some embodiments the oligonucleotide agent silences a chemokine or receptor thereof, e.g., TNFI, TNFJ, IL-1I, IL-1J, 1L-2, IL-2R, IL-4, IL-4R, IL-5, IL-6, IL-8, TNFRI, TNFRII, IgE, SCYA11, and CCR3. In other embodiments the oligonucleotide agent silences GCSF, Gro1, Gro2, Gro3, PF4, MIG, Pro-Platelet Basic Protein (PPBP), MIP-1I, MIP-1J, RANTES, MCP-1, MCP-2, MCP-3, CMBKR1, CMBKR2, CMBKR3, CMBKR5, AIF-1, or I-309.

In some aspects, the composition comprises a heterogeneous polymeric micelle and an oligonucleotide agent useful for treating a subject, e.g., a human, at risk for or afflicted with a neurological disease or disorder. The method comprises providing a heterogeneous polymeric micelle comprising an oligonucleotide agent, wherein said oligonucleotide is homologous to and/or can silence, e.g., by cleavage, a gene which mediates a neurological disease or disorder; and administering a therapeutically effective dose of said oligonucleotide agent to a subject, e.g., a human. In some embodiments the disease or disorder is Alzheimer Disease or Parkinson Disease. In certain embodiments the oligonucleotide agent silences an amyloid-family gene, e.g., APP; a presenilin gene, e.g., PSEN1 and PSEN2, or I-synuclein. In other embodiments the disease or disorder is a neurodegenerative trinucleotide repeat disorder, e.g., Huntington disease, dentatorubral pallidoluysian atrophy or a spinocerebellar ataxia, e.g., SCA1, SCA2, SCA3 (Machado-Joseph disease), SCA7 or SCAB. In some embodiments the oligonucleotide agent silences HD, DRPLA, SCA1, SCA2, MJD1, CACNL1A4, SCA7, or SCA8.

In certain aspects the composition comprises a heterogeneous polymeric micelle and an oligonucleotide agent capable of cleaving or silencing more than one gene. In these embodiments the oligonucleotide agent is selected so that it has sufficient homology to a sequence found in more than one gene, e.g. a sequence conserved between these genes. Thus in some embodiments an oligonucleotide agent targeted to such sequences effectively silences the entire collection of genes.

The following Examples provide various illustrative embodiments of the invention as well as synthesis methods and various biological and other activity parameters. The Examples, however, provide details concerning only some of the embodiments of the invention and are not intended to be limiting.

EXAMPLES

In the following examples, various known acronyms and short-hand notations are used to describe various monomers or monomeric residues derived from polymerization of such monomers. Without limitation, unless otherwise noted: "BMA" (or the letter "B" as equivalent shorthand notation) represents butyl methacrylate or monomeric residue derived therefrom; "DMAEMA" (or the letter "D" as equivalent shorthand notation) represents N,N-dimethylaminoethyl methacrylate or monomeric residue derived therefrom; "Gal" refers to galactose, optionally including hydroxyl-protecting moieties (e.g., acetyl) or to a pegylated derivative thereof (as described below); "MAA" represents methylacrylic acid or monomeric residue derived therefrom; "NHS" represents N-hydroxyl-succinimide or monomeric residue derived therefrom; "PAA" (or the letter "P" as equivalent shorthand notation) represents 2-propylacrylic acid or monomeric residue derived therefrom, "PEGMA" refers to the pegylated methacrylic monomer, methoxy-$(CH_2O)_{7-8}$-methyl)methacrylate or monomeric residue derived therefrom. In each case, any such designation indicates the monomer (including all salts, or ionic analogs thereof), or a monomeric residue derived from polymerization of the monomer (including all salts or ionic analogs thereof), and the specific indicated form is evident by context to a person of skill in the art.

Example 1

General Synthetic Procedures for Preparation of Block Copolymers by Reversible Addition-Fragmentation Chain Transfer (Raft) Polymerization

Example 1.1

Preparation of Block Copolymer [DMAEMA]-[DMAEMA/PAA/BMA]

A. RAFT Chain Transfer Agent (CTA)

The synthesis of the chain transfer agent (CTA), 4-Cyano-4-(ethylsulfanylthiocarbonyl) sulfanylpentanoic acid (ECT), utilized for the following RAFT polymerizations, was adapted from a procedure by Moad et al., *Polymer*, 2005, 46(19): 8458-68. Briefly, ethane thiol (4.72 g, 76 mmol) was added over 10 minutes to a stirred suspension of sodium hydride (60% in oil) (3.15 g, 79 mmol) in diethyl ether (150 ml) at 0° C. The solution was then allowed to stir for 10 minutes prior to the addition of carbon disulfide (6.0 g, 79 mmol). Crude sodium S-ethyl trithiocarbonate (7.85 g, 0.049 mol) was collected by filtration, suspended in diethyl ether (100 mL), and reacted with Iodine (6.3 g, 0.025 mol). After 1 hour the solution was filtered, washed with aqueous sodium thiosulfate, and dried over sodium sulfate. The crude bis (ethylsulfanylthiocarbonyl) disulfide was then isolated by rotary evaporation. A solution of bis-(ethylsulfanylthiocarbonyl) disulfide (1.37 g, 0.005 mol) and 4,4'-azobis(4-cyanopentanoic acid) (2.10 g, 0.0075 mol) in ethyl acetate (50 mL) was heated at reflux for 18 h. Following rotary evaporation of the solvent, the crude 4-Cyano-4(ethylsulfanylthiocarbonyl) sulfanylvpentanoic acid (ECT) was isolated by column chromatography using silica gel as the stationary phase and 50:50 ethyl acetate hexane as the eluent.

B. Poly(N,N-dimethylaminoethyl methacrylate) macro chain transfer agent (polyDMAEMA macroCTA)

The RAFT polymerization of DMAEMA was conducted in DMF at 30° C. under a nitrogen atmosphere for 18 hours using ECT and 2,2'-Azobis(4-methoxy-2.4-dimethyl valeronitrile) (V-70) (Wako chemicals) as the radical initiator. The initial monomer to CTA ratio ([CTA]0/[M]0 was such that the theoretical Mn at 100% conversion was 10,000 (g/mol). The initial CTA to initiator ratio ([CTA]o/[I]o) was 10 to 1. The resultant polyDMAEMA macro chain transfer agent was isolated by precipitation into 50:50 v:v diethyl ether/pentane. The resultant polymer was redissolved in acetone and subsequently precipitated into pentane (×3) and dried overnight in vacuo.

C. Block copolymer [DMAEMA]-[DMAEMA/PAA/BMA] prepared from poly(DMAMEA) macroCTA Desired stoichiometric quantities of N,N-dimethylaminoethyl methacrylate (DMAEMA), propylacrylic acid (PAA), and butylmethacrylate (BMA) were added to poly (DMAEMA) macroCTA dissolved in N,N-dimethylformamide (25 wt % monomer and macroCTA to solvent). For all polymerizations $[M]_o/[CTA]_o$ and $[CTA]_o/[I]_o$ were 250:1 and 10:1 respectively. Following the addition of V70 the solutions were purged with nitrogen for 30 min and allowed to react at 30° C. for 18 h, copolymering the included monomers to form the [DMAEMA/PAA/BMA] random copolymer block. The resultant diblock copolymers were isolated by precipitation into 50:50 v:v diethyl ether/pentane. The precipitated polymers were then redissolved in acetone and subsequently precipitated into pentane (×3) and dried overnight in vacuo.

Gel permeation chromatography (GPC) was used to determine molecular weights and polydispersities ($PD_1$, $M_w/M_n$) of each of the poly(DMAEMA) macroCTA and the [DMAEMA]-[DMAEMA/PAA/BMA] diblock copolymer in DMF with respect to polymethyl methacrylate standards (SEC Tosoh TSK-GEL R-3000 and R-4000 columns (Tosoh Bioscience, Montgomeryville, Pa.) connected in series to a Viscotek GPCmax VE2001 and refractometer VE3580 (Viscotek, Houston, Tex.). HPLC-grade DMF containing 1.0 wt % LiBr was used as the mobile phase.

Table 1.1A and Table 1.1B summarize [DMAEMA]-[DMAEMA/PAA/BMA] block copolymers, prepared by as described herein, having various relative ratios of molecular weights (hydrophilic block:hydrophobic block), and having various compositions of monomeric residues of the hydrophobic block of the RAFT synthesized polymers.

In Tables 1.1A and 1.1B, the letter "D" represents DMAEMA (or monomeric residue derived from DMAEMA), "P" represents PAA (or monomeric residue derived from PAA) and "B" represents BMA (or monomeric residue derived from BMA). With reference to Table 1.1A, polymers referred to therein were previously referred to in certain earlier-filed priority applications by various designations, each indicating that such polymer was a member of a class of polymers generally referred to as "P7" polymers. For example, P7v6, a P7 polymer, has been previously referred to in one or more of such earlier applications as "P7v6" and "PRx0729v6". In Table 1.1.B, particle size was determined by dynamic light scattering, substantially as described in Example 5.

TABLE 1.1A

| Polymer | Structure $[D]_{MW1}\text{-}[B_x\text{-}P_y\text{-}D_z]_{MW2}$ | Mn Kda | Block Ratio $MW_2/MW_1$ |
|---|---|---|---|
| P7v1 | $[D]_{9.1K}\text{-}[B_{48}\text{-}P_{29}\text{-}D_{23}]_{11.37K}$ | 19 | 1.2 |
| P7v2 | $[D]_{10K}\text{-}[B_{46}\text{-}P_{18}\text{-}D_{37}]_{8.9K}$ | 19 | 0.9 |
| P7v3 | $[D]_{6.5K}\text{-}[B_{41}\text{-}P_{39}\text{-}D_{20}]_{9.5K}$ | 16 | 1.5 |
| P7v6 | $[D]_{9.1K}\text{-}[B_{52}\text{-}P_{26}\text{-}D_{22}]_{21.9K}$ | 31 | 2.4 | x, y, z are mole %. Molecular weights were determined by gel permeation chromatography using PMMA standards. Compositions were determined by NMR spectroscopy.

TABLE 1.1B

| Polymer | Structure $[D]_{MW1}\text{-}[B\text{-}P\text{-}D_{mole}\%]_{MW2}$ | Block Ratio $MW_2/MW_1$ | Particle Size (nm) |
|---|---|---|---|
| PRx-1 | $[D]_{11.3K}\text{-}[B_{50}\text{-}P_{30}\text{-}D_{20}]_{20.7K}$ | 1.83 | 41 |
| PRx-2 | $[D]_{14.5K}\text{-}[B_{57}\text{-}P_{23}\text{-}D_{20}]_{26.4K}$ | 1.82 | 49 |
| PRx-3 | $[D]_{11.5K}\text{-}[B_{35}\text{-}P_{27}\text{-}D_{38}]_{33.4K}$ | 2.92 | 60 |
| PRx-4 | $[D]_{10.7K}\text{-}[B_{50}\text{-}P_{27}\text{-}D_{23}]_{33.8K}$ | 3.16 | 50 |
| PRx-5 | $[D]_{10.7K}\text{-}[B_{40}\text{-}P_{31}\text{-}D_{29}]_{32.2K}$ | 3.00 | 59 |
| PRx-6 | $[D]_{14.5K}\text{-}[B_{53}\text{-}P_{31}\text{-}D_{16}]_{67.0K}$ | 4.62 | 115 |

Example 1.2

Preparation of block copolymer [PEGMA]-[DMAEMA/PAA/BMA]

A. RAFT Chain Transfer Agent (CTA)

The chain transfer agent (CTA), 4-Cyano-4-(ethylsulfanylthiocarbonyl) sulfanylpentanoic acid (ECT), was prepared as described in Example 1.1A.

B. Poly(methoxy-$(CH_2O)_{7-8}$-methyl)methacrylate) macro chain transfer agent (polyPEGMA macroCTA)

The polyPEGMA macro CTA was prepared by RAFT polymerization of methoxy-$(CH_2O)_{7-8}$-methyl)methacrylate (PEGMA) monomer substantially as described in Example 1.1B (using PEGMA in place of DMAEMA).

C. Block copolymer of [PEGMA]-[DMAEMA/PAA/BMA] from poly(PEGMA) macroCTA

Figure 2:
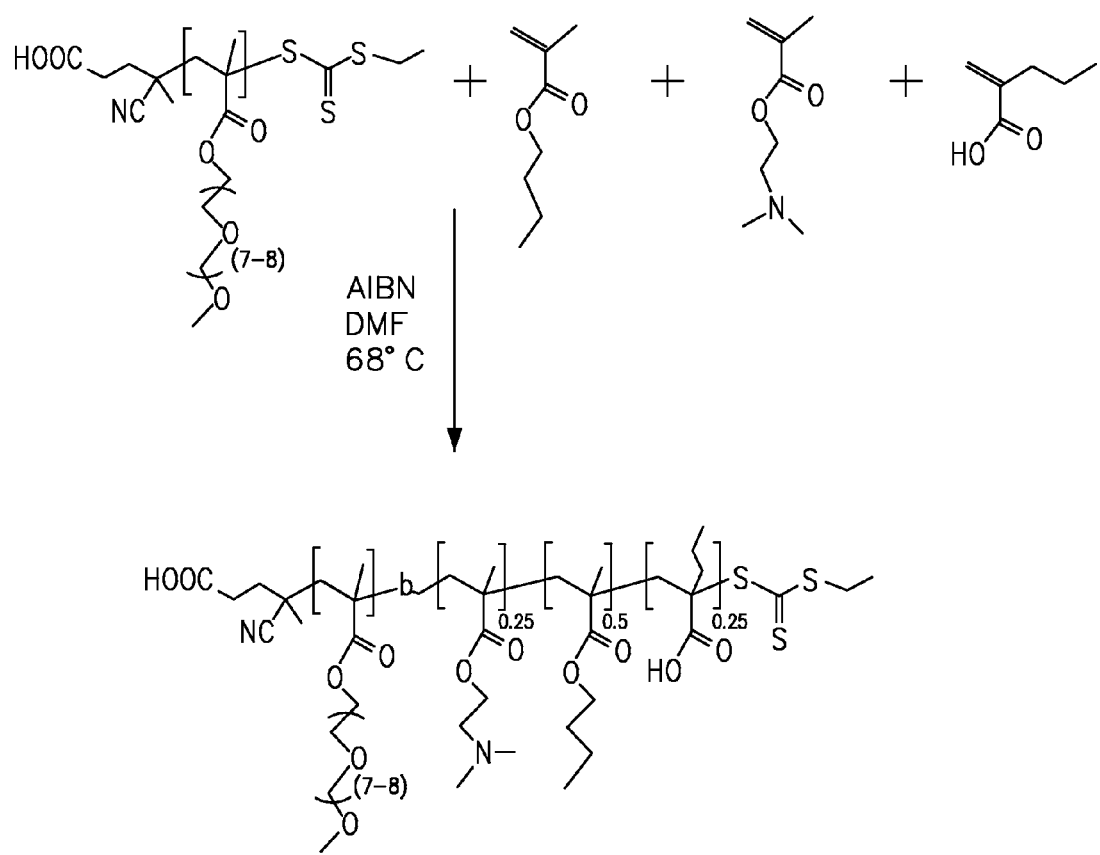
FIG. 2 is a schematic illustration of a reaction scheme for preparing block copolymer [PEGMA]-[DMAEMA/PAA/BMA] from poly(PEGMA) macroCTA and DMAEMA, PAA and BMA monomers using living radical polymerization (e.g., reversible addition-fragmentation chain transfer (RAFT)) polymerization.

Desired stoichiometric quantities of DMAEMA, PAA, and BMA were added to poly(PEGMA) macroCTA dissolved in N,N-dimethylformamide (25 wt % monomer and macroCTA to solvent). For all polymerizations $[M]_o/[CTA]_o$ and $[CTA]_o/[I]_o$ were 250:1 and 10:1 respectively. Following the addition of AIBN the solutions were purged with nitrogen for 30 min and allowed to react at 68° C. for 6-12 h, copolymerizing the included monomers to form the [DMAEMA/PAA/BMA] random copolymer block, as represented schematically in FIG. 2. The resulting diblock copolymers were isolated by precipitation into 50:50 v:v diethyl ether/pentane. The precipitated polymers were then redissolved in acetone and subsequently precipitated into pentane (×3) and dried overnight in vacuo.

Gel permeation chromatography (GPC) was used to determine molecular weights and polydispersities (PDI, $M_w/M_n$) of each of the poly(PEGMA) macroCTA and the [PEGMA]-[DMAEMA/PAA/BMA] diblock copolymer in DMF using a Viscotek GPCmax VE2001 and refractometer VE3580 (Viscotek, Houston, Tex.). HPLC-grade DMF containing 1.0 wt % LiBr was used as the mobile phase. NMR spectroscopy in $CDCl_3$ was used to confirm the polymer structure and calculate the composition of the second hydrophobic block, [DMAEMA/PAA/BMA].

FIG. 3A summarizes characteristics of a representative [$PEGMA_w$]-[DMAEMA/PAA/BMA] block copolymer, polymer 4.8 prepared by as described herein (also designated as "P7-PEGMA 100" in FIG. 3A), where the "w" subscript on the notation "$PEGMA_w$" refers to the number of polyethylene glycol repeat units pendant from the methacrylate monomeric residue. In this context for example, the block notation [$PEGMA_w$] where w=7-8, refers to a block comprising monomeric residues derived from poly(methoxy-$(CH_2O)_{7-8}$-methyl) methacrylate (see FIG. 2). FIG. 3A reports number-average molecular weight, Mn, and polydispersity index (PDI) for the hydrophilic first block [$PEGMA_w$], and the hydrophobic second block [DMAEMA/PAA/BMA], as well as the relative composition of monomeric residues of the second block of this polymer. FIG. 3B shows the $^1H$ NMR data for the polymer P7-PEGMA 100, such data being obtained substantially as described in Example 5. FIG. 3C shows the GPC data obtained as described herein above, including traces from refractive index (RI) and light scattering (LS) detectors.

Example 2 and Example 3

Methods for Conjugating Targeting Ligands and Polynucleotides to Block Copolymers Example 2 and Example 3 demonstrate methods for conjugating a representative targeting ligand (for example, galactose) to a block copolymer as an alpha end-targeting moiety thereof, or (additionally or alternatively) for conjugating a targeting ligand through one or more pendant moieties of representative conjugatable monomeric residues (e.g., MAA (NHS)). Example 3 also demonstrates conjugation of a polynucleotide (for example siRNA, e.g., as a therapeutic of interest) to a block copolymer. Briefly: (1) The block copolymer was prepared using reversible addition fragmentation chain transfer (RAFT) (Chiefari et al. *Macromolecules.* 1998; 31(16):5559-5562) polymerization. Specifically, a galactose alpha-end-functionalized, diblock copolymer was formed using a chain transfer agent having galactose as the leaving group, $R_L$, substituent. (2) A first hydrophilic block of the diblock copolymer was prepared as a copolymer containing methylacrylic acid-N-hydroxy succinimide (MAA(NHS)), where a galactose-PEG-amine was conjugated to the NHS groups or where an amino-disulfide siRNA was conjugated to the NHS, or where pyridyl disulfide amine was reacted with the NHS groups to form a pyridyl disulfide that was subsequently reacted with thiolated RNA to form a polymer-RNA conjugate.

Example 2.1

Preparation of galactose-PEG-amine and galactose-CTA

Scheme 1, below, illustrates a synthesis scheme for galactose-PEG-amine (compound 3) and the galactose-CTA (chain transfer agent) (compound 4).

A. Compound 1:

Pentaacetate galactose (10 g, 25.6 mmol) and 2-[2-(2-Chloroethoxy)ethoxy]ethanol (5.6 mL, 38.4 mmol) were dissolved in dry $CH_2Cl_2$ (64 mL) and the reaction mixture was stirred at RT for 1 h. The $BF_3.OEt_2$ (9.5 ml, 76.8 mmol) was added to the previous mixture dropwise over 1 h in an ice bath. The reaction mixture was stirred at room temperature (RT) for 48 h. After the reaction, 30 mL of $CH_2Cl_2$ was added to dilute the reaction. The organic layer was neutralized with saturated $NaHCO_{3(aq)}$, washed by brine and then dried by $MgSO_4$. The $CH_2Cl_2$ was removed under reduced pressure to get the crude product. The crude product was purified by flash column chromatography to obtain intermediate product (compound 1) as slight yellow oil. Yield: 55% TLC ($I_2$ and p-Anisaldhyde): EA/Hex: 1/1 (Rf: β=0.33; α=0.32; unreacted S.M 0.30).

B. Compound 2:

Compound 1 (1.46 g, 2.9 mmol) was dissolved in dry DMF (35 mL) and $NaN_3$ (1.5 g, 23.2 mmol) was added to the mixture at RT. The reaction mixture was heated to 85-90 C. overnight. After the reaction, EA (15 mL) was added to the solution and water (50 mL) was used to wash the organic layer 5 times. The organic layer was dried by $MgSO_4$ and purified by flash column chromatography to get compound 2 as a colorless oil. Yield: 80%, TLC ($I_2$ and p-Anisaldhyde): EA/Hex: 1/1 (Rf: 0.33).

C. Compound 3:

Compound 2 (1.034 g, 2.05 mmol) was dissolved in MeOH (24 mL) and bubbled with $N_2$ for 10 min and then Pd/C (10%) (90 mg) and TFA (80 uL) were added to the previous solution. The reaction mixture was bubbled again with $H_2$ for 30 min and then the reaction was stirred at RT under $H_2$ for another 3 h. The Pd/C was removed by celite and MeOH was evaporated to get the compound 3 as a sticky gel. Compound 3 can be used without further purification. Yield: 95%. TLC (p-Anisaldhyde): MeOH/$CH_2Cl_2$: 1/4 (Rf: 0.05).

D. Compound 4:

ECT (0.5 g, 1.9 mmol), NHS (0.33 g, 2.85 mmol) and DCC (0.45 g, 2.19 mmol) were dissolved in $CHCl_3$ (15 mL) at 0 C. The reaction mixture was continuously stirred at RT overnight. Compound 3 (1.13 g, 1.9 mmol) and TEA (0.28 mL, 2.00 mmol) in $CHCl_3$ (10 mL) were added slowly to the previous reaction at 0 C. The reaction mixture was continuously stirred at RT overnight. The $CH_3Cl$ was removed under reduced pressure and the crude product was purified by flash column chromatography to get the compound 4 as a yellow gel. Yield (35%). TLC: MeOH/$CH_2Cl_2$: 1/9 (Rf: 0.75).

Scheme 1.
Synthesis of galactose-PEG-amine (cpd 3) and galatose-CTA (cpd 4)

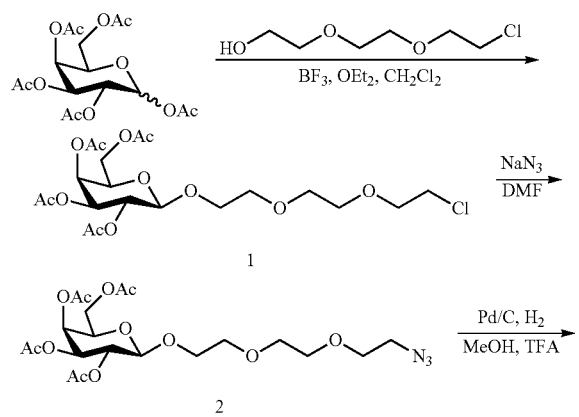

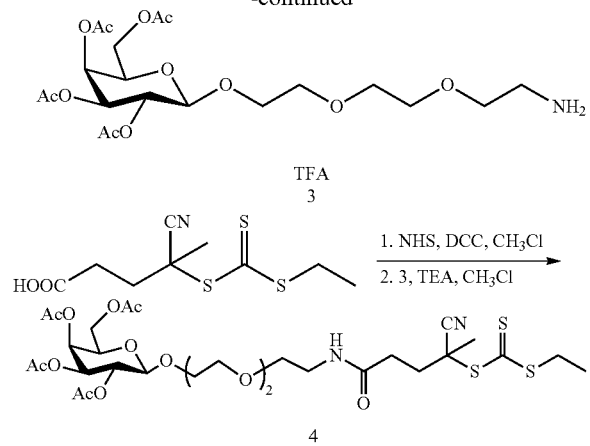

Example 2.2

Synthesis of block copolymer
[DMAEMA]-[BMA-PAA-DMAEMA]

A. Synthesis of DMAEMA macroCTA

Polymerization (Table 2.2A): In a 20 mL glass vial (with a septa cap) was added 33.5 mg ECT (RAFT CTA), 2.1 mg AIBN (recrystallized twice from methanol), 3.0 g DMAEMA (Aldrich, 98%, was passed through a small alumina column just before use to remove the inhibitor) and 3.0 g DMF (high purity without inhibitor). The glass vial was closed with the Septa Cap and purged with dry nitrogen (carried out in an ice bath under stirring) for 30 min. The reaction vial was placed in a preheated reaction block at 70° C. The reaction mixture was stirred for 2 h 40 min. The septa cap was opened and the mixture was stirred in the vial in an ice bath for 2-3 minutes to stop the polymerization reaction.

Purification: 3 mL of acetone was added to the reaction mixture. In a 300 mL beaker was added 240 mL hexane and 60 mL ether (80/20 (v/v)) and under stirring the reaction mixture was added drop by drop to the beaker. Initially this produced an oil which was collected by spinning down the cloudy solution; yield=1.35 g (45%). Several precipitations were performed (e.g., 6 times) in hexane/ether (80/20 (v/v)) mixed solvents from acetone solution. Finally, the polymer was dried under vacuum for 8 h at RT; yield≈1 g. Summary: ($M_{n,theory}$=11,000 g/mol at 45% conv.)

TABLE 2.2A

| Name | FW (g/mol) | Equiv. | mol | Weight | Actual weight |
|---|---|---|---|---|---|
| DMAEMA | 157.21 | 150 | 0.0191 | 3.0 g | 3.01 g |
| ECT | 263.4 | 1 | $1.2722 \times 10^{-4}$ | 33.5 mg | 33.8 mg |
| AIBN | 164.21 | 0.1 | $1.2722 \times 10^{-5}$ | 2.1 mg | 2.3 mg |

DMF = 3.0 g; $N_2$ Purging: 30 min; polymerization at 70° C. for 2 h 45 min.

B. Synthesis of block copolymer
[DMAEMA]-[BMA-PAA-DMAEMA] from
DMAEMA macroCTA

All chemicals and reagents were purchased from Sigma-Aldrich Company unless specified. Butyl methacrylate (BMA) (99%), 2-(Dimethylamino) ethyl methacrylate (DMAEMA) (98%) were passed through a column of basic alumina (150 mesh) to remove the polymerization inhibitor. 2-propyl acrylic acid (PAA) (>99%) was purchased from without inhibitor and used as received. Azobisisobutyronitrile (AIBN) (99%) was recrystallized from methanol and dried under vacuum. The DMAEMA macroCTA was synthesized and purified as described above in Example 2.2A (Mn~10000; PDI~1.3; >98%). N,N-Dimethylformamide (DMF) (99.99%) (Purchased from EMD) was reagent grade and used as received. Hexane, pentane and ether were purchased from EMD and they were used as received for polymer purification.

Polymerization: BMA (2.1 g, 14.7 mmoles), PAA (0.8389 g, 7.5 mmoles), DMAEMA (1.156 g, 7.35 mmoles), DMAEMA macroCTA (0.8 g, 0.0816 mmoles), AIBN (1.34 mg, 0.00816 mmoles; CTA:AIBN 10:1) and DMF (5.34 ml) were added under nitrogen in a sealed vial. The CTA:Monomers ratio used was 1:360 (assuming 50% of conversion). The monomers concentration was 3 M. The mixture was then degassed by bubbling nitrogen into the mixture for 30 minutes and then placed in a heater block (Thermometer: 67° C.; display: 70-71; stirring speed 300-400 rpm). The reaction was left for 6 hours, then stopped by placing the vial in ice and exposing the mixture to air.

Purification: Polymer purification was done from acetone/DMF 1:1 into hexane/ether 75/25 (three times). The resulting polymer was dried under vacuum for at least 18 hours. The NMR spectrum showed a high purity of the polymer. No vinyl groups were observed. The polymer was dialysed from ethanol against double de-ionized water for 4 days and then lyophilized. The polymer was analyzed by gel permeation chromatography (GPC) using the following conditions: Solvent: DMF/LiBr 1%. Flow rate: 0.75 ml/min. Injection volume: 100 µl. Column temperature: 60° C. Poly (styrene) was used to calibrate the detectors. GPC analysis of the resulting Polymer: Mn=40889 g/mol. PDI=1.43. dn/dc=0.049967.

Example 2.3

Synthesis of gal-[DMAEMA]-[BMA-PAA-DMAEMA]

Figure 4:
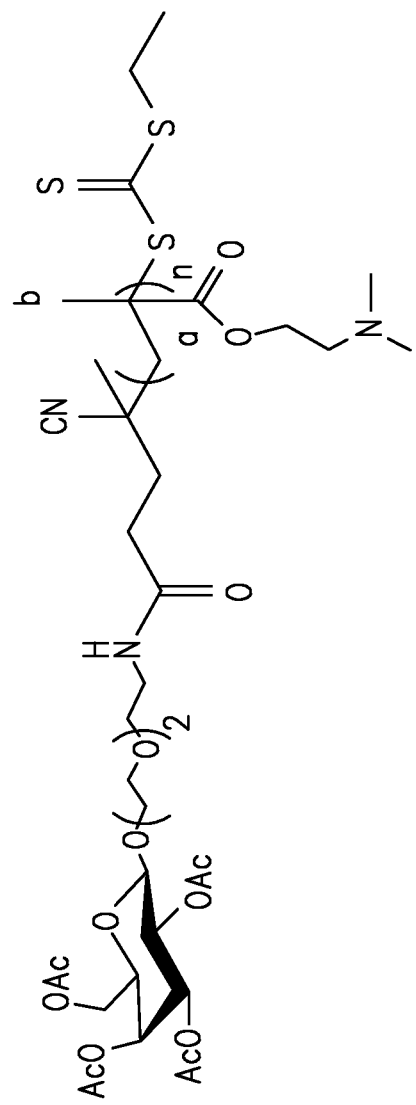
FIG. 4 is a formula representing an acetyl-protected, PEGylated galactose-[DMAEMA] macro-CTA suitable for living radical (RAFT) polymerization to prepare block copolymers having galactose (e.g., as targeting moiety) conjugated to the alpha end of such block copolymers.

Synthesis was carried out substantially as described in Example 2.2, with exceptions as noted. First, a galactose-[DMAEMA] macro-CTA was prepared substantially as described in Example 2.2.A except that a galactose-CTA (Example 2.1, cpd 4) was used in place of ECT as the chain transfer agent, resulting in polyDMAEMA with an alpha-end functionalized galactose (FIG. 4). The galactose-[DMAEMA]-macro-CTA was then used to synthesize the second block [BMA-PAA-DMAEMA] substantially as described in Example 2.2.B. Following synthesis, the acetyl protecting groups on the galactose were removed by incubation in 100 mM sodium bicarbonate buffer, pH 8.5 for 2 hrs, followed by dialysis and lyophilization. NMR spectroscopy was used to confirm the presence of the deprotected galactose on the polymer.

Example 2.4

Preparation of block copolymers [PEGMA/MAA(NHS)]-[BMA/PAA/DMAEMA] and DMAEMA-MMA(NHS)-[BMA/PAA/DMAEMA]

Polymer synthesis was performed substantially as described in Example 2.2.

Briefly, the first [PEGMA/MAA(NHS)] block was prepared using PEGMA and MAA(NHS) monomers with the monomer feed ratios controlled to obtain various desired compositions of [PEGMA/MAA(NHS)]-[BMA/PAA/DMAEMA] polymer. As a representative block copolymer, for example, the co-polymerization ratio of monomers in the $1^{st}$ block was, for example, 70:30 (PEGMA:MAA(NHS)).

The [DMAEMA/MMA(NHS)] first block of the second polymer was prepared similarly using DMAEMA and MAA (NHS) monomers with the monomer feed ratios controlled to obtain various desired compositions of [DMAEMA/MAA(NHS)]-[BMA/PAA/DMAEMA] polymer. As an representative block copolymer, for example, the co-polymerization ratio of monomers in the $1^{st}$ block can be, for example, 70:30 for DMAEMA:MAA(NHS).

Example 3.1

Conjugation of galactose-PEG-amine to block copolymers (i) [DMAEMA/MAA(NHS)]-[BMA/PAA/DMAEMA] or (ii) [PEGMA/MAA(NHS)]-[BMA/PAA/DMAEMA] to produce galactose-functionalized block copolymers (i) [DMAEMA/MAA(Gal)]-[BMA/PAA/DMAEMA] or (ii) [PEGMA-MAA(Gal)]-[BMA-PAA-DMAEMA]

Example 3.1

Figure 5:
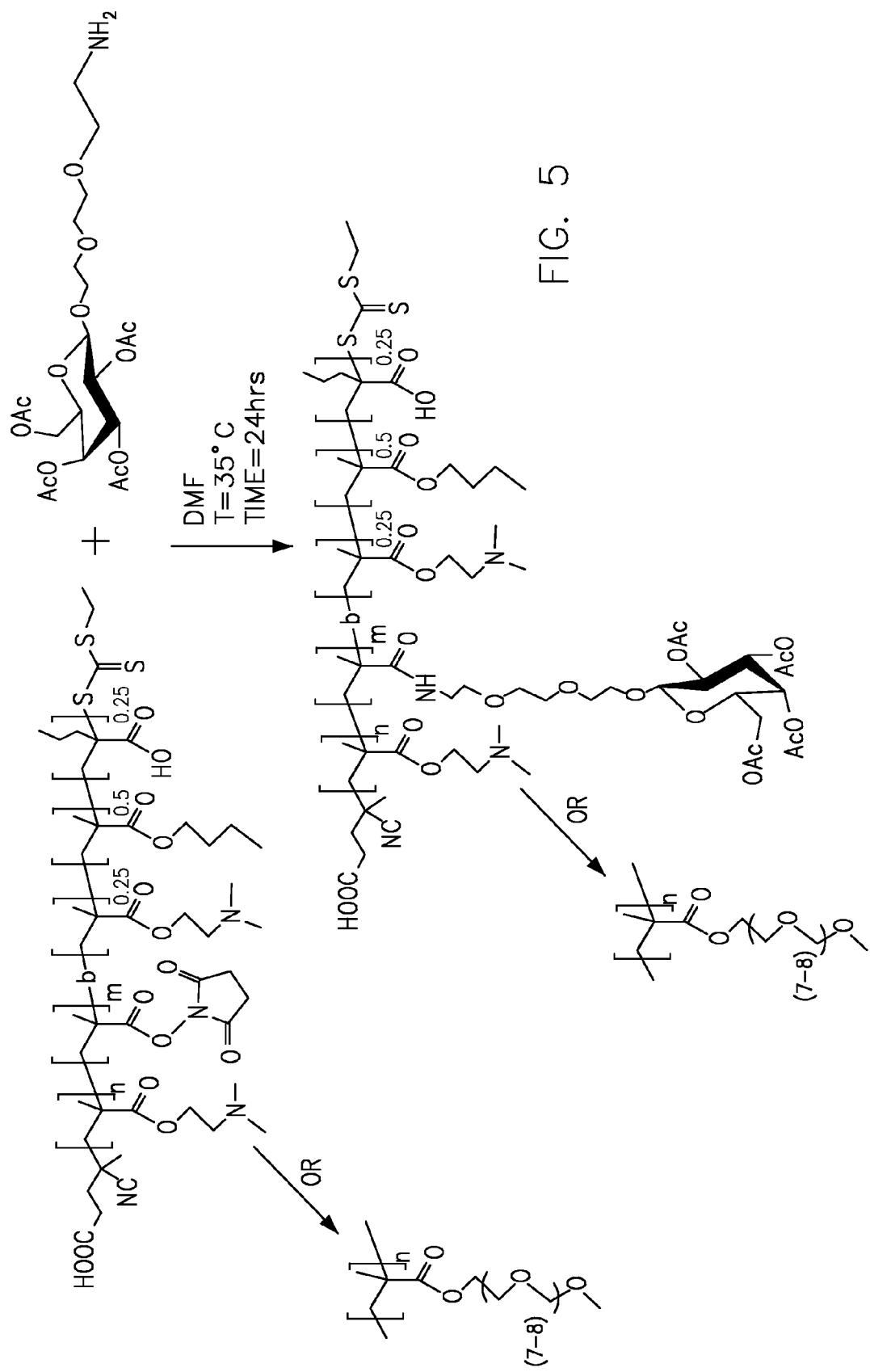
FIG. 5 is a schematic illustration of a reaction scheme for preparing (acetyl-protected, PEGylated) galactose-functionalized block copolymers by reaction of block copolymers having monomeric residues derived MAA(NHS) or MAA (NHS) with (acetyl-protected, PEGylated) amine-functionalized galactose, whereby such block copolymers comprise (acetyl-protected, PEGylated) galactose (e.g., as targeting moieties) conjugated pendant to monomeric residues thereof.

FIG. 5 illustrates the preparation of galactose functionalized block copolymers (i) [DMAEMA/MAA(Gal)]-[BMA/PAA/DMAEMA] or (ii) [PEGMA-MAA(Gal)]-[BMA/PAA/DMAEMA]. Polymer [DMAEMA-MAA(NHS)]-[B-P-D] or [PEGMA-MAA(NHS)]-[B-P-D] (in each case where [B-P-D] is shorthand notation representing a [BMA/PAA/DMAEMA] block) was prepared substantially as in Example 2.4, and was dissolved in DMF at a concentration between 1 and 20 mg/ml. Galactose-PEG-amine prepared as described in Example 2.1 (cpd 3) was neutralized with 1-2 equivalents of triethylamine and added to the reaction mixture at a ratio of 5 to 1 amine to polymer. The reaction was carried at 35° C. for 6-12 hrs, followed by addition of an equal volume of acetone, dialysis against deionized water for 1 day and lyophilization.

Example 3.2

Conjugation of siRNA to PEGMA-MAA(NHS)]-[BMA/PAA/DMAEMA] to produce block copolymer [PEGMA-MAA(RNA)]-[BMA/PAA/DMAEMA]

Figure 6A:
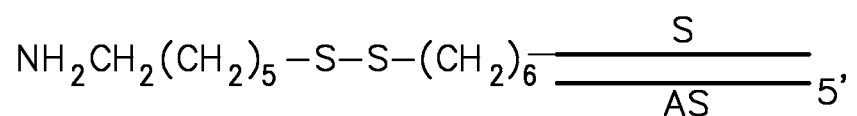
FIG. 6A through 6C are formulas representing 5'-modified polynucleotides (e.g., siRNAs) conjugatable to NHS-containing polymers), including 5'-amino-disulfide-modified polynucleotide (FIG. 6A) and thiolated polynucleotide (FIG. 6B), and a formula representing the structure of 2-ethylamino-pyridyl disulfide.
Figure 6B:
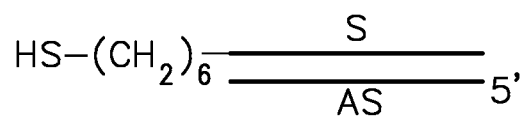
Figure 6C:
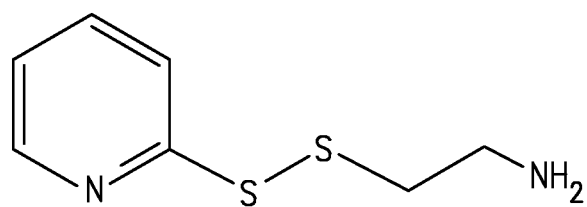

FIG. 6A and FIG. 6B shows the structures of 5'-modified siRNAs conjugatable to NHS-containing polymers, such as block copolymers prepared as described in Example 2.4. FIG. 6 C shows the structure of 2-ethylamino-pyridyl disulfide suitable to derivatize NHS-containing polymers, thereby providing a disulfide reactive group for conjugation of thiolated RNA (FIG. 6 B)

A. Reaction of NHS-containing block copolymers with amino-disulfide-siRNA.

(Prophetic) NHS-containing block copolymers (e.g., prepared as in Example 2.4) are reacted with amino-disulfide-siRNA (e.g., FIG. 6A). The reaction is carried out under standard conditions consisting of an organic solvent (for example, DMF or DMSO, or a mixed solvent DMSO/buffer pH 7.8.) at 35° C. for 4-8 hrs, followed by addition of an equal volume of acetone, dialysis against deionized water for 1 day and lyophilization.

B. Reaction of NHS-containing block copolymers with pyridyl-disulfide-amine and reaction with thiolated siRNA. (Prophetic)

Reaction of pyridyl disulfide amine (FIG. 6C) with NHS containing polymers (e.g., prepared as in Example 2.4) is carried out substantially as described in Example 3. Subsequently the lyophilized polymer is dissolved in ethanol at 50 mg/ml and diluted 10-fold in sodium bicarbonate buffer at pH 8. Thiolated siRNA (FIG. 6B) is reacted at a 2-5 molar excess over polymer NHS groups at 35° C. for 4-8 hrs, followed by dialysis against phosphate buffer, pH 7.4.

Example 3.3

Ionic association of siRNA to block copolymer (e.g., [PEGMA/DMAEMA]-[BMA/PAA/DMAEMA]

Negatively charged siRNA were ionically associated with cationic monomeric residues, (e.g., derived from polymerization of DMAEMA), as more fully described in Example 4 and Example 6. Various desired ratios of siRNA to polymer were evaluated; each was mixed in the desired buffer at the desired pH (e.g. physiologically relevant pH).

Example 4

Preparation of Heterogeneous Polymeric Micelles; Compositions of Heterogeneous Polymeric Micelles and Polynucleotides Associated Therewith Various heterogeneous (mixed) polymeric micelle were prepared, each comprising at least two compositionally distinct block copolymers. Each of a first and second block copolymer comprised a predominantly hydrophilic shell block and a predominantly hydrophobic core block. The first and second block copolymer were combined in defined ratios under denaturing solvent conditions and then transferred to aqueous solvent conditions and allowed to associate to form the heterogeneous (mixed) polymer micelle. In the various examples disclosed herein, relative molecular weights, number of monomeric units, and compositions of the blocks within a given first polymer copolymer or a second block copolymer were varied to achieve micelle stability and biological functionality. In some examples disclosed herein, a mixed micelle containing two block copolymers having substantially the same hydrophobic blocks and having compositionally distinct hydrophilic blocks (e.g., one hydrophilic block comprising monomeric units derived from DMAEMA and the other hydrophilic block comprising monomeric units derived from PEGMA were formed, with various selected ratios of the first block copolymer to the second block copolymer (e.g., a 50:50 ratio), whereby the cationic surface charge density of such mixed micelle was modulated (e.g., reduced relative to a homogeneous micelle having a hydrophilic block consisting essentially of, for example, monomeric residues derived from DMAEMA) and partially shielded (e.g., in this exemplary embodiment by the inclusion of a block copolymer having a hydrophilic block including monomeric units derived from PEGMA). Hence, these examples demonstrate heterogeneous micelles having (i) varied (tunable) block copolymer composition (e.g., as compared between hydrophilic blocks) (ii) varied (tunable) relative ratios of hydrophilic block and hydrophilic blocks (e.g., resulting in varied relative hydrophilic chain lengths as compared between hydrophilic blocks—e.g., in the aforementioned examples as compared between PEGMA block of one block copolymer and the DMAEMA block of another block copolymer (, and (iii) varied (tunable) relative ratios of the number of polymer molecules of the first block copolymer to the second block copolymer. As demonstrated in subsequent examples, optimization of micelle surface charge and shielding were determined to be important factors affecting in vivo efficacy and in vivo toxicity of polymeric micelle delivery vehicles for polynucleotides (e.g., siRNA) for example for therapeutic or other purposes.

A. Block Copolymer Synthesis.

Various compositionally distinct block copolymers were prepared, as follows.

A.1 A block copolymer, designated as polymer 4.1 comprising a DMAEMA cationic hydrophilic block (MW=14,000) and a hydrophobic block (MW=30,000) comprised of a random copolymer of BMA, PAA, and DMAEMA at the indicated % molar ratios, $$[D]_{14K}-[B_{50}-P_{25}-D_{25}]_{30K} \quad (4.1)$$

was prepared by RAFT polymerization substantially as described in Example 2.2. In some examples, polymer 4.1 is alternatively referred to herein as polymer P7-2.

Another block copolymer, designated as polymer 4.6, and similarly constituted to polymer 4.1—albeit having a different relative molecular weight ratio of hydrophilic block to hydrophobic block $$[D]_{10K}-[B_{50}-P_{25}-D_{25}]_{30K} \quad (4.6)$$

was prepared in substantially the same manner as polymer 4.1. In some examples, polymer 4.6 is alternatively referred to herein as polymer P7-4.

A.2. A block copolymer, designated as polymer 4.2 comprising a PEGMA neutral polar hydrophilic block (MW=24,000), and a hydrophobic block (MW=30,000) comprised of a random copolymer of BMA, PAA, and DMAEMA at the indicated % molar ratios, $$[PEGMA]_{24K}-[B_{50}-P_{25}-D_{25}]_{30K} \quad (4.2)$$

was prepared by RAFT polymerization substantially as described in Example 2.2, except that polyPEGMA macro CTA was used in place of polyDMAEMA macro CTA, and was prepared by RAFT polymerization of methoxy-(CH$_2$O)$_{7-8}$-methyl)methacrylate (PEGMA) monomer substantially as described in Example 1.1B using PEGMA in place of DMAEMA.

Additional block copolymers, designated as polymers 4.7 and 4.8, and similarly constituted to polymer 4.2—albeit having a different relative molecular weight ratio of hydrophilic block to hydrophobic block, $$PEGMA]_{18K}-[B_{50}-P_{25}-D_{25}]_{30K} \quad (4.7)$$

$$[PEGMA]_{40K}-[B_{53}-P_{26}-D_{21}]_{60K} \quad (4.8)$$

were prepared in substantially the same manner as polymer 4.2. The polymer 4.8 is also referred to herein as "P7-PEGMA-100"

A.3. A block copolymer, designated as polymer 4.3 comprising a DMAEMA cationic hydrophilic block (MW=14,000) and a hydrophobic block (MW=30,000) comprised of a homopolymer of BMA, $$[D]_{14K}-[B]_{30K} \quad (4.3)$$

was prepared by RAFT polymerization substantially as described in Example 2.2, except that the hydrophobic block was prepared as a homopolymer of BMA (rather than as a random copolymer of BMA, PAA and DMAEMA).

A.4. A block copolymer, designated as polymer 4.4 comprising a hydrophilic block comprised of a random copolymer of PEGMA and MAA(NHS) at a 70:30 molar ratio of PEGMA:MAA(NHS) monomers (MW=24,000), and a hydrophobic block (MW=30,000) comprised of a random copolymer of BMA, PAA, and DMAEMA at the indicated % molar ratios, $$[PEGMA_{70}\text{-}MAA(NHS)_{30}]_{24K}\text{-}[B_{50}\text{-}P_{25}\text{-}D_{25}]_{30K} \quad (4.4)$$

was prepared by RAFT polymerization substantially as described in Example 2.4.

The block copolymer 4.4 described in Example 4.A.4 can be further modified by conjugating a targeting ligand (e.g., Galactose) or a polynucleotide (e.g., siRNA), in each case preferably containing a free amino group (e.g., galactosamine, e.g., amino modified siRNA) to the NHS ester, as described in Example 3.1 (galactose-functionalized block copolymer) and Example 3.2 (siRNA-conjugated block copolymer), to form the block copolymers designated as polymer 4.4.1 and 4.4.2, respectively:

$$[PEGMA_{70}\text{-}MAA(Gal)_{30}]_{24K}\text{-}[B_{50}\text{-}P_{25}\text{-}D_{25}]_{30K} \quad (4.4.1)$$

$$[PEGMA_{70}\text{-}MAA\text{-}(RNA)_{30}]_{24K}\text{-}[B_{50}\text{-}P_{25}\text{-}D_{25}]_{30K} \quad (4.4.2)$$

A.5. A block copolymer, designated as polymer 4.5 comprising a cationic shielded hydrophilic block, [PEGMA/DMAEMA], (MW=24,000) comprised of a random copolymer of PEGMA and DMAEMA at a 70:30 molar ratio of PEGMA:DMAEMA monomers, and a hydrophobic block (MW=30,000) comprised of a random copolymer of BMA, PAA, and DMAEMA at the indicated % molar ratios, $$[PEGMA_{70}\text{-}DMAEMA_{30}]_{24K}\text{-}[B_{50}\text{-}P_{25}\text{-}D_{25}]_{30K} \quad (4.5)$$

was prepared by RAFT polymerization as described in Example 2.2, except that poly[PEGMA/DMAEMA] macro CTA was used in place of polyDMAEMA macro CTA, and was prepared by RAFT random copolymerization of methoxy-$(CH_2O)_{7-8}$-methyl)methacrylate (PEGMA) monomer and DMAEMA monomer substantially as described in Example 1.1B (using PEGMA as a co-monomer with DMAEMA). For reference, the block polymers of this example are summarized in Table 4.A (including alternative designations used in various other examples or figures).

TABLE 4.A

| Example | Polymer | Desig. | Alt. Desig. |
|---|---|---|---|
| Ex. 4.A.1 | $[D]_{14K}\text{-}[B_{50}\text{-}P_{25}\text{-}D_{25}]_{30K}$ | (4.1) | P7-2 |
| Ex. 4.A.2 | $[PEGMA]_{24K}\text{-}[B_{50}\text{-}P_{25}\text{-}D_{25}]_{30K}$ | (4.2) | |
| Ex. 4.A.3 | $[D]_{14K}\text{-}[B]_{30K}$ | (4.3) | |
| Ex. 4.A.4 | $[PEGMA_{70}\text{-}MAA(NHS)_{30}]_{24K}\text{-}$ $[B_{50}\text{-}P_{25}\text{-}D_{25}]_{30K}$ | (4.4) | |
| Ex. 4.A.4 | $[PEGMA_{70}\text{-}MAA(Gal)_{30}]_{24K}\text{-}$ $[B_{50}\text{-}P_{25}\text{-}D_{25}]_{30K}$ | (4.4.1) | |
| Ex. 4.A.4 | $[PEGMA_{70}\text{-}MAA\text{-}(RNA)_{30}]_{24K}\text{-}$ $[B_{50}\text{-}P_{25}\text{-}D_{25}]_{30K}$ | (4.4.2) | |
| Ex. 4.A.5 | $[PEGMA_{70}\text{-}DMAEMA_{30}]_{24K}\text{-}$ $[B_{50}\text{-}P_{25}\text{-}D_{25}]_{30K}$ | (4.5) | |
| Ex. 4.A.1 | $[D]_{10K}\text{-}[B_{50}\text{-}P_{25}\text{-}D_{25}]_{30K}$ | (4.6) | P7-4 |
| Ex. 4.A.2 | $[PEGMA]_{18K}\text{-}[B_{50}\text{-}P_{25}\text{-}D_{25}]_{30K}$ | (4.7) | |
| Ex. 4.A.2 | $[PEGMA]_{40K}\text{-}[B_{53}\text{-}P_{26}\text{-}D_{21}]_{60K}$ | (4.8) | PEGMA 100 |

B. Mixed Polymeric Micelle Formulation; Compositions Comprising Mixed Polymeric Micelles and Polynucleotides Associated Therewith.

Heterogeneous polymeric micelles were formed between various combinations of the above-described block copolymers of Example 4.A, according to the following procedures, with minor variations (e.g., substitution of different block copolymers; varying the relative ratio of first block copolymer and second block copolymer, etc.).

Generally, heterogeneous micelles were prepared by providing first block copolymer and a second block copolymer (compositionally distinct from the first polymer) in a denaturing medium to form a heterogeneous mixture of the first polymer and the second polymer. The heterogeneous mixture is then transposed to a second aqueous medium, and the hydrophobic blocks of the first and second copolymers are allowed to associate in the aqueous medium to form the heterogeneous micelle. A polynucleotide can be associated with such heterogeneous polymeric micelle, or alternatively, with at least one of the first or second block copolymers, either before or after heterogeneous micelle formation.

B.1 As a representative example, a heterogeneous (mixed) polymeric micelle was formed from two block copolymers—having compositionally distinct hydrophilic blocks and each having the same hydrophobic block. Specifically, for example, a first block copolymer comprised of a DMAEMA hydrophilic block (e.g., polymer 4.1), and a second block copolymer comprised of a PEGMA hydrophilic block (e.g., polymer 4.2), were combined with a desired ratio (e.g., 1:1) of first polymer to second polymer to form a heterogeneous micelle having a hydrophilic shell comprising polymer blocks of (e.g., 50%) DMAEMA and (e.g., 50%) PEGMA (or other desired ratios), preferably for example, by mixing the corresponding amounts of the first and second block copolymers in 100% ethanol followed by 20-fold dilution in PBS pH 7.4 or dialysis against PBS pH 7.4.

B.2 As another representative example, a heterogeneous (mixed) polymeric micelle was formed from two block copolymers—each having either the same or compositionally distinct hydrophilic blocks, but having compositionally distinct hydrophobic blocks. Specifically, for example, a first block copolymer comprised of a [BMA/PAA/DMAEMA] hydrophobic block (e.g., polymer 4.1), and a second block copolymer comprised of a [BMA] hydrophobic block (e.g., polymer 4.3), were combined with a desired ratio (e.g., 1:1) of first polymer to second polymer to form a heterogeneous micelle having a hydrophobic core comprising polymer blocks of (e.g., 50%) BMA and (e.g., 50%) [BMA/PAA/DMAEMA] (e.g., [50% BMA/25% PAA/25% DMAEMA] as in each of polymer 4.1 and polymer 4.3) (or other desired ratios), preferably for example, by mixing desired corresponding amounts of the first and second block copolymers in 100% ethanol followed by 20-fold dilution in PBS pH 7.4 or dialysis against PBS pH 7.4.

B.3. As a further representative example, a polynucleotide (e.g., siRNA) was associated with the polymeric micelle.

B.3.1. In one approach, the polynucleotide was associated with a cationic hydrophilic block of the first and/or second block copolymers substantially coincident with mixed micelle formation. For example, a composition comprising a mixed polymeric micelle and a polynucleotide associated therewith can be formed from two compositionally distinct block copolymers—where at least one of the block copolymers has a cationic hydrophilic block (e.g., a first block copolymer comprising a DMAEMA monomeric residue in its hydrophilic block (e.g., polymer 4.1, polymer 4.3, polymer 4.5)), was formulated with polynucleotide (e.g., siRNA) by mixing desired relative amounts of the first and second block copolymers in 100% ethanol followed by dilution to 50% ethanol with an equal volume of a solution comprising polynucleotide (e.g., siRNA) in 0.5 M NaCl-PBS pH 7.4, followed by a further 10-fold dilution in PBS pH 7.4 or dialysis against PBS pH 7.4.

B.3.2. Alternatively, in another approach, the polynucleotide was associated with a cationic hydrophilic block of at least one of first and/or second block copolymers prior to formation of the heterogeneous polymeric micelle. For example, a composition comprising a mixed polymeric micelle and a polynucleotide associated therewith can be formed from two compositionally distinct block copolymers—where a first polymer having a cationic hydrophilic block (e.g., comprising DMAEMA monomeric residue in its hydrophilic block (e.g., polymer 4.1, polymer 4.3, polymer 4.5)), was first formulated with polynucleotide (e.g., siRNA) in 50% ethanol, followed by addition of the second polymer in 50% ethanol, followed by 10-fold dilution in PBS pH 7.4 or dialysis against PBS pH 7.4.

B.3.3. In a further approach, the polynucleotide was associated with a cationic hydrophilic block of at least one of first and/or second block copolymers after formation of the heterogeneous polymeric micelle. For example, heterogeneous polymeric micelle was formed, for example, substantially as described above in Example B.1 or Example B.2. A polynucleotide is subsequently associated therewith by mixing the polynucleotide (e.g., siRNA with the polymeric micelle in PBS pH 7.4, followed by dialysis against PBS pH 7.4

B.3.4. In a different approach, a polynucleotide was covalently associated with the heterogeneous polymeric micelle by covalent conjugation to the first and/or second block copolymers. For example, a composition comprising a mixed polymeric micelle and a polynucleotide associated therewith can be formed from two compositionally distinct block copolymers—where at least one of the first polymer or the second polymer have a hydrophilic block which comprises a conjugatable monomeric residue (e.g., comprising MAA(NHS) monomeric residue (e.g., polymer 4.4))—for example, by (i) forming the heterogeneous polymeric micelle first substantially as described above in Example B.1 or Example B.2, and subsequently effecting conjugation of the polynucleotide (e.g., as described in Example 3.2), or alternatively by (ii) first forming a polynucleotide-conjugated block copolymer (e.g., as described in Example 3.2), and subsequently effecting formation of the heterogeneous polymeric micelle substantially as described above in Example B.1 or Example B.2. Table 4.B.1 summarizes various heterogeneous micelles prepared as set forth herein.

TABLE 4.B.1

| Polymer | | % Polymer | Micelle |
|---|---|---|---|
| $[D]_{14K}$-$[B_{50}$-$P_{25}$-$D_{25}]_{30K}$ | 4.1 | 50% | M.1 |
| $[PEGMA]_{24K}$-$[B_{50}$-$P_{25}$-$D_{25}]_{30K}$ | 4.2 | 50% | |
| $[D]_{14K}$-$[B_{50}$-$P_{25}$-$D_{25}]_{30K}$ | 4.1 | 50% | M.2 |
| $[D]_{14K}$-$[B]_{30K}$ | 4.3 | 50% | |
| $[D]_{10K}$-$[B_{50}$-$P_{25}$-$D_{25}]_{30K}$ | 4.6 | 95% | M.3.1 |
| $[PEGMA]_{18K}$-$[B_{50}$-$P_{25}$-$D_{25}]_{30K}$ | 4.7 | 5% | |
| $[D]_{10K}$-$[B_{50}$-$P_{25}$-$D_{25}]_{30K}$ | 4.6 | 90% | M.3.2 |
| $[PEGMA]_{18K}$-$[B_{50}$-$P_{25}$-$D_{25}]_{30K}$ | 4.7 | 10% | |
| $[D]_{10K}$-$[B_{50}$-$P_{25}$-$D_{25}]_{30K}$ | 4.6 | 80% | M.3.3 |
| $[PEGMA]_{18K}$-$[B_{50}$-$P_{25}$-$D_{25}]_{30K}$ | 4.7 | 20% | |
| $[D]_{10K}$-$[B_{50}$-$P_{25}$-$D_{25}]_{30K}$ | 4.6 | 50% | M.3.4 |
| $[PEGMA]_{18K}$-$[B_{50}$-$P_{25}$-$D_{25}]_{30K}$ | 4.7 | 50% | |
| $[D]_{10K}$-$[B_{50}$-$P_{25}$-$D_{25}]_{30K}$ | 4.6 | 25% | M.3.5 |
| $[PEGMA]_{18K}$-$[B_{50}$-$P_{25}$-$D_{25}]_{30K}$ | 4.7 | 75% | |
| $[D]_{10K}$-$[B_{50}$-$P_{25}$-$D_{25}]_{30K}$ | 4.6 | 50% | M.4 |
| $[PEGMA]_{24K}$-$[B_{50}$-$P_{25}$-$D_{25}]_{30K}$ | 4.2 | 50% | |
| $[D]_{14K}$-$[B_{50}$-$P_{25}$-$D_{25}]_{30K}$ | 4.1 | 50% | M5.1 |
| $[PEGMA]_{40K}$-$[B_{53}$-$P_{26}$-$D_{21}]_{60K}$ | 4.8 | 50% | |
| $[D]_{14K}$-$[B_{50}$-$P_{25}$-$D_{25}]_{30K}$ | 4.1 | 25% | M5.2 |
| $[PEGMA]_{40K}$-$[B_{53}$-$P_{26}$-$D_{21}]_{60K}$ | 4.8 | 75% | |

Table 4.B.2 summarizes various prophetic additional heterogeneous micelles which can be prepared as described herein

TABLE 4.B.2

(Prophetic)

| Polymer | | % Polymer | Micelle |
|---|---|---|---|
| $[D]_{14K}$-$[B_{50}$-$P_{25}$-$D_{25}]_{30K}$ | (4.1) | 50% | PM.1 |
| $[PEGMA_{70}$-MAA(Gal)$_{30}]_{24K}$- $[B_{50}$-$P_{25}$-$D_{25}]_{30K}$ | (4.4.1) | 50% | |
| $[PEGMA_{70}$-MAA-(RNA)$_{30}]_{24K}$- $[B_{50}$-$P_{25}$-$D_{25}]_{30K}$ | (4.4.2) | 50% | PM.2 |
| $[PEGMA]_{24K}$-$[B_{50}$-$P_{25}$-$D_{25}]_{30K}$ | (4.2) | 50% | |
| $[PEGMA_{70}$-MAA-(RNA)$_{30}]_{24K}$- $[B_{50}$-$P_{25}$-$D_{25}]_{30K}$ | (4.4.2) | 50% | PM.3 |
| $[PEGMA_{70}$-MAA(Gal)$_{30}]_{24K}$- $[B_{50}$-$P_{25}$-$D_{25}]_{30K}$ | (4.4.1) | 25% | |
| $[PEGMA_{70}$-DMAEMA$_{30}]_{24K}$- $[B_{50}$-$P_{25}$-$D_{25}]_{30K}$ | (4.5) | 25% | |

Alternative heterogeneous micelles and compositions comprising such micelles and a polynucleotide associated therewith can comprise (additional or alternative) other targeting ligands (e.g., folate), for example, as substituted for galactose (Gal) in the heterogeneous micelles PM.1, PM.2, PM.3.

Example 5

Physical Characterization of Heterogeneous Polymeric Micelles

This example characterizes heterogeneous micelles, using proton Nuclear Magnetic Resonance (1H NMR) spectroscopy and Dynamic Light Scattering (DLS), and demonstrates that heterogeneous micelles were prepared, for example by formulating compositionally distinct polymers in a denaturing solvent, and then allowing these polymers to associate to form a mixed micelle structure when transferred to aqueous solution.

A. $^1$H NMR analysis of mixed micelles. Generally, $^1$H NMR spectra were recorded on a Bruker AV301 nuclear magnetic resonance instrument in deuterated chloroform (CDCl3), deuterated water (D2O), or deuterated phosphate buffer, at 25° C. A deuterium lock (CDCl3, D2O) was used, and chemical shifts were determined in ppm from tetramethylsilane (for CDCl3) and 3-(trimethylsilyl)propionic-2,2,3,3-d4 acid, sodium salt (for D2O). Polymer concentration was typically 6 mg/ml.

Figure 7A:
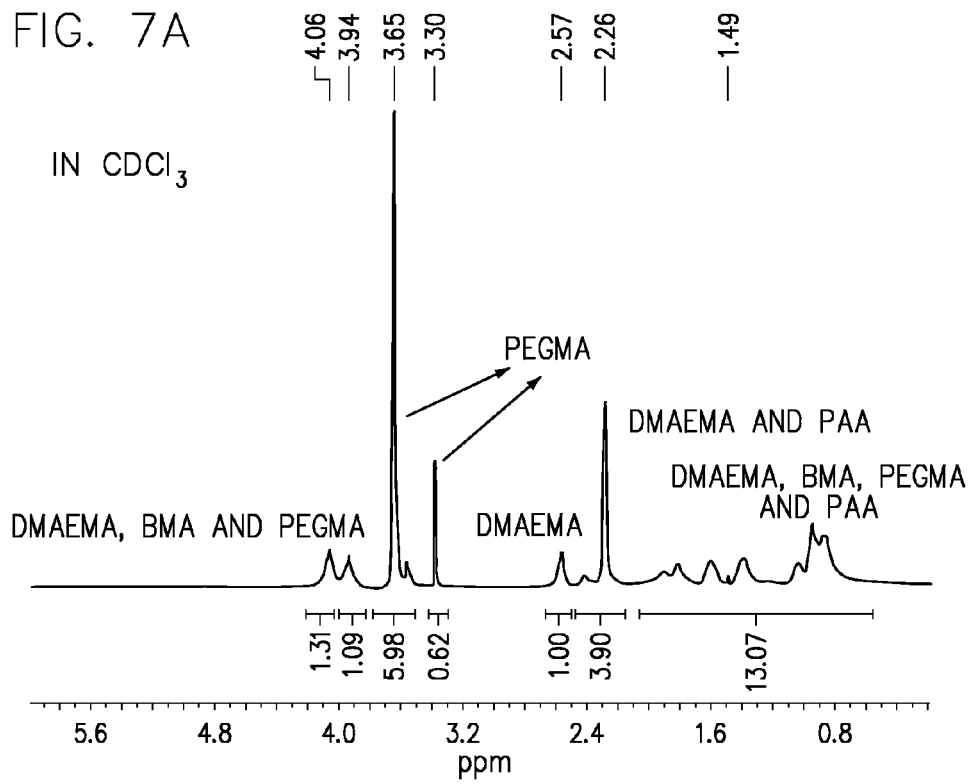
FIGS. 7A and 7B are graphs showing the $^1$H NMR analysis of a heterogeneous micelle M.4 comprising block copolymers having compositionally distinct hydrophilic blocks—a first polymer having a DMAEMA hydrophilic block and a second polymer having a PEGMA hydrophilic block—and substantially the same hydrophobic block, including NMR spectra in organic solvent $CDCL_3$ (FIG. 7A) and in an aqueous solvent deuterated phosphate buffer, pH 7.4 (FIG. 7B).
Figure 7B:
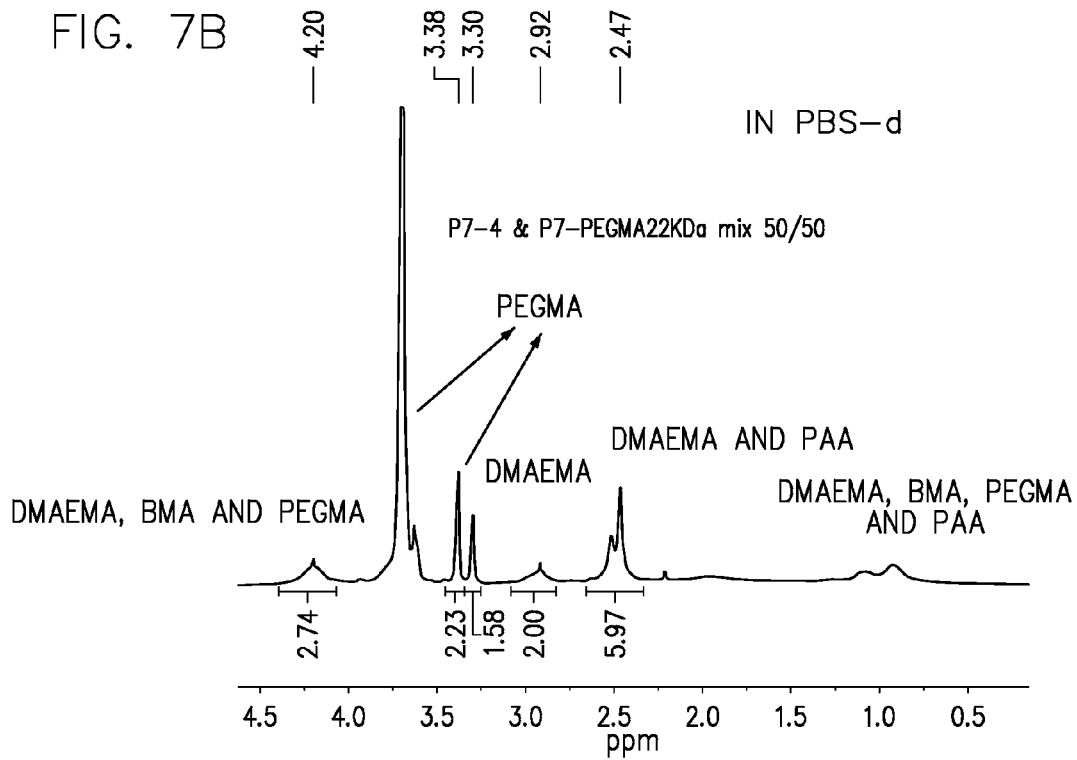

FIGS. 7A and 7B show the $^1$H NMR analysis of a heterogeneous micelle M.4 comprising block copolymers having compositionally distinct hydrophilic blocks—a first polymer having a DMAEMA hydrophilic block and a second polymer having a PEGMA hydrophilic block, and substantially the same hydrophobic blocks:

| Polymer | | % Polymer | Micelle |
|---|---|---|---|
| $[D]_{10K}$-$[B_{50}$-$P_{25}$-$D_{25}]_{30K}$ | 4.6 | 50% | M.4 |
| $[PEGMA]_{24K}$-$[B_{50}$-$P_{25}$-$D_{25}]_{30K}$ | 4.2 | 50% | |

NMR spectra in the organic solvent $CDCL_3$ (FIG. 7A, left panel) shows that all proton resonances are visible and accounted for and integrate to values consistent with the polymeric composition of the polymer in the non-micelle state. NMR spectra in the aqueous solvent deuterated phosphate buffer, pH 7.4 (FIG. 7B, right panel) shows that the protons associated with the hydrophobic residues in the core block are highly suppressed, consistent with the formation of a shielded hydrophobic micelle core. In contrast, the integrations relative to PEGMA protons and DMAEMA protons indicate that PEGMA and DMAEMA are both water exposed.

B. DLS analysis of mixed micelles. Generally, particle sizes of polymeric micelles were measured by dynamic light scattering (DLS) using a Malvern Zetasizer Nano ZS instrument. Particle sizes were calculated using the instrument's Particle Sizing Software.

Figure 8A:
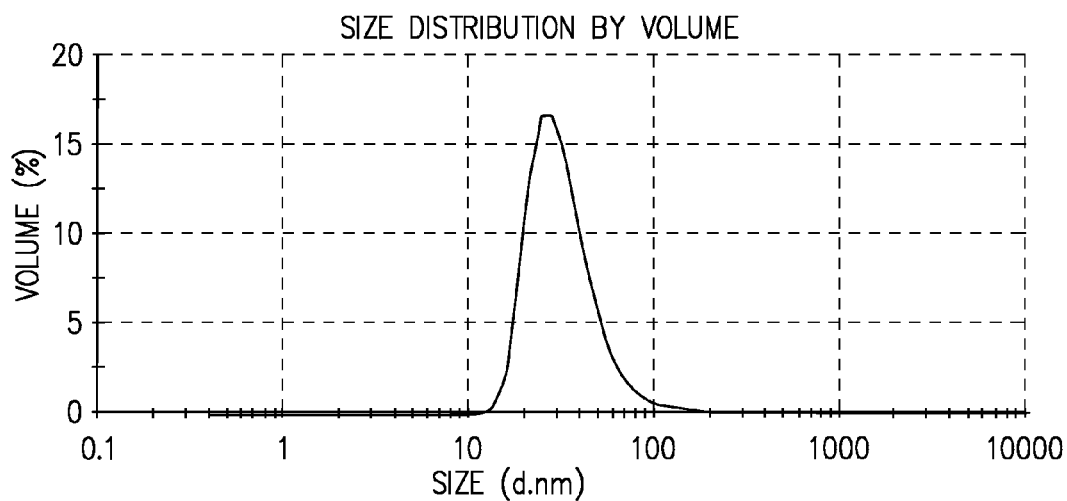
FIGS. 8A and 8B are graphs showing data from determination of particle size by dynamic light scattering (DLS) for two heterogeneous polymeric micelles, including micelle M.1 comprising block copolymers having compositionally distinct hydrophilic blocks—a first polymer having a DMAEMA hydrophilic block and a second polymer having a PEGMA hydrophilic block, and substantially the same hydrophobic blocks (FIG. 8A), and independently, micelle M.2 comprising block copolymers having substantially the same hydrophilic block and compositionally distinct hydrophobic blocks—a first polymer having a [BMA/PAA/DMAEMA] hydrophobic block and a second polymer having a BMA hydrophobic block (FIG. 8B).
Figure 8B:
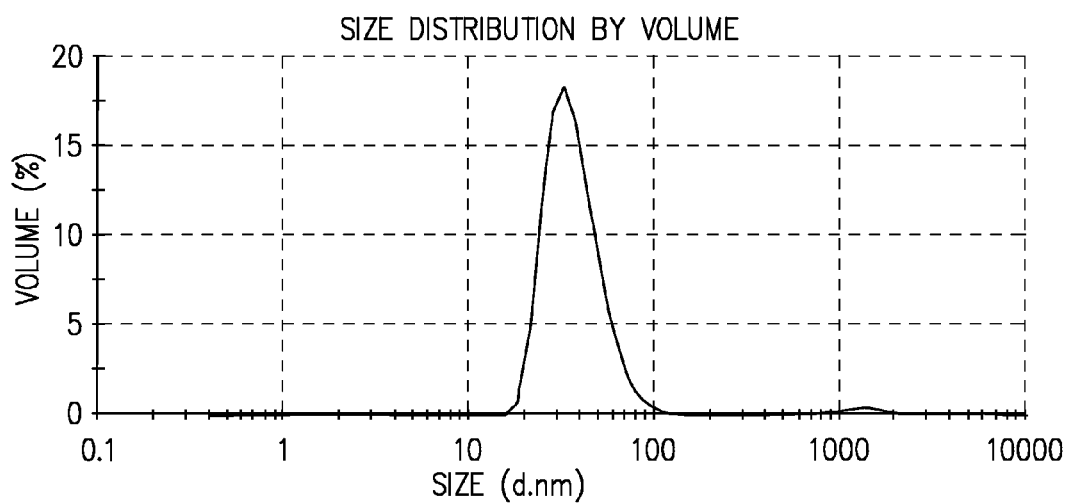

FIGS. 8A and 8B show data for determination of the particle size for two heterogeneous polymeric micelles: (1) micelle, M.1 (FIG. 8A) comprising block copolymers having compositionally distinct hydrophilic blocks—a first polymer having a DMAEMA hydrophilic block and a second polymer having a PEGMA hydrophilic block, and substantially the same hydrophobic blocks,

| | | | |
|---|---|---|---|
| $[D]_{14K}-[B_{50}-P_{25}-D_{25}]_{30K}$ | 4.1 | 50% | M.1 |
| $[PEGMA]_{24K}-[B_{50}-P_{25}-D_{25}]_{30K}$ | 4.2 | 50% | | and independently, (2) micelle M.2 (FIG. 8B) comprising block copolymers having substantially the same hydrophilic block and compositionally distinct hydrophobic blocks—a first polymer having a [BMA/PAA/DMAEMA] hydrophobic block and a second polymer having a BMA hydrophobic block:

| | | | |
|---|---|---|---|
| $[D]_{14K}-[B_{50}-P_{25}-D_{25}]_{30K}$ | 4.1 | 50% | M.2 |
| $[D]_{14K}-[B]_{30K}$ | 4.3 | 50% | |

For comparison, particle sizes were also independently determined for three separate, corresponding homogenous micelles—one homogeneous micelle consisting essentially of a singular block copolymer 4.1, having a representative formula $$[D]_{14K}-[B_{50}-P_{25}-D_{25}]_{30K} \qquad (4.1),$$

and independently, another homogeneous micelle consisting essentially of a singular block copolymer 4.2, having a representative formula $$[PEGMA]_{24K}-[B_{50}-P_{25}-D_{25}]_{30K} \qquad (4.2)$$

and independently, a third homogeneous micelle consisting essentially of a singular block copolymer 4.3, having a representative formula $$[D]_{14K}-[B]_{30K} \qquad (4.3).$$

DLS analysis indicated that the particle size of the homogeneous polymeric micelle prepared from polymer 4.1 was 50 nm (data not shown) and that the particle size of the homogeneous polymeric micelle prepared from polymer 4.2 was 35 nm (data not shown). In comparison, the particle size for the mixed micelle M.1 (formed from a 1:1 ratio of the polymers 4.1 and 4.2) was determined to have an intermediate value of approximately 44 nm (z-average diameter) (FIG. 8A, upper panel). In a separate analysis DLS demonstrated that polymer 4.3 containing only BMA in the hydrophobic block formed a turbid aqueous solution with particles greater than 200 nm in size (data not shown). However, when the mixed micelle M.2 was formulated from a 1:1 ratio of the polymers 4.1 and 4.3 a clear (non-turbid) aqueous solution was obtained, resulting in heterogeneous micelles having approximately 50 nm particle size and being substantially of uniform size (FIG. 8B, lower panel).

Example 6

Biological Characterization of Heterogeneous Polymer Micelles

This example demonstrates that heterogeneous polymeric micelles were prepared which (i) effectively bind polynucleotides, (ii) effectively shield for polycationic-mediated toxicity, (iii) have tissue-selective in vivo distribution, and (iv) effectively modulate gene-expression activity. Notably, these examples also demonstrate that heterogeneous micelles of the invention were controllably tunable (e.g., as to polymer composition, polymer architecture, and supramolecular composition) to achieve varied heterogeneous polymeric micelles having different biological properties.

Experiments were performed to evaluate heterogeneous polymeric micelles having distinct biological properties, based on controlled variation in aspects such as block copolymer composition, polymer architecture and supramolecular (e.g., micellic) composition. Various block copolymer compositions were evaluated, for example, with respect to the chemical composition of the hydrophilic block of constituent block copolymers, which collectively form the shell of micelle that is exposed to the aqueous environment. Notably, heterogeneous polymeric micelles containing polycationic monomeric residues (e.g., DMAEMA) within the shell-forming hydrophilic blocks were shown to efficiently bind polynucleic acids such as siRNA, and advantageously, such polycationic compositions were show to be effectively shielded in polymeric micelles containing neutral hydrophilic monomeric residues (e.g., PEGMA) within the shell-forming hydrophilic block, and thereby effectively mediating potential toxicity. Notably, these experiments also show that such polynucleotide-binding functionality and shielding functionality was effectively combined with other important functionalities, such as tissue-selective delivery, and such as endosomal membrane-destabilizing activity—in heterogeneous polymeric micelles effective for polynucleotide (e.g., siRNA) delivery. Representative experiments are described in further detail herein.

A. Toxicity and RNA binding analysis of mixed polymeric'micelles. Generally, polynucleotide (e.g., RNA) binding was determined by the method described in Cardoso A L C et al., J Gene Medicine 2007; 9: 170-183). Generally, toxicity was determined by a protocol which included injecting various concentrations of polymeric micelle compositions (or control compositions) into normal healthy mice via tail vein, and determining the minimum dose (e.g., of polymer or micelle) observed to be lethal to the mice.

FIG. 9 shows a table summarizing relative toxicity and polynucleotide-binding properties for two separate homogenous micelles—one homogeneous micelle consisting essentially of a singular block copolymer 4.6, having a representative formula $$[D]_{10K}-[B_{50}-P_{25}-D_{25}]_{30K} \qquad (4.6)$$

and independently, another homogeneous micelle consisting essentially of a singular block copolymer 4.7, having a representative formula $$[PEGMA]_{18K}-[B_{50}-P_{25}-D_{25}]_{30K} \qquad (4.7)$$

as well as for various mixed micelles formed with different relative ratios of polymer 4.6 and polymer 4.7: M3.1 (95%/5%), M3.2 (90%/10%), M3.3 (80%/20%), M3.4 (50%/50%), and M3.5 (25%/75%), The homogeneous polymeric micelle consisting essentially of a singular block copolymer 4.6, and containing essentially only hydrophilic cationic DMAEMA monomeric residues in its shell, shows relatively high RNA binding (IC$_{50}$ of about 3.75 ug/ml polymer) and relatively high toxicity (observable at moderate doses of about 15 mg/kg of polymer). In contrast, the homogeneous polymeric micelle consisting essentially of a singular block copolymer 4.7, and containing essentially only hydrophilic neutral PEGMA monomeric residues in its shell, shows no observable toxicity at the highest dose tested in mice and no observed RNA binding within the sensitivity of the assay. Notably, analysis of mixed polymeric micelles M.1, M.2, M.3, M.4 and M.5 shows a range of RNA-binding (IC$_{50}$ ranging from about 5.0 to about 16.0 ug/ml of polymeric micelle), and a range of observed toxicity (doses ranging from about 15 mg/kg to >50 mg/kg of polymeric micelle), with such ranges corresponding to various relative ratios of copolymers included in the heterogeneous micelle. As a non-limiting example, a heterogeneous micelle with a 1:1 ratio of polymers 4.6:4.7 has relatively reduced toxicity in vivo (about 20 mg/kg polymeric micelle) and retains effective although reduced siRNA binding (IC$_{50}$ of about 8.6 ug/ml of polymeric micelle).

Figure 10:
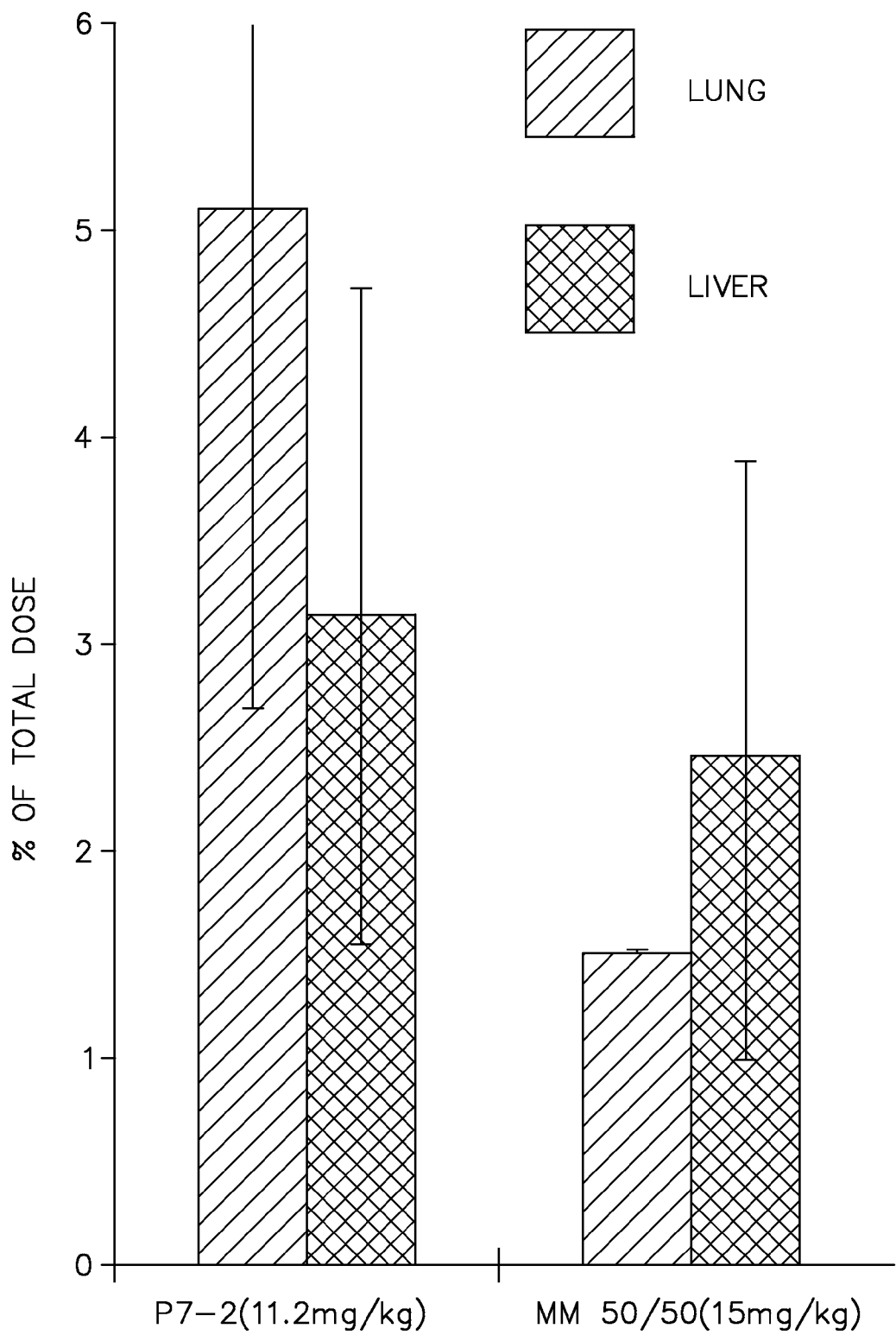
FIG. 10 is a graph showing tissue-selective in-vivo biodistribution resulting from injection of mice with a homogeneous polymeric micelle consisting essentially of a singular block copolymer 4.1 (designated as polymer "P7-2" in FIG. 10) and independently, with a heterogeneous polymeric micelle M.4 (designated as "MM 50/50") comprising a 1:1 ratio of polymer 4.1 and polymer 4.2—block copolymers having compositionally distinct hydrophilic blocks—a first polymer having a DMAEMA hydrophilic block and a second polymer having a PEGMA hydrophilic block, and substantially the same hydrophobic blocks.

B. Selective in vivo biodistribution of a mixed polymeric micelle. FIG. 10 demonstrates that mixed polymer micelles prepared as described herein have differentiated selectivity for tissue-directed delivery of siRNA.

Mice were injected with a preparation of homogeneous polymeric micelle consisting essentially of a singular block copolymer 4.1 (designated as polymer "P7-2" in FIG. 10), $$([D]_{14K}\text{-}[B_{50}\text{-}P_{25}\text{-}D_{25}]_{30K}) \quad 4.1$$

(dosed at a concentration of 11.2 mg/kg), and independently, with a heterogeneous polymeric micelle M.4 comprising a 1:1 ratio of polymer 4.1 and polymer 4.2

| | | | |
|---|---|---|---|
| $[D]_{14K}\text{-}[B_{50}\text{-}P_{25}\text{-}D_{25}]_{30K}$ | 4.1 | 50% | M.1 |
| $[PEGMA]_{24K}\text{-}[B_{50}\text{-}P_{25}\text{-}D_{25}]_{30K}$ | 4.2 | 50% | |

(dosed at a concentration of 15 mg/kg). The homogeneous polymeric micelle showed relatively higher delivery of siRNA to lungs (with higher toxicity) as compared to liver, while in contrast, the mixed polymeric micelle M.1 shows relatively higher delivery of siRNA to liver (with lower toxicity) as compared to lung C. In vitro gene silencing activity for compositions comprising mixed polymeric micelles formulated with siRNA.

Figure 11A:
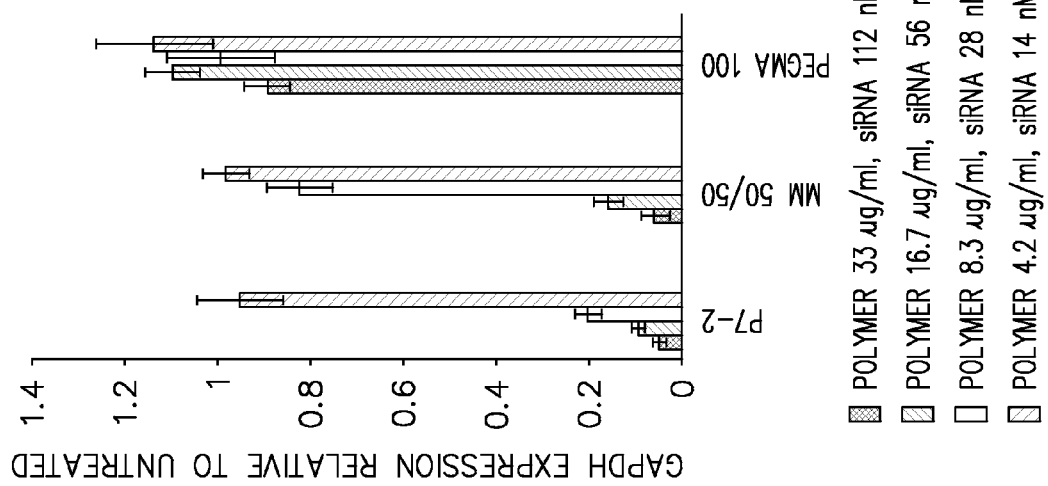
FIGS. 11A and 11B are graphs showing knockdown activity for'expression of GAPDH in HeLa cells (reported as normalized relative to expression of GAPDH in untreated HeLa cells), for compositions comprising siRNA associated with homogeneous and heterogeneous micelles, including a homogeneous micelle consisting essentially of a singular block copolymer 4.1 (designated as "P7-2" in FIGS. 11A and 11B) having a DMAEMA hydrophilic block, another homogeneous micelle consisting essentially of a singular block copolymer 4.8 (designated as "PEGMA 100" in FIGS. 11A and 11B) having a PEGMA hydrophilic block, as well as heterogeneous polymeric mixed micelles M.5.1, and M.5.2 (designated as "MM 50/50" and "MM 25/75" respectively in FIGS. 11A and 11B) formed with different relative ratios of polymer 4.1 and polymer 4.8.
Figure 11B:
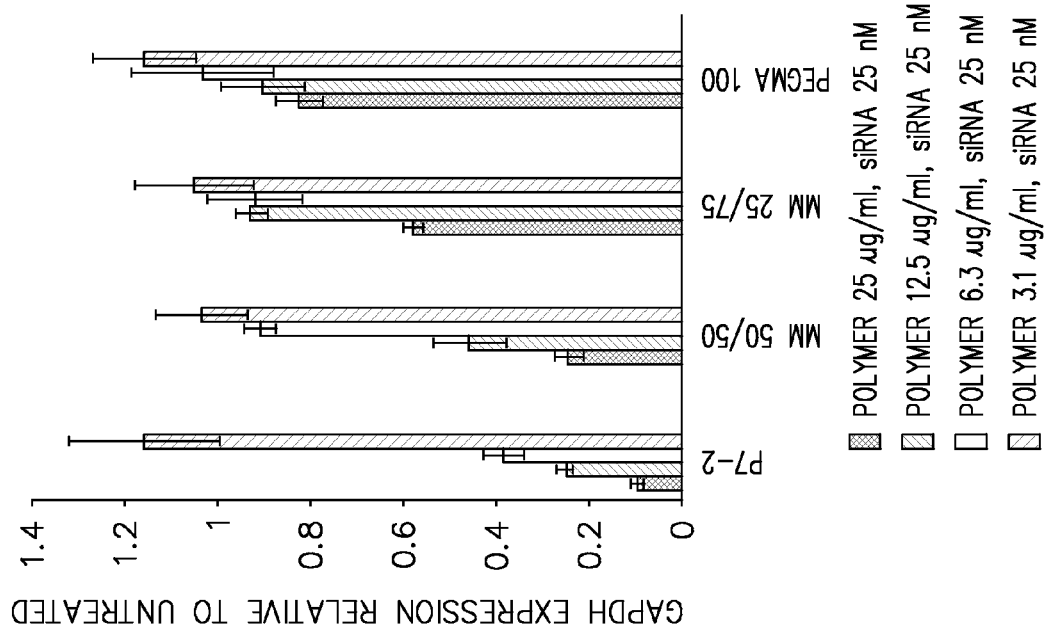

FIGS. 11A and 11B demonstrate that mixed polymeric micelles prepared as described herein were effective to knockdown gene expression activity under several formulation conditions. Knock-down (KD) activity of compositions comprising a heterogeneous polymeric micelle and an associated polynucleotide (e.g., an siRNA known to have knockdown activity for GAPDH gene expression) was determined.

Specifically, two separate homogenous micelles—one homogeneous micelle consisting essentially of a singular block copolymer 4.1, having a representative formula $$[D]_{14K}\text{-}[B_{50}\text{-}P_{25}\text{-}D_{25}]_{30K} \quad (4.1)$$

(designated as micelle "P7-2" in FIG. 11), and independently, another homogeneous micelle consisting essentially of a singular block copolymer 4.8, having a representative formula $$[PEGMA]_{40K}\text{-}[B_{53}\text{-}P_{26}\text{-}D_{21}]_{60K} \quad (4.8)$$

(designated as micelle "PEGMA 100" in FIG. 11) were evaluated. Heterogeneous micelles formed with different relative ratios of polymer 4.1 and polymer 4.8-M5.1 (50%/50%) (designated as micelle "MM 50/50" in FIG. 11) and M5.2 (25%/75%) (designated as micelle "MM 25/75" in FIG. 11), were also evaluated.

Variations in siRNA-formulation protocols were also evaluated. In a first set of experiments, (FIG. 11A, left panel), siRNA was associated, independently, with each of the aforementioned homogeneous polymeric micelles (homogeneous-4.1-micelle; homogeneous-4.8 micelle), and heterogeneous polymeric micelles (M5.1 and M5.2) substantially as described in Example B.3.1 using, in each case, a 25 nM siRNA and concentrations of total polymer as indicated in the associated legend. In a second set of experiments, (FIG. 11B, right panel), siRNA was associated, independently, with each of the aforementioned homogeneous polymeric micelles (homogeneous-4.1-micelle; homogeneous-4.8 micelle) and heterogeneous polymeric micelles (M5.1) substantially as described in Example B.3.2 and using for each case, various amount of siRNA ranging from 14 nM to 112 nM formulated with various concentrations of total polymer ranging from 4.2 ug/ml to 33 ug/ml (as specifically detailed in FIG. 11).

The knockdown assay measured specific gene expression after 24 hours of treatment with polymer:siRNA complexes. The homogeneous or heterogeneous polymeric micelles being evaluated and the GAPDH-modulating siRNA, (or a negative control siRNA—a non-active siRNA lacking knockdown activity for GAPDH gene expression (data not shown)) were mixed in 25 uL to obtain various concentrations at 5-fold over final transfection concentration and allowed to complex for 30 minutes before addition to HeLa cells in 100 uL normal media containing 10% FBS. Final siRNA and polymer concentrations were evaluated as indicated in FIG. 11A and FIG. 11B. Total RNA was isolated 24 hours post treatment and GAPDH expression was measured relative to two internal normalizer genes, RPL13A and HPRT, by quantitative PCR:

Results in FIGS. 11A and 11B compare the knockdown activity of compositions comprising siRNA associated with each of the homogeneous-4.1-micelle, the homogeneous-4.8-micelle, and the heterogeneous polymeric mixed micelles M.5.1, and M.5.2, in each case normalized relative to expression of GAPDH in untreated HeLa cells.

The homogeneous-4.8-micelle (designated as "PEGMA 100" in FIGS. 11A and 11B) having a hydrophilic shell consisting essentially neutral PEGMA monomeric residue showed little or no knock-down activity whereas the homogeneous-4.1-micelle (designated as "P7-2" in FIGS. 11A and 11B) having a hydrophilic shell consisting essentially cationic DMAEMA monomeric residue showed substantial knock-down activity. These observed results are consistent with siRNA binding determined for homogeneous micelles formed from substantially similar polymers 4.7 (no binding) and 4.6 (IC$_{50}$ 3.75 ug/ml) as observed in Example 6.A (FIG. 9). The mixed polymer micelle M5.1 comprising the block copolymers 4.1 and 4.8 (50% 150%) (designated as "MM 50/50" in FIGS. 11A and 11B) having a hydrophilic shell consisting essentially of equal molar amounts cationic DMAEMA and neutral PEGMA monomeric residues has knockdown activity substantially similar to the homogeneous-4.1-micelle (designated as "P7-2" in FIGS. 11A and 11B). Notably, however, the heterogeneous micelle M5.1 is expected to have reduced in vivo toxicity as compared to the homogeneous-4.1-micelle, based on in-vivo toxicity data for similarly-constituted heterogeneous micelle M.3.4 (non-toxic dose at least 20 mg/kg) and homogeneous micelle formed from polymers 4.6 (non-toxic dose<11.5 mg/kg) as observed in Example 6.A (FIG. 9). Therefore, these data demonstrate that compositions comprising heterogeneous micelles and siRNA associated therewith have significant activity for siRNA-mediated inhibition of gene expression, with reduced toxicity (relative to homogeneous micelles formed from common constituent polymers).

The various examples herein are to be considered illustrative, and not defining the scope of the invention.

We claim:

1. A composition comprising a heterogeneous polymeric micelle and a polynucleotide associated with the micelle, the micelle comprising:
   a first polymer, the first polymer being a block copolymer comprising a hydrophilic block and a hydrophobic block; and
   a second polymer compositionally distinct from the first polymer, the second polymer being a block copolymer comprising a hydrophilic block and a hydrophobic block, the hydrophobic block of the second polymer being associated with the hydrophobic block of the first polymer such that the micelle is stable in an aqueous medium at pH 7.4,
   wherein at least one of the first polymer or the second polymer comprises a pH-dependent, membrane-destabilizing polymer;
   wherein the hydrophilic block of the first polymer comprises a plurality of cationic monomeric residues in ionic association with the polynucleotide,
   wherein the hydrophilic block of the second polymer is a neutral hydrophilic block comprising a plurality of neutral polar residues, and
   wherein the first polymer or the second polymer is a block copolymer of Formula IA:

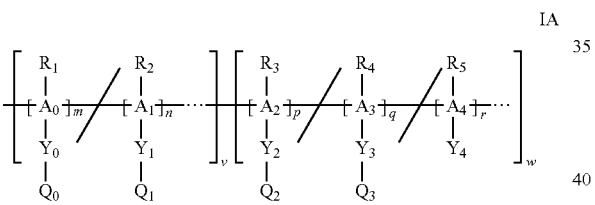

wherein
$A_0$, $A_1$, $A_2$, $A_3$, and $A_4$ are each independently selected from the group consisting of —$CH_2$—, —C—C—, —C(O)(C)$_a$C(O)O—, —O(C)$_a$C(O)— and —O(C)$_b$O—;
a is an independently selected integer ranging from 1-4;
b is an independently selected integer ranging from 2-4;
m ranges from 0 to less than 1.0;
n ranges from greater than 0 to about 1.0;
the sum of (m+n)=1;
p ranges from about 0.1 to about 0.9;
q ranges from about 0.1 to about 0.9;
r ranges from 0 to about 0.8;
the sum of (p+q+r)=1;
$Y_0$, $Y_1$, and $Y_2$ are each independently selected from the group consisting of a covalent bond, (1C-10C)alkyl-, —C(O)O(2C-10C) alkyl-, —OC(O)(1C-10C) alkyl-, —O(2C-10C) alkyl-, —S(2C-10C) alkyl-, and —C(O)NR$_6$(2C-10C) alkyl-;
$Y_3$ is selected from the group consisting of a covalent bond, (1C-10C) alkyl and (6C-10C) aryl;
$Y_4$ is selected from the group consisting of hydrogen, (1C-10C) alkyl, (3C-6C) cycloalkyl, O-(1C-10C) alkyl, —C(O)O(1C-10C) alkyl, C(O)NR$_6$(1C-10C), and aryl, any of which is optionally substituted with one or more fluorine groups;
tetravalent carbon atoms of $A_0$-$A_4$ that are not fully substituted with $R_1$-$R_5$; and
$Y_0$-$Y_4$ are substituted with a valency-appropriate number of hydrogen atoms;
$R_1$, $R_2$, $R_3$, $R_4$, $R_5$, and $R_6$ are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;
$Q_0$ is selected from the group consisting of hydrogen, hydrophilic species (at physiologic pH), L conjugatable species and functional species;
$Q_1$ is a species which is hydrophilic at physiologic pH;
$Q_2$ is a species which is positively charged at physiologic pH;
$Q_3$ is a species which is negatively charged at physiologic pH, but undergoes protonation at lower pH;
v corresponds to a molecular weight from about 5 to about 25 kDa; and,
w corresponds to a molecular weight from about 5 to about 50 kDa.

2. The composition of claim 1, wherein the polynucleotide is an siRNA.

3. A method for intracellular delivery of a polynucleotide, the method comprising:
   contacting a composition of claim 1 with a cell surface in a medium at a first pH;
   introducing the composition into an endosomal membrane within the cell through endocytosis; and
   destabilizing the endosomal membrane, whereby the composition or the polynucleotide is delivered to the cytosol of the cell.

4. The composition of claim 1, wherein the hydrophobic block of the second polymer is compositionally distinct from the hydrophobic block of the first polymer.

5. The composition of claim 1, wherein the hydrophobic block of the second polymer has substantially the same composition as the hydrophobic block of the first polymer.

6. The composition of claim 1, wherein the second polymer comprises one or more monomeric residues that are different than the monomeric residues of the first polymer.

7. The composition of claim 1, further comprising a targeting moiety.

8. The composition of claim 1, comprising a targeting moiety, wherein the targeting moiety is a ligand having affinity for one or more receptors effective for mediating endocytosis.

9. The composition of claim 1, comprising a targeting moiety, wherein the targeting moiety is covalently coupled to a hydrophilic block of the first polymer or to a hydrophilic block of the second polymer.

* * * * *

UNITED STATES PATENT AND TRADEMARK OFFICE
CERTIFICATE OF CORRECTION

PATENT NO. : 9,211,250 B2  
APPLICATION NO. : 13/059946  
DATED : December 15, 2015  
INVENTOR(S) : Johnson et al.

Page 1 of 1

It is certified that error appears in the above-identified patent and that said Letters Patent is hereby corrected as shown below:

COLUMN     LINE

1     35-38     Delete the entire paragraph beginning "This invention was made with Government support..." and substitute therefor --This invention was made with government support under R01 EB002991, awarded by the National Institutes of Health. The government has certain rights in the invention.--

Signed and Sealed this  
Ninth Day of August, 2016

Michelle K. Lee  
*Director of the United States Patent and Trademark Office*